(12) United States Patent
Jay et al.

(10) Patent No.: US 10,967,048 B2
(45) Date of Patent: Apr. 6, 2021

(54) USE OF PRG4 AS AN ANTI-INFLAMMATORY AGENT

(71) Applicant: Lubris LLC, Framingham, MA (US)

(72) Inventors: Gregory D. Jay, Norfolk, MA (US); Benjamin D. Sullivan, San Diego, CA (US); Tannin Avery Schmidt, Calgary (CA); Khaled Elsaid, Boston, MA (US); Edward R. Truitt, San Diego, CA (US); Roman Krawetz, Calgary (CA); Jawed Fareed, Westchester, IL (US)

(73) Assignee: Lubris LLC, Framingham, MA (US)

( * ) Notice: Subject to any disclaimer, the term of this patent is extended or adjusted under 35 U.S.C. 154(b) by 0 days.

(21) Appl. No.: 15/546,192

(22) PCT Filed: Jan. 26, 2016

(86) PCT No.: PCT/US2016/014952
§ 371 (c)(1),
(2) Date: Jul. 25, 2017

(87) PCT Pub. No.: WO2016/123123
PCT Pub. Date: Aug. 4, 2016

(65) Prior Publication Data
US 2018/0015141 A1 Jan. 18, 2018

Related U.S. Application Data

(60) Provisional application No. 62/273,059, filed on Dec. 30, 2015, provisional application No. 62/107,799, filed on Jan. 26, 2015.

(51) Int. Cl.
*A61K 38/17* (2006.01)
*A61P 1/00* (2006.01)

(52) U.S. Cl.
CPC .......... *A61K 38/1709* (2013.01); *A61K 38/17* (2013.01); *A61P 1/00* (2018.01)

(58) Field of Classification Search
CPC .... A61K 38/17; A61K 38/1709; A61K 45/06; A61K 9/0014; A61K 9/0019; A61K 9/0043; A61K 9/0048; A61K 9/0053; A61K 9/08; A61K 1/00; A61M 15/08; A61P 19/02
See application file for complete search history.

(56) References Cited

U.S. PATENT DOCUMENTS

| | | |
|---|---|---|
| 6,433,142 B1 | 8/2002 | Turner et al. |
| 6,743,774 B1 | 6/2004 | Jay |
| 6,960,562 B2 | 11/2005 | Jay |
| 7,001,881 B1 | 2/2006 | Jay |
| 7,030,233 B2 | 4/2006 | D'Elia et al. |
| 7,361,738 B2 | 4/2008 | Turner et al. |
| 7,415,381 B2 | 8/2008 | Jay |
| 7,618,941 B2 | 11/2009 | Jay |
| 7,642,236 B2* | 1/2010 | Flannery ................ C07K 14/47 514/1.1 |
| 8,026,346 B2 | 9/2011 | Jay |
| 8,506,944 B2 | 8/2013 | Sullivan et al. |
| 8,551,467 B2 | 10/2013 | Sullivan et al. |
| 8,563,028 B2 | 10/2013 | Sullivan et al. |
| 8,680,057 B2 | 3/2014 | Jay |
| 8,945,604 B2 | 2/2015 | Sullivan et al. |
| 8,980,840 B2 | 3/2015 | Truitt, III et al. |
| 9,107,885 B2 | 8/2015 | Sullivan et al. |
| 9,138,457 B2 | 9/2015 | Sullivan et al. |
| 9,248,161 B2 | 2/2016 | Sullivan et al. |
| 9,393,285 B2 | 7/2016 | Sullivan et al. |
| 9,421,241 B2 | 8/2016 | Sullivan et al. |
| 9,585,936 B2 | 3/2017 | Sullivan et al. |
| 9,730,865 B2 | 8/2017 | Sullivan et al. |
| 9,730,978 B2 | 8/2017 | Sullivan et al. |
| 2006/0240037 A1 | 10/2006 | Fey et al. |
| 2007/0111327 A1 | 5/2007 | Jay |
| 2007/0249557 A1* | 10/2007 | Jay ...................... A61K 31/728 514/54 |
| 2008/0139458 A1 | 6/2008 | Jay et al. |
| 2008/0287369 A1 | 11/2008 | Jay |
| 2009/0068247 A1 | 3/2009 | Jay |

(Continued)

FOREIGN PATENT DOCUMENTS

| | | |
|---|---|---|
| CA | 2722913 C | 2/2018 |
| WO | WO-2000/064930 A2 | 11/2000 |

(Continued)

OTHER PUBLICATIONS

Anthony M. Reginato, Anti-Inflammatory Role of Lubricin/PRG4 in Monosodium Urate-crystal induced arthritis, Abstract 2260, ACR/ARHP Annual Meeting.*
Mechanisms of Carcinogenesis, Secition 3, 2008, International Agency for Research on Cancer, pp. 1-37.*
Timothy R. Orchard, Management of Arthritis in Patients with Inflammatory Bowel Disease, Gastroenterology & Hepatology vol. 8, Issue 5 May 2012, pp. 327-329.*
Al-Sharif et al., "Lubricin/Proteoglycan 4 binding to CD44 receptor: A mechanism of the suppression of proinflammatory cytokine-induced synoviocyte proliferation by Lubricin," Arthritis Rheumatol., 2015, 67( 6):1503-1513.
Aruffo, "CD44: One Ligand, Two Functions," J. Clin. Invest., Jul. 8, 2014: 98(10):2191-2192.

(Continued)

Primary Examiner — James H Alstrum-Acevedo
Assistant Examiner — Erinne R Dabkowski
(74) Attorney, Agent, or Firm — Goodwin Procter LLP

(57) ABSTRACT

Disclosed herein are methods of using PRG4 glycoprotein, also known as lubricin, to reduce, inhibit, or down-regulate pro-inflammatory pathways in patients at risk of or suffering from an inflammatory response or allergy symptom through CD44 antagonization, regulating pro-inflammatory cytokine production, inhibiting NF-κB translocation and/or facilitating removal of inflammation-inducing cellular or matrix debris or allergens.

19 Claims, 25 Drawing Sheets
Specification includes a Sequence Listing.

(56) References Cited

U.S. PATENT DOCUMENTS

| | | | |
|---|---|---|---|
| 2009/0104148 A1 | 4/2009 | Jay et al. | |
| 2009/0155200 A1 | 6/2009 | Jay | |
| 2009/0191287 A1 | 7/2009 | Johnson | |
| 2010/0092484 A1 | 4/2010 | Xu et al. | |
| 2010/0204087 A1 | 8/2010 | Jay | |
| 2012/0052077 A1* | 3/2012 | Truitt, III | A61K 9/0034 424/158.1 |
| 2013/0039865 A1 | 2/2013 | Truitt, III et al. | |
| 2013/0116186 A1 | 5/2013 | Jay | |
| 2013/0315973 A1 | 11/2013 | Jay | |
| 2014/0179611 A1 | 6/2014 | Jay | |
| 2016/0250286 A1 | 9/2016 | Schmidt | |
| 2016/0304572 A1 | 10/2016 | Schmidt et al. | |
| 2017/0246246 A1 | 8/2017 | Jay et al. | |
| 2017/0312335 A1 | 11/2017 | Truitt, III et al. | |

FOREIGN PATENT DOCUMENTS

| | | |
|---|---|---|
| WO | WO-2005/000331 A2 | 1/2005 |
| WO | WO-2005/102363 A2 | 11/2005 |
| WO | WO-2006/012492 A2 | 2/2006 |
| WO | WO-2006/060473 A2 | 6/2006 |
| WO | WO-2008/143816 A1 | 11/2008 |
| WO | WO-2009/137217 A2 | 11/2009 |
| WO | WO-2009/137602 A1 | 11/2009 |
| WO | WO-2009/137603 A1 | 11/2009 |
| WO | WO-2010/083239 A2 | 7/2010 |
| WO | WO-2010/135736 A2 | 11/2010 |
| WO | WO-2011/019963 A2 | 2/2011 |
| WO | WO-2011/050287 A1 | 4/2011 |
| WO | WO-2011/091000 A2 | 7/2011 |
| WO | WO-2014/115022 A1 | 7/2014 |
| WO | WO-2015/060935 A1 | 4/2015 |
| WO | WO-2015/061488 A1 | 4/2015 |
| WO | WO-2015/081121 A1 | 6/2015 |
| WO | WO-2016/123123 A1 | 8/2016 |
| WO | WO-2016/187414 A1 | 11/2016 |

OTHER PUBLICATIONS

Campo et al., "Molecular size hyaluronan differently modulates toll-like receptor-4 in LPS-induced inflammation in mouse chondrocytes," Biochimie, Oct. 20, 2009, 92:204-215.
Campo et al., "Small hyaluronan oligosaccharides induce inflammation by engaging both toll-like-4 and CD44 receptors in human chondrocytes," Biochemical Pharmacology, 2010, 80:480-490.
Cuff et al., "The adhesion receptor CD44 promotes atherosclerosis by mediating inflammatory cell recruitment and vascular cell activation," J. Clin. Invest., 2001, 108(7): 1031-1040.
Cutly et al., "The hyaluronan receptor (CD44) participates in the uptake and degradation of hyaluronan," J. Cell Biol., 1992, 116(4):1055-1062.
Estrella et al., "The glycosylation of human synovial lubricin: implications for its role in inflammation," Biochem. J., 2010, 429(2):359-67.
Flannery et al., "Prevention of cartilage degeneration in a rat mode of osteoarthritis by intraarticular treatment with recombinant Lubricin," Arthritis Rheum., 2009, 60:840-847.
Fleenor et al., "TGFβ2-Induced Changes in Human Trabecular Meshwork: Implications for Intraocular Pressure," Investigative Ophthalmology & Visual Science, 2006, 47(1): 226-234.
Fuchs et al., "Expression of the CD44 variant isoform 5 in the human osteoarthritic knee joint: correlation with radiological, histomorphological, and biochemical parameters," J. Orthopaedic Res., 2004, 22(4):774-80.
Grisar et al., "Expression Patterns of CD44 and CD44 Splice Variants in Patients with Rheumatoid Arthritis," Clin. Exp. Rheumatol., 2012, 30(1):64-72.
Harada et al., "CD44-dependent intracellular and extracellular catabolism of hyaluronic acid by hyaluronidase-1 and -2," J. Biol., Chem., 2007, 282(8):5597-607.
Iqbal et al., "Lubricin/Proteoglycan 4 binds to and regulates the activity of toll-like receptors in vitro," Sci. Rep., 2016, 6:18910. doi:10.1038/srep18910.
International Search Report for International Application No. PCT/US2016/014952 dated Jun. 15, 2016 (7 pages).
Jay et al., "Boundary lubrication by lubricin is mediated by O-linked beta(1-3)Gal-GalNAc oligosaccharides," Glucoconj. J., 2001, 18(10):807-15.
Jin et al., "Human synovial lubricin expresses Sialyl Lewis X determinant and Has L-selectin ligand activity," J. Biol. Chem., 2012, 287(43):35922-35933.
Johnson et al., "CD44 and its role in inflammation and inflammatory diseases," Inflammation & Allergy Drug Targets, 2009, 8(3):208-220.
Knepper et al., "Hypophosphorylation of aqueous humor sCD44 and primary open-angle glaucoma," Investigative Ophthalmology & Visual Science, 2005, 46(8):2829-2837.
Knudson et al., "CD44-mediated uptake and degradation of hyaluronan," Matrix Biol., 2002, 21:15-23.
Knudson et al., "CD44 and integrin matrix receptors participate in cartilage homeostasis," Cell Mol. Life Sci., 2002, 59:36-44.
Korolkova et al., "Characterization of serum cytokine profile in predominantly colonic inflammatory bowel disease to delineate ulcerative and crohn's colitides," Clinical Medicine Insights: Gastroenterology, 2015, 8:29-44.
Lacey et al., "Control of fibroblast-like synoviocyte proliferation by macrophage migration inhibitory factor," Arthritis & Rheumatism, 2003, 48(1):103-109.
Larché et al., "Immunological mechanisms of allergen-specific immunotherapy," Nat. Rev. Immunol., 2006, 6(10):761-71.
Leslie, "Inflammation's stop signals," Science, 2015, 347(6217):19-21.
Li et al., "Effect of CD44 suppression by antisense oligonucleotide and attachment of human trabecular meshwork cells to HA," Journal of Huazhong University of Science and Technology, 2004, 24(5):486-489.
Misra et al., "Hyaluronan, CD44, and cyclooxygenase-2 in colon cancer," Connective Tissue Research, 2008, 49:219-224.
Mokbel et al., "Erythropoietin and soluble CD44 levels in patients with primary open-angle glaucoma," Clinical & Experimental Ophthalmology, 2010, 38:560-565.
Murdoch et al., "Chronic inflammation and asthma," Mutation Research, 2010, 690: (16 pages).
Muto et al., "Engagement of CD44 by hyaluronan suppresses TLR4 signaling and the septic response to LPS," Molecular Immunology, 2009, 47:449-456.
Naor et al., "CD44 in rheumatoid arthritis," Arthritis Research & Therapy, 2003, 5(3):105-115.
Naor et al., "CD44: Structure, function, and associate with the malignant process," Adv. Cancer Res., 1997, 71:241-319.
Ohwada et al., "CD44 and hyaluronan engagement promotes dexamethasone resistance in human myeloma cells," Eur. J. Haematol., 2008, 80:245.
Rhee et al., "The secreted glycoprotein lubricin protects cartilage surfaces and inhibits synovial cell overgrowth," J. Clin. Invest., 2005, 115(3):622-631.
Rouschop et al., "Protection against renal ischemia reperfusion injury by CD44 disruption," American Society of Nephrology, 2005, 16:2034-2043.
Runnels et al., "PF-03475952: a potent and neutralizing fully human anti-CD44 antibody for therapeutic applications in inflammatory diseases," Advances in Therapy, 2010, 27(3):168-180.
Schmidt et al., "Transcription, translation, and function of lubricin, a boundary lubricant, at the ocular surface," Jama Ophthalmol., 2013, 131(6):766-76. doi:10.1001/jamaophthalmol.2013.2385.
Tibesku et al., "Expression of the matrix receptor CD44v5 on chondrocytes changes with osteoarthritis: an experimental investigation in the rabbit," Ann. Rheum. Dis., 2006, 65105-65108.
Waller et al., "Role of lubricin and boundary lubrication in the prevention of chondrocyte apoptosis," PNAS, 2013, 110(15):5852-5857.

(56) References Cited

OTHER PUBLICATIONS

Wang et al., "CD44 deficiency leads to enhanced neutrophil migration and lung injury *Escherichia coli* pneumonia in mice," Am. J. Pathology, 2002, 161:2219-2228.
Ward et al., "Airway wall remodelling: the influence of corticosteroids," Current Opinion in Allergy and Clinical Immunology, 2005, 5:43-48.
Wibulswas et al., "The CD44v7/8 epitope as a target to restrain proliferation of fibroblast-like synoviocytes in rheumatoid arthritis," Am. J. Pathology, 2000, 157:2037-2044.
Written Opinion of the International Searching Authority for International Application No. PCT/US2016/014952 dated Jun. 15, 2016 (6 pages).
Xu et al., "Involvement of CD44 in leukocyte trafficking at the blood-retinal barrier," Journal of Leukocyte Biology, 2002; 72(6):1133-41.
Zhang et al., "Expression of CD44 in articular cartilage is associated with disease severity in knee osteoarthritis," Mod. Rheumatol., 2013, 23(6):1186-91.
"Arthritis: Symptoms and Causes" published by the Mayo Clinic and available at <https://www.mayoclinic.org/diseases-conditions/arthritis/symptoms-causes/syc-20350772> and accessed on Sep. 17, 2020 (3 pages).
"*What is inflammatory bowel disease?*" published by the U.S. Centers for Disease control Mar. 22, 2018, and available at <https://www.cdc.gov/ibd/what-is-ibd.htm> accessed Sep. 16, 2020 (3 pages).

\* cited by examiner

Fig. 5A
Prg4 -/- Synoviocytes
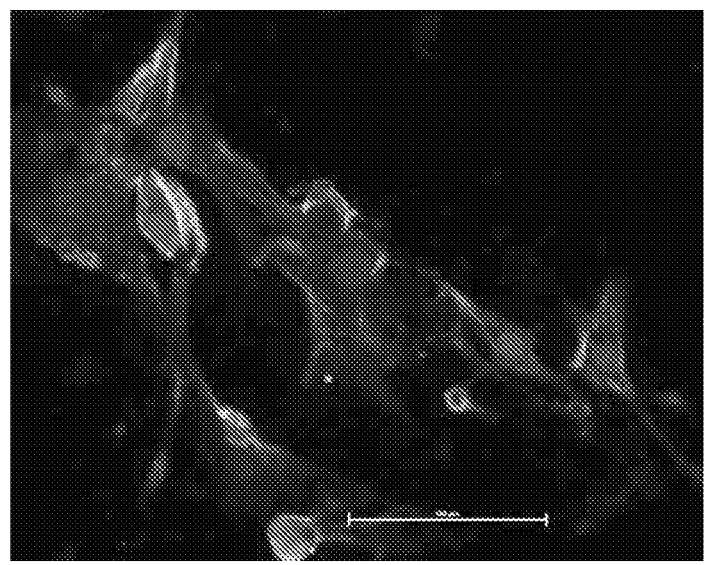
Prg4 +/+ Synoviocytes
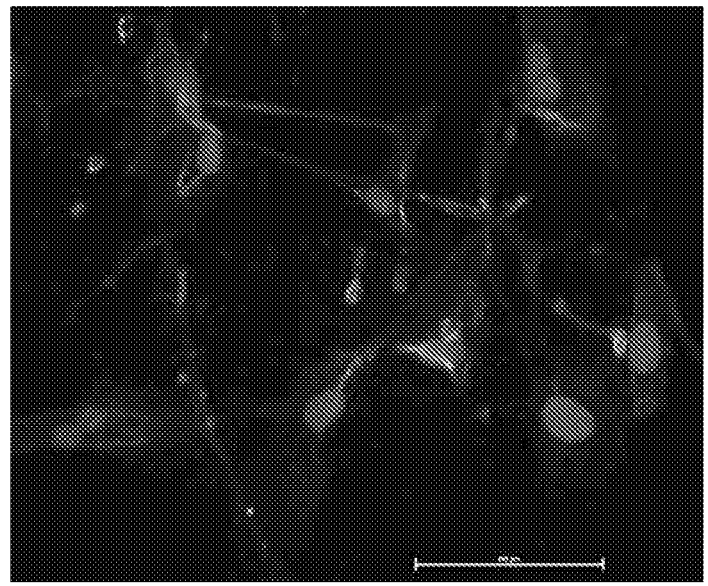

FIG. 6
SEQ ID NO: 1, LENGTH: 1404, ORGANISM: Homo sapiens, UniProt Accession No. Q92954:

MAWKTLPIYL LLLLSVFVIQ QVSSQDLSSC AGRCGEGYSR DATCNCDYNC QHYMECCPDF
KRVCTAELSC KGRCFESFER GRECDCDAQC KKYDKCCPDY ESFCAEVHNP TSPPSSKKAP
PPSGASQTIK STTKRSPKPP NKKKTKKVIE SEEITEEHSV SENQESSSSS SSSSSSSTIR
KIKSSKNSAA NRELQKKLKV KDNKKNRTKK KPTPKPPVVD EAGSGLDNGD FKVTTPDTST
TQHNKVSTSP KITTAKPINP RPSLPPNSDT SKETSLTVNK ETTVETKETT TTNKQTSTDG
KEKTTSAKET QSIEKTSAKD LAPTSKVLAK PTPKAETTTK GPALTTPKEP TPTTPKEPAS
TTPKEPTPTT IKSAPTTPKE PAPTTTKSAP TTPKEPAPTT TKEPAPTTPK EPAPTTTKEP
APTTTKSAPT TPKEPAPTTP KKPAPTTPKE PAPTTPKEPT PTTPKEPAPT TKEPAPTTPK
EPAPTAPKKP APTTPKEPAP TTPKEPAPTT TKEPSPTTPK EPAPTTTKSA PTTTKEPAPT
TTKSAPTTPK EPSPTTTKEP APTTPKEPAP TTPKKPAPTT PKEPAPTTPK EPAPTTTKKP
APTTPKEPAP TTPKETAPTT PKKLTPTTPE KLAPTTPEKP APTTPEELAP TTPEEPTPTT
PEEPAPTTPK AAAPNTPKEP APTTPKEPAP TTPKEPAPTT PKETAPTTPK GTAPTTLKEP
APTTPKKPAP KELAPTTTKE PTSTTCDKPA PTTPKGTAPT TPKEPAPTTP KEPAPTTPKG
TAPTTLKEPA PTTPKKPAPK ELAPTTTKGP TSTTSDKPAP TTPKETAPTT PKEPAPTTPK
KPAPTTPETP PPTTSEVSTP TTTKEPTTIH KSPDESTPEL SAEPTPKALE NSPKEPGVPT
TKTPAATKPE MTTTAKDKTT ERDLRTTPET TTAAPKMTKE TATTTEKTTE SKITATTTQV
TSTTTQDTTP FKITTLKTTT LAPKVTTTKK TITTTEIMNK PEETAKPKDR ATNSKATTPK
PQKPTKAPKK PTSTKKPKTM PRVRKPKTTP TPRKMTSTMP ELNPTSRIAE AMLQTTTRPN
QTPNSKLVEV NPKSEDAGGA EGETPHMLLR PHVFMPEVTP DMDYLPRVPN QGIIINPMLS
DETNICNGKP VDGLTTLRNG TLVAFRGHYF WMLSPFSPPS PARRITEVWG IPSPIDTVFT
RCNCEGKTFF FKDSQYWRFT NDIKDAGYPK PIFKGFGGLT GQIVAALSTA KYKNWPESVY
FFKRGGSIQQ YIYKQEPVQK CPGRRPALNY PVYGETTQVR RRRFERAIGP SQTHTIRIQY
SPARLAYQDK GVLHNEVKVS ILWRGLPNVV TSAISLPNIR KPDGYDYYAF SKDQYYNIDV
PSRTARAITT RSGQTLSKVW YNCP

FIG. 7A

SEQ ID NO: 2 LENGTH: 5041, TYPE: DNA, ORGANISM: Homo sapiens, GenBank Accession No. U70136.1:

GCGGCCGCGACTATTCGGTACCTGAAAACAACGATGGCATGGAAAACACTTCCCATTTACCTGT
TGTTGCTGCTGTCTGTTTTCGTGATTCAGCAAGTTTCATCTCAAGATTTATCAAGCTGTGCAGG
GAGATGTGGGGAAGGGTATTCTAGAGATGCCACCTGCAACTGTGATTATAACTGTCAACACTAC
ATGGAGTGCTGCCCTGATTTCAAGAGAGTCTGCACTGCGGAGCTTTCCTGTAAAGGCCGCTGCT
TTGAGTCCTTCGAGAGAGGGAGGGAGTGTGACTGCGACGCCCAATGTAAGAAGTATGACAAGTG
CTGTCCCGATTATGAGAGTTTCTGTGCAGAAGTGCATAATCCCACATCACCACCATCTTCAAAG
AAAGCACCTCCACCTTCAGGAGCATCTCAAACCATCAAATCAACAACCAAACGTTCACCCAAAC
CACCAAACAAGAAGAAGACTAAGAAAGTTATAGAATCAGAGGAAATAACAGAAGAACATTCTGT
TTCTGAAAATCAAGAGTCCTCCTCCTCCTCCTCCTCTTCCTCTTCTTCTTCAACAATTTGGAAA
ATCAAGTCTTCCAAAAATTCAGCTGCTAATAGAGAATTACAGAAGAAACTCAAAGTAAAAGATA
ACAAGAAGAACAGAACTAAAAAGAAACCTACCCCCAAACCACCAGTTGTAGATGAAGCTGGAAG
TGGATTGGACAATGGTGACTTCAAGGTCACAACTCCTGACACGTCTACCACCCAACACAATAAA
GTCAGCACATCTCCCAAGATCACAACAGCAAAACCAATAAATCCCAGACCCAGTCTTCCACCTA
ATTCTGATACATCTAAAGAGACGTCTTTGACAGTGAATAAAGAGACAACAGTTGAAACTAAAGA
AACTACTACAACAAATAAACAGACTTCAACTGATGGAAAAGAGAAGACTACTTCCGCTAAAGAG
ACACAAAGTATAGAGAAAACATCTGCTAAAGATTTAGCACCCACATCTAAAGTGCTGGCTAAAC
CTACACCCAAAGCTGAAACTACAACCAAAGGCCCTGCTCTCACCACTCCCAAGGAGCCCACGCC
CACCACTCCCAAGGAGCCTGCATCTACCACACCCAAAGAGCCCACACCTACCACCATCAAGTCT
GCACCCACCACCCCCAAGGAGCCTGCACCCACCACCACCAAGTCTGCACCCACCACTCCCAAGG
AGCCTGCACCCACCACCACCAAGGAGCCTGCACCCACCACTCCCAAGGAGCCTGCACCCACCAC
CACCAAGGAGCCTGCACCCACCACCACCAAGTCTGCACCCACCACTCCCAAGGAGCCTGCACCC
ACCACCCCAAGAAGCCTGCCCCAACTACCCCCAAGGAGCCTGCACCCACCACTCCCAAGGAGC
CTACACCCACCACTCCCAAGGAGCCTGCACCCACCACCAAGGAGCCTGCACCCACCACTCCCAA
AGAGCCTGCACCCACTGCCCCAAGAAGCCTGCCCCAACTACCCCCAAGGAGCCTGCACCCACC
ACTCCCAAGGAGCCTGCACCCACCACCACCAAGGAGCCTTCACCCACCACTCCCAAGGAGCCTG
CACCCACCACCACCAAGTCTGCACCCACCACTACCAAGGAGCCTGCACCCACCACTACCAAGTC

FIG. 7B

```
TGCACCCACCACTCCCAAGGAGCCTTCACCCACCACCACCAAGGAGCCTGCACCCACCACTCCC
AAGGAGCCTGCACCCACCACCCCCAAGAAGCCTGCCCCAACTACCCCCAAGGAGCCTGCACCCA
CCACTCCCAAGGAACCTGCACCCACCACCACCAAGAAGCCTGCACCCACCGCTCCCAAAGAGCC
TGCCCCAACTACCCCCAAGGAGACTGCACCCACCACCCCCAAGAAGCTCACGCCCACCACCCCC
GAGAAGCTCGCACCCACCACCCCTGAGAAGCCCGCACCCACCACCCCTGAGGAGCTCGCACCCA
CCACCCCTGAGGAGCCCACACCCACCACCCCTGAGGAGCCTGCTCCCACCACTCCCAAGGCAGC
GGCTCCCAACACCCCTAAGGAGCCTGCTCCAACTACCCCTAAGGAGCCTGCTCCAACTACCCCT
AAGGAGCCTGCTCCAACTACCCCTAAGGAGACTGCTCCAACTACCCCTAAAGGGACTGCTCCAA
CTACCCTCAAGGAACCTGCACCCACTACTCCCAAGAAGCCTGCCCCCAAGGAGCTTGCACCCAC
CACCACCAAGGAGCCCACATCCACCACCTCTGACAAGCCCGCTCCAACTACCCCTAAGGGGACT
GCTCCAACTACCCCTAAGGAGCCTGCTCCAACTACCCCTAAGGAGCCTGCTCCAACTACCCCTA
AGGGGACTGCTCCAACTACCCTCAAGGAACCTGCACCCACTACTCCCAAGAAGCCTGCCCCCAA
GGAGCTTGCACCCACCACCACCAAGGGGCCCACATCCACCACCTCTGACAAGCCTGCTCCAACT
ACACCTAAGGAGACTGCTCCAACTACCCCCAAGGAGCCTGCACCCACTACCCCCAAGAAGCCTG
CTCCAACTACTCCTGAGACACCTCCTCCAACCACTTCAGAGGTCTCTACTCCAACTACCACCAA
GGAGCCTACCACTATCCACAAAAGCCCTGATGAATCAACTCCTGAGCTTTCTGCAGAACCCACA
CCAAAAGCTCTTGAAAACAGTCCCAAGGAACCTGGTGTACCTACAACTAAGACTCCTGCAGCGA
CTAAACCTGAAATGACTACAACAGCTAAAGACAAGACAACAGAAAGAGACTTACGTACTACACC
TGAAACTACAACTGCTGCACCTAAGATGACAAAAGAGACAGCAACTACAACAGAAAAAACTACC
GAATCCAAAATAACAGCTACAACCACACAAGTAACATCTACCACAACTCAAGATACCACACCAT
TCAAAATTACTACTCTTAAAACAACTACTCTTGCACCCAAAGTAACTACAACAAAAAAGACAAT
TACTACCACTGAGATTATGAACAAACCTGAAGAAACAGCTAAACCAAAAGACAGAGCTACTAAT
TCTAAAGCGACAACTCCTAAACCTCAAAAGCCAACCAAAGCACCCAAAAAACCCACTTCTACCA
AAAAGCCAAAAACAATGCCTAGAGTGAGAAAACCAAAGACGACACCAACTCCCCGCAAGATGAC
ATCAACAATGCCAGAATTGAACCCTACCTCAAGAATAGCAGAAGCCATGCTCCAAACCACCACC
AGACCTAACCAAACTCCAAACTCCAAACTAGTTGAAGTAAATCCAAAGAGTGAAGATGCAGGTG
GTGCTGAAGGAGAAACACCTCATATGCTTCTCAGGCCCCATGTGTTCATGCCTGAAGTTACTCC
CGACATGGATTACTTACCGAGAGTACCCAATCAAGGCATTATCATCAATCCCATGCTTTCCGAT
GAGACCAATATATGCAATGGTAAGCCAGTAGATGGACTGACTACTTTGCGCAATGGGACATTAG
TTGCATTCCGAGGTCATTATTTCTGGATGCTAAGTCCATTCAGTCCACCATCTCCAGCTCGCAG
```

FIG. 7C

```
AATTACTGAAGTTTGGGGTATTCCTTCCCCCATTGATACTGTTTTACTAGGTGCAACTGTGAA
GGAAAAACTTTCTTCTTTAAGGATTCTCAGTACTGGCGTTTTACCAATGATATAAAAGATGCAG
GGTACCCCAAACCAATTTTCAAAGGATTTGGAGGACTAACTGGACAAATAGTGGCAGCGCTTTC
AACAGCTAAATATAAGAACTGGCCTGAATCTGTGTATTTTTTCAAGAGAGGTGGCAGCATTCAG
CAGTATATTTATAAACAGGAACCTGTACAGAAGTGCCCTGGAAGAAGGCCTGCTCTAAATTATC
CAGTGTATGGAGAAATGACACAGGTTAGGAGACGTCGCTTTGAACGTGCTATAGGACCTTCTCA
AACACACACCATCAGAATTCAATATTCACCTGCCAGACTGGCTTATCAAGACAAAGGTGTCCTT
CATAATGAAGTTAAAGTGAGTATACTGTGGAGAGGACTTCCAAATGTGGTTACCTCAGCTATAT
CACTGCCCAACATCAGAAAACCTGACGGCTATGATTACTATGCCTTTTCTAAAGATCAATACTA
TAACATTGATGTGCCTAGTAGAACAGCAAGAGCAATTACTACTCGTTCTGGGCAGACCTTATCC
AAAGTCTGGTACAACTGTCCTTAGACTGATGAGCAAAGGAGGAGTCAACTAATGAAGAAATGAA
TAATAAATTTTGACACTGAAAAACATTTTATTAATAAAGAATATTGACATGAGTATACCAGTTT
ATATATAAAAATGTTTTTAAACTTGACAATCATTACACTAAAACAGATTTGATAATCTTATTCA
CAGTTGTTATTGTTTACAGACCATTTAATTAATATTTCCTCTGTTTATTCCTCCTCTCCCTCCC
ATTGCATGGCTCACACCTGTAAAAGAAAAAGAATCAAATTGAATATATCTTTTAAGAATTCAA
AACTAGTGTATTCACTTACCCTAGTTCATTATAAAAAATATCTAGGCATTGTGGATATAAAACT
GTTGGGTATTCTACAACTTCAATGGAAATTATTACAAGCAGATTAATCCCTCTTTTTGTGACAC
AAGTACAATCTAAAAGTTATATTGGAAAACATGGAAATATTAAAATTTTACACTTTTACTAGCT
AAAACATAATCACAAAGCTTTATCGTGTTGTATAAAAAAATTAACAATATAATGGCAATAGGTA
GAGATACAACAAATGAATATAACACTATAACACTTCATATTTTCCAAATCTTAATTTGGATTTA
AGGAAGAAATCAATAAATATAAAATATAAGCACATATTTATTATATATCTAAGGTATACAAATC
TGTCTACATGAAGTTTACAGATTGGTAAATATCACCTGCTCAACATGTAATTATTTAATAAAAC
TTTGGAACATTAAAAAAATAAATTGGAGGCTTAAAAAAAAAAAAAAAAA
```

|      | Saline | LPS  | % Change |
|------|--------|------|----------|
| IL2  | 0      | 0    | 0.0      |
| IL4  | 1.06   | 1.4  | 32.1     |
| IL6  | 11     | 30   | 172.7    |
| IL8  | 206    | 560  | 171.8    |
| IL10 | 0.38   | 0.48 | 26.3     |
| VEGF | 21     | 46   | 119.0    |
| IFNg | 0.3    | 0.3  | 0.0      |
| TNFa | 128    | 327  | 155.5    |
| IL1a | 0.5    | 0.5  | 0.0      |
| IL1b | 1.46   | 1.7  | 16.4     |
| MCP1 | 79     | 91   | 15.2     |
| EGF  | 4.1    | 3.4  | -17.1    |

FIG. 8A

|  | Saline | Lubricin | % Change |
|---|---|---|---|
| IL2 | 0 | 0 | 0.0 |
| IL4 | 0.99 | 0.92 | -7.1 |
| IL6 | 89 | 68 | -23.6 |
| IL8 | 392 | 260 | -33.7 |
| IL10 | 2.78 | 2.14 | -23.0 |
| VEGF | 12.69 | 6.95 | -45.2 |
| IFNg | 0.22 | 0.29 | 31.8 |
| TNFa | 9.5 | 9 | -5.3 |
| IL1a | 0.25 | 0.25 | 0.0 |
| IL1b | 7.53 | 6.92 | -8.1 |
| MCP1 | 223 | 201 | -9.9 |
| EGF | 1.75 | 1.23 | -29.7 |

FIG. 9A

|  | LPS | LPS/Lubricin | % Change |
|---|---|---|---|
| IL2 | 0 | 0 | 0.0 |
| IL4 | 1.4 | 1.2 | -14.3 |
| IL6 | 30 | 29 | -3.3 |
| IL8 | 570 | 504 | -11.6 |
| IL10 | 0.48 | 0.32 | -33.3 |
| VEGF | 48 | 34 | -29.2 |
| IFNg | 0.52 | 0.52 | 0.0 |
| TNFa | 327 | 301 | -8.0 |
| IL1a | 0.62 | 0.62 | 0.0 |
| IL1b | 1.62 | 1.21 | -25.3 |
| MCP1 | 91 | 68 | -25.3 |
| EGF | 4.1 | 2 | -51.2 |

FIG. 10A

|  | TNFa | TNFa/Lubricin | % Change |
|---|---|---|---|
| IL2 | 0 | 0 | 0.0 |
| IL4 | 0.96 | 0.98 | 2.1 |
| IL6 | 95 | 68 | -28.4 |
| IL8 | 400 | 235 | -41.3 |
| IL10 | 10 | 9 | -10.0 |
| VEGF | 65 | 41 | -36.9 |
| IFNg | 1.4 | 0 | -100.0 |
| TNFa | 863 | 34 | -96.1 |
| IL1a | 0.33 | 0.41 | 24.2 |
| IL1b | 34 | 18 | -47.1 |
| MCP1 | 250 | 250 | 0.0 |
| EGF | 19 | 11 | -42.1 |

FIG. 11A

|  | TF | TF/Lubricin | % Change |
|---|---|---|---|
| IL2 | 0 | 0 | 0.0 |
| IL4 | 0.92 | 0.92 | 0.0 |
| IL6 | 71 | 68 | -4.2 |
| IL8 | 350 | 233 | -33.4 |
| IL10 | 1.26 | 2.1 | 66.7 |
| VEGF | 29 | 12 | -58.6 |
| IFNg | 0.3 | 0.3 | 0.0 |
| TNFa | 8.32 | 0.3 | -96.4 |
| IL1a | 0.33 | 0.23 | -30.3 |
| IL1b | 7.18 | 7.15 | -0.4 |
| MCP1 | 199 | 168 | -15.6 |
| EGF | 2.74 | 1.99 | -27.4 |

FIG. 12A

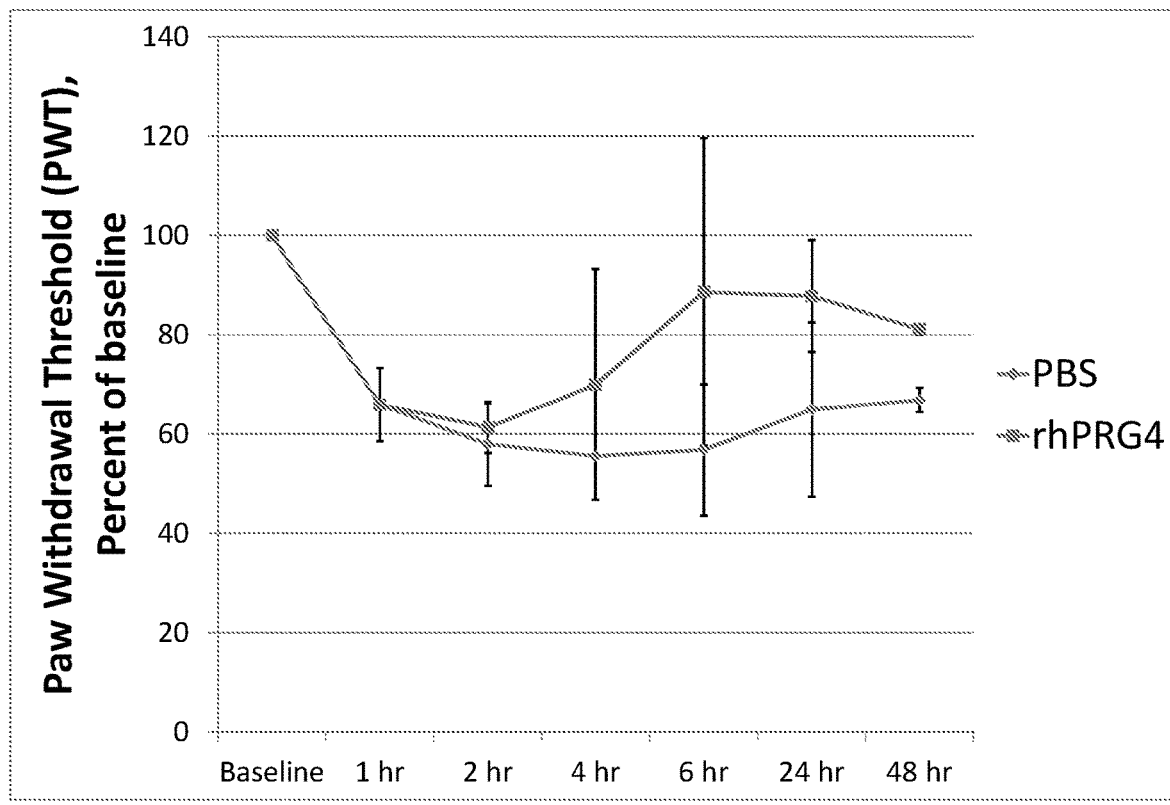

Fig. 15 Impact of intra-articular administration of recombinant human proteoglycan 4 (rhPRG4) on monosodium urate (MSU) crystal induced change in paw withdrawal pressure (PWT) in Male Lewis rats. Male Lewis rats (10 weeks ol; n=4) were injected with MSU suspension (50µl; 5 mg/ml; Invivogen, California) in their knee joints. At 1 hour following MSU injection, rat knee joints were treated with 50 µl phosphate buffered saline (PBS; n=2) or rhPRG4 (50µl; 2 mg/ml) (n=2). Paw withdrawal pressures were measured using an electronic Von Frey instrument, and data is present as percent change from baseline values.

USE OF PRG4 AS AN ANTI-INFLAMMATORY AGENT

CROSS REFERENCE TO RELATED APPLICATIONS

This application is a U.S. National Stage Application filed under 35 U.S.C. § 371 of International Patent Application No. PCT/US2016/014952, filed Jan. 26, 2016, which claims priority to and the benefit of U.S. provisional patent application No. 62/107,799 filed Jan. 26, 2015, and U.S. provisional patent application No. 62/273,059, filed Dec. 30, 2015, the disclosures of each of which are incorporated herein by reference in their entireties.

FIELD OF THE INVENTION

This invention relates to new uses of the human glycoprotein PRG4 or lubricin. More particularly, it relates to using PRG4 as an anti-inflammatory agent to reduce or inhibit inflammatory responses and to treat inflammatory conditions.

BACKGROUND

The proteoglycan 4 gene (PRG4) encodes megakaryocyte stimulating factor (MSF) as well as highly glycosylated differently splice variant and glycoforms of "superficial zone protein" also known as lubricin. Superficial zone protein was first localized at the surface of explant cartilage from the superficial zone and identified in conditioned medium. Lubricin was first isolated from synovial fluid and demonstrated lubricating ability in vitro similar to synovial fluid at a cartilage-glass interface and in a latex-glass interface. It was later identified as a product of synovial fibroblasts, and its lubricating ability was discovered to be dependent on O-linked β (1-3) Gal-GalNAc oligosaccharides within a large mucin like domain of 940 amino acids encoded by exon 6. Lubricin molecules are differentially glycosylated and several naturally occurring splice variants have been reported. They are collectively referred to herein as PRG4. PRG4 has been shown to be present inside the body at the surface of synovium, tendon, articular cartilage such as meniscus, and in the protective film of the eye, among other sites, and plays an important role in joint lubrication and synovial homeostasis.

Prior to Applicants' inventions, PRG4 had been appreciated as a protein with only mechanical properties, providing mechanical functionalities such as lubricating joints, tendons, cartilage, and acting as a mechanical barrier to inhibit intercellular interactions. However, as shown herein, Applicants have discovered that lubricin has properties that extend beyond its ability to provide boundary lubrication and anti-adhesion. In particular, Applicants have determined that PRG4 has anti-inflammatory properties due to its ability to act as a ligand or signaling molecule, participating in ligand receptor interactions to modulate, for example, CD44 activation, NF-κB translocation, and cytokine-mediated inflammation.

SUMMARY OF THE INVENTION

The current invention exploits the heretofore unknown anti-inflammatory properties of PRG4, also known as lubricin. Accordingly, the invention provides, for example, methods of inhibiting or reducing inflammatory responses and methods for treating inflammatory conditions. Underlying the discovery of PRG4's anti-inflammatory properties is the understanding of various putative mechanisms by which PRG4 achieves its anti-inflammatory effect. These mechanisms were discovered by Applicants who have determined that PRG4 binds CD44 receptors, enabling it to act as a CD44 receptor antagonist. As a result, PRG4 is able to down-regulate pro-inflammatory responses mediated by CD44 receptor signaling. The ability of PRG4 to affect CD44 signaling also has the effect of down-regulating translocation of NF-κB. Further, administration of PRG4 has been shown to inhibit production of a number of pro-inflammatory cytokines, as well as to modulate cellular responses and proliferation due to pro-inflammatory cytokine induction (e.g., TNF-a); a feature unique to PRG4 and not to other lubricants such as high molecular weight hyaluronic acid. PRG4 can therefore be used in a number of novel ways in therapeutic and prophylactic contexts to effect anti-inflammatory action via its effect on signaling pathways involved in producing an inflammatory response.

Accordingly, in one aspect, the invention provides a method of reducing or inhibiting an inflammatory response in a patient comprising administering PRG4 to the patient systemically or locally at a site that is non-cartilaginous, non-osseous, non-osteal, and non-articular, and is not the urinary bladder, cornea, or surface tissue of the oral cavity.

In one embodiment, the PRG4 is administered systemically to the patient, for example, by intravenous, intramuscular, subcutaneous, intraperitoneal, oral, rectal, buccal, or sublingual administration, or by inhalation.

In another embodiment of the invention, PRG4-containing compositions can be conveniently administered to patients by formulating PRG4 into a matrix/scaffold dosage form for injection/or placement within a location in a patient. Such a PRG4-containing composition may be in the form of a controlled release formulation that is capable of slowly releasing PRG4 at a location in the patient. Suitable matrix/scaffold dosage forms include, but are not limited to, biocompatible polymers, polymeric matrices, capsules, microcapsules, microparticles, diffusion devices and liposomes. Other such formulations of the present invention include liquids that, upon association with the matrix or upon administration to the patient, form a solid or a gel. In addition to such compositions being formulated to contain PRG4, such compositions may also be formulated to contain recombinantly engineered cells designed to express PRG4. The PRG4-containing compositions may be administered in any manner suitable to direct PRG4 to the location within a patient, including by direct injection or placement of a pre-formed PRG4 composition during an open surgery or during a laparoscopic or arthroscopic procedure.

In another embodiment, the PRG4 is administered locally to the patient, for example, topically or by injection. In some embodiments, the PRG4 is administered locally at a site selected from skin, kidney, lungs, liver, a wound such as a skin burn or surgical incision, thyroid, pancreas, spleen, thymus, ovary, testicle, uterus, adrenal gland, pituitary gland, hypothalamus, urethra, prostate, heart, artery or vessel, pericardial fluid, brain, stomach. Administration is also conducted in orifices including the rectum, nose, ear, pharynx, larynx, trachea. Other areas for administration include the tongue, posterior eye, or the site of a tumor. Administration is also performed in visci including the small intestine, large intestine, colon or esophagus, pharynx, larynx, trachea, tongue, posterior eye, or the site of a tumor. In some embodiments, the site of local administration is a site of inflammation or of an inflammatory response in the patient.

In another embodiment, PRG4 is administered systemically to a patient who suffers from an inflammatory condition selected from arthritis, osteoarthritis, psoriatic arthritis, rheumatoid arthritis, diabetic retinopathy, retinal inflammation, retinitis, Sjogren's syndrome, macular degeneration, gout, pseudogout, pericarditis, or uveitis.

In another embodiment, PRG4 is administered systemically or locally to a patient who suffers from an inflammatory condition selected from acne; acute organ failure; acute respiratory distress syndrome (ARDS); Addison's disease; allergic rhinitis; allograft rejection; alopecia areata; Alzheimer's disease; anaphylaxis; Appendicitis; asthma; atherosclerosis; atopic dermatitis; autoimmune disease including autoimmune alopecia; autoimmune hyperthyroidism; autoimmune hypopituatarism; autoimmune polyglandular disease; Behcet's disease; brain injury; bronchitis; cancer; cardiopulmonary bypass syndrome; cardiorenal syndrome; Celiac disease; chronic actinic dermatitis; chronic obstructive pulmonary disease (COPD); chronic renal failure; colitis; contact dermatitis; Crohn's disease; dermatomyositis; diabetes; eczema; emphysema; foreign body rejection; glaucoma; glomerulonephritis; gout; graft vs. host disease; Graves' Disease; Guillain-Barre syndrome; Hashimoto's thyroiditis; hay fever; hepatorenal syndrome; hypersensitivity or allergy; inclusion body myositis; infection due to viral, fungal, parasitic or microbial infiltration; inflammatory bowel disease; inflammatory kidney disease; injury due to thermal or chemical exposure or irradiation; irritable bowel syndrome; ischemia; lung inflammation; morphea; multiple sclerosis; mycosis fungoides; myocardial infarction; necrosis; non-infectious lung injury; pancreatitis; pernicious anemia; pneumonia; polymyositis; prostatitis; pseudogout; psoriasis; Pustulosis palmoplantaris; Pyoderma gangrenum; respiratory allergy; scleroderma; sepsis; serum sickness; Sezary's syndrome; skin allergy; stroke; systemic inflammatory response syndrome (SIRS); systemic lupus erythematosus; systemic sclerosis; T-cell mediated hypersensitivity diseases; transplant rejection; trauma including from a bullet wound, knife wound, automobile accident, fall, or combat; tuberculosis; ulcerative colitis; pericarditis; uticaria; and vitiligo.

In a further embodiment, the inflammatory response in the patient is associated with an inflammatory condition from which the patient suffers.

In a further embodiment, the PRG4 administered is recombinant human PRG4. In another embodiment, the PRG4 has the sequence of SEQ ID NO:1 minus the signal sequence. In one embodiment, PRG4 is administered in an amount insufficient to provide boundary lubrication in the patient. In another embodiment, PRG4 is administered in an amount ranging from 0.1 μg/kg-4,000 μg/kg or as a coating on a tissue surface applied from a PRG4 solution comprising, for example, a concentration of PRG4 between 10 μg/mL to about 2 mg/mL.

In one embodiment, the reduction or inhibition of the inflammatory response may be measured by the level of production of a pro-inflammatory cytokine in the patient. For example, in one embodiment, the pro-inflammatory cytokine is selected from the group consisting of IL-1α, IL-1β, IL-2, IL-3, IL-4, IL-5, IL-6, IL-7, IL-8, IL-9, IL-10, IL-11, IL-12, IL-12p70, IL-13, IL-14, IL-15, IL-16, IL-17, IL-17α, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, IL-36, TNF-α, TNF-β (lymphotoxin-α), lymphotoxin-β, CXC31L (Fractalkine), CXCL-8, CCL2, CCL3, CCL4, CCL5, CCL11, CXCL10, IFN-α, IFN-β, IFN-ε, IFN-κ, IFN-ω, IFN-γ, VEGF, MCP-1, MCP-3, EGF, GMCSF, CD40L, CD27L, CD30L, FASL, 4-1BBL, OX40L, TRAIL, FGF-2, GRO, MDC, Rantes, G-CSF, M-CSF, FGF-2, EPO, MCSF, MIP3α, MG-CSF, and GCSF.

In another aspect, the invention provides a method of reducing or inhibiting an inflammatory response in a patient having an inflammatory condition, the method comprising administering PRG4 to the patient. The inflammatory condition may be any of the conditions mentioned herein.

In one aspect, the invention provides a method of reducing or inhibiting an inflammatory response in a patient by administering PRG4 to the patient. Administration of PRG4 binds a CD44 receptor on a cell in the patient, reduces or inhibits the production of a pro-inflammatory cytokine in the patient, and/or reduces or inhibits the translocation of NF-κB in a cell in the patient and thereby reduces or inhibits the inflammatory response in the patient.

In another embodiment, the PRG4 is administered locally to said patient to cells at or about a non-cartilaginous tissue, a non-osteal tissue, a non-osseous tissue, and is not corneal, urinary bladder or oral cavity tissue, which is a site of inflammation in the patient.

In a further embodiment, the cell is a mast cell, a spleen cell, a lung cell, a renal cell, a brain cell, a cardiac cell, a hepatic cell, a cancer cell, a skin cell, an epithelial cell, an endothelial cell, leukocyte, lymphocyte, neutrophil, eosinophil, basophil, monocyte, macrophage, dendritic cell, fibroblast, muscle cell, urethral cell, vascular cell, nerve cell, pancreatic cell, gastric cell, intestinal cell, colon cell, rectal cell, gall bladder cell, stem cell, or thyroid cell.

In a further embodiment, PRG4 is administered to the patient systemically to contact a synoviocyte, a chondrocyte, an osteocyte, an osteoblast, an osteoclast, retinal cell, limbal cell, trabecular meshwork cell, corneal cell, conjunctival cell, an ocular cell, or an ophthalmic cell.

In yet another embodiment, whether PRG4 is administered locally or systemically, it is administered in an amount insufficient to provide boundary lubrication in the patient. For example, in one embodiment, the PRG4 is administered in amount ranging from 0.1 μg/kg-4,000 μg/kg.

In a further embodiment, administration of PRG4 reduces or inhibits a pro-inflammatory cytokine selected from the group consisting of IL-2, IL-4, IL-6, IL-8, IL-10, VEGF, IFN-γ, TNF-α, IL-1α, IL-1β, MCP-1, EGF, FGF-2, Fractalkine, IFN-α2, GRO, MCP-3, MDC, EPO, IL-13, IL-18, MCSF, MIP-3α, MG-CSF, IL-7, IL-5, G-CSF, Rantes, IL-17α, or IL-12p70.

In another aspect, the invention provides a method of inhibiting binding of an activating ligand to CD44 present on a surface. The method comprises exposing the surface to PRG4 at a concentration sufficient to bind CD44 and to inhibit binding of the ligand. According to one embodiment, PRG4 is present at the surface in an amount sufficient to bind CD44 but insufficient to provide boundary lubrication. In another embodiment, the surface is a mammalian cell membrane while in another embodiment the surface is in a surface plasmon resonance detector. In yet another embodiment, the PRG4 is rhPRG4 (recombinant human PRG4) or nhPRG4 (native human PRG4).

In a further embodiment, the surface is in a human subject. In another embodiment, the PRG4 is administered systemically. In another embodiment, the PRG4 is administered topically to a patient. In yet another embodiment, the PRG4, for example rhPRG4, is administered to a human subject in amount ranging from 0.1 μg/kg-4,000 μg/kg. In another embodiment, the PRG4, for example, rhPRG4, is administered in an amount of 0.1 μg/mL to 30 mg/mL in small volumes of 1-100 μL per dose. In another embodiment, the PRG4 is administered in an amount of 10 μg/mL to 4 mg/mL in volumes of 100 μL-4 L per dose, for instance as an enema.

In one embodiment, when the surface is in a human subject, the human suffers from a bone metabolic disorder and exposing the receptor to PRG4 reduces or inhibits osteoclast differentiation. In a further embodiment, the human suffers from an inflammatory condition. Exemplary inflammatory conditions have been listed herein above. In one embodiment, exposing the receptor to PRG4, for example, rhPRG4 reduces inflammation or the level of a pro-inflammatory cytokine in the location of the inflammatory condition.

According to one embodiment, the cell is a synoviocyte, a mast cell, a spleen cell, a lung cell, a renal cell, a brain cell, a cardiac cell, an eye cell, a hepatic cell, a cancer cell, a skin cell, an epithelial cell, or an endothelial cell. In a further embodiment, the cell is a synoviocyte of a subject with rheumatoid arthritis, a pancreatic cell of a diabetic, a lung cell of an asthmatic, an ocular cell of a subject with an eye infection, burn or other irritation; a bronchiolar or alveolar epithelial cell of a subject with tuberculosis or another lung infection or injury or condition; a lung cell of a cystic fibrosis subject; a lower intestinal epithelial cell of a person with colitis or Crohn's disease; a skin cell of a subject with psoriasis, a skin cell of a subject with acne; a skin cell of a subject following treatment with laser ablation, or an endothelial cell of subject with sepsis. In yet another embodiment, the cell is a T-cell, while in a further embodiment, the cell is a lymphocyte, neutrophil, fibroblast, cancer cell, macrophage, dendritic cell, monocyte, eosinophil, or endothelial cell.

According to one embodiment, exposing a surface to PRG4, for example, rhPRG4, antagonizes a pro-inflammatory ligand of CD44. In one embodiment, the ligand is hyaluronan (HA), a hyaluronan serum-derived hyaluronan-associated protein complex (HA-SHAP), or a matrix metalloproteinase (e.g., MMP-9). In another embodiment, the ligand is hemopexin, EMMPRIN, somatomedin-B, osteopontin, OKT3, or a complement related protein such as C3a, CD3, CD46.

In another aspect, the invention provides a method of reducing or inhibiting pro-inflammatory cytokine levels in blood, for example, in a human subject. The method comprises the step of administering PRG4 systemically in an amount sufficient to reduce or inhibit pro-inflammatory cytokine levels. Exemplary proinflammatory cytokines include IL-2, IL-4, IL-6, IL-8, IL-10, VEGF, IFN-γ, TNF-α, IL1-α, IL-1-β, MCP-1, EGF, FGF-2, fractalkine, IFN-α2, GRO, MCP-3, MDC, EPO, IL-13, IL-18, MCSF, MIP-3α, MG-CSF, IL-7, IL-5, G-CSF, Rantes, IL-17α, or IL-12p70.

In a further aspect, the invention provides a method of inhibiting NF-κB translocation in a cell. The method comprises the step of contacting a cell containing NF-κB with PRG4, wherein PRG4 binds to a cell surface receptor to inhibit activation of the NF-κB signaling pathway. In a further embodiment, PRG4 inhibits a TNF-α receptor or an IL-1 receptor on the cell surface.

In yet another embodiment, the cell is in a human when contacted with PRG4. In a further embodiment, the cell is a synoviocyte, chondrocyte, or osteocyte, while in yet another embodiment, the cell is a spleen cell, a lung cell, a renal cell, a brain cell, a cardiac cell, a brain cell, a hepatic cell, an epithelial cell or an endothelial cell.

BRIEF DESCRIPTION OF THE DRAWINGS

FIG. 1A depicts binding of rhPRG4, HMW HA, MMW HA and vitronectin to CD44-IgG1Fc and using IgG1 Fc. The star (*) indicates that the 450 nm absorbance in the CD44-IgG1 Fc wells were statistically significantly higher ($p<0.001$) than the IgG1 Fc wells for rhPRG4, HMW HA and MMW HA. FIG. 1B shows the concentration-dependent CD44 binding of rhPRG4, HMW HA and MMW HA. CD44 binding to rhPRG4 was significantly higher than to HMW HA or MMW HA ($p<0.001$). The double stars (**) indicate that CD44 binding to rhPRG4 was significantly higher than to MMW HA ($p<0.001$). FIG. 1C depicts the competition between rhPRG4 (5 μg/mL) and either HMW HA or MMW HA (0.01 μg/mL to 50 μg/mL) on binding to CD44 coated on 96-well ELISA plates. The star (*) indicates the percentage CD44 binding in HMW HA+rhPRG4 wells was significantly lower than rhPRG4 wells ($p<0.05$); (**) indicates the percentage CD44 binding in MMW HA+rhPRG4 wells was significantly lower than rhPRG4 wells ($p<0.05$).

FIG. 2A is a sensogram depicting the concentration-dependent association and dissociation of rhPRG4 (300 μg/mL to 50 μg/mL) to immobilized CD44-IgG$_1$Fc. Dashed line curves represent the binding curves of rhPRG4 to CD44 chimeric protein and the black lines represent the fitted 1:1 binding model. FIG. 2B is a plot showing the relative response-HMW HA binding vs. relative response-rhPRG4 binding. Competition between rhPRG4 and HMW HA on binding to immobilized CD44-IgG$_1$Fc. rhPRG4 was injected at 300 (1), 250 (2), 200 (3), 150 (4), 100 (5), 50 (6) and 0 (7) μg/mL. Following dissociation of rhPRG4, HMW HA was injected at 50 μg/mL. As the concentration of rhPRG4 increased, subsequent HMW HA binding to CD44 decreased.

FIG. 3A is a bar graph depicting binding of rhPRG4, sialidase-A digested rhPRG4, O-glycosidase digested rhPRG4 and sialidase-A+O-glycosidase digested rhPRG4 to CD44. The 450 nm absorbance values across different groups were normalized to the absorbance values in the undigested rhPRG4 group. The (*) indicates that CD44 binding in the sialidase A-digested and O-glycosidase-digested rhPRG4 was significantly higher compared to undigested rhPRG4 ($p<0.01$). (**) indicates that CD44 binding in the Sialidase-A+O-Glycosidase digested rhPRG4 was significantly higher compared to sialidase-A digested, O-glycosidase-digested and undigested rhPRG4 ($p<0.01$). FIG. 3B is a photograph of an SDS-PAGE of rhPRG4, sialidase-A digested rhPRG4, O-glycosidase digested rhPRG4 and a combination of sialidase-A and O-glycosidase digested rhPRG4. The gel was stained overnight with Commassie Blue. Digestion with sialidase-A and O-glycosidase resulted in reducing the apparent molecular weight of rhPRG4.

FIG. 4A is a bar graph depicting the inhibition of cytokine induced RA-FLS proliferation by rhPRG4 and HMW HA. (#) indicates that cytokine stimulated RA-FLS had a significantly ($p<0.001$) higher absorbance than untreated cells. (*) indicates that rhPRG4 (40 and 80 µg/mL) or HMW HA (40 and 80 µg/mL) treatment of IL-1β stimulated RA-FLS significantly ($p<0.05$) reduced cellular proliferation compared to untreated IL-1β stimulated cells. (**) indicates that rhPRG4 (20, 40 and 80 µg/mL) treatment significantly ($p<0.05$) reduced cell proliferation compared to untreated TNF-α stimulated cells. FIG. 4B is a bar graph depicting the inhibition of cytokine induced RA-FLS proliferation by rhPRG4 and HMW HA in the presence and absence of IM7, a CD44-specific antibody. (#) indicates that cytokine stimulated RA-FLS had a significantly ($p<0.001$) higher absorbance than untreated cells. (*) indicates that rhPRG4 or HMW HA treatment had a significantly lower cell proliferation compared to untreated IL-1β or (rhPRG4 or HMW HA)+IM7 treatment ($p<0.05$). (**) indicates that rhPRG4 treatment had a significantly ($p<0.05$) lower cell proliferation compared to untreated TNF-α or rhPRG4+IM7 treatment ($p<0.05$), a result that was not replicated by the HMW HA.

FIGS. 5A-C depict the impact of pro-inflammatory cytokines on Prg4−/− and Prg4+/+ synoviocyte proliferation and effect of rhPRG4. FIG. 5A shows fluorescence micrographs of Prg4−/− and Prg4+/+ synoviocytes immunocytostained using anti-CD44 antibody (IM7) (Green) and DAPI (blue). Enhanced green fluorescence in Prg4−/− synoviocytes indicates increased CD44 localization compared to Prg4+/+ synoviocytes. FIG. 5B shows a bar graph depicting cytokine induced proliferation of Prg4−/− and Prg4+/+ synoviocytes. IL-1β induced proliferation of Prg4−/− synoviocytes was significantly higher than IL-1β induced proliferation of Prg4+/+ synoviocytes ($p<0.001$) and TNF-α induced proliferation of Prg4−/− synoviocytes ($p=0.002$). TNF-α induced proliferation of Prg4−/− synoviocytes was significantly higher than TNF-α induced proliferation of Prg4+/+ synoviocytes ($p<0.001$). FIG. 5C shows a bar graph of the impact of rhPRG4 treatment on cytokine induced Prg4−/− synoviocyte proliferation in the presence and absence of IM7. (#) indicates cytokine stimulated Prg4−/− synoviocytes had a significantly higher absorbance compared to untreated cells ($p<0.001$). (*) indicates rhPRG4 treatment of IL-1β stimulated Prg4−/− synoviocytes significantly reduced cell proliferation compared to untreated IL-1β or rhPRG4+IM7 treatment ($p<0.001$). (**) indicates rhPRG4 treatment of TNF-α stimulated Prg4−/− synoviocytes significantly reduced cell proliferation compared to untreated TNF-α or rhPRG4+IM7 treatment ($p<0.001$).

FIG. 6 is the amino acid sequence of full length (non-truncated) human PRG4 (SEQ ID NO:1: 1404 residues). Residues 1-24 (shown in bold) represent the signal sequence and residues 25-1404 represent the mature sequence of human PRG4. The glycoprotein does not require the lead sequence in its active form.

FIGS. 7A-C provide the nucleic acid sequence for the PRG4 gene (SEQ ID NO:2) encoding the full length 1404 AA human PRG4 protein.

FIGS. 8A-B show how administration of lipopolysaccharide up-regulates production of inflammatory cytokines. FIG. 8A is a table showing the measured level of each cytokine present in whole blood samples after challenge with saline (control) and after challenge with lipopolysaccharide. The concentrations of the various cytokines represent a mean of duplicate determination and are expressed in pg/mL (ng/L). The percent change is shown in the bar graph in FIG. 8B and is based on the comparison of the LPS stimulated results with that of the saline control.

FIGS. 9A-B show how administration of lubricin down-regulates production of inflammatory cytokines. FIG. 9A is a table showing the measured level of each cytokine present in whole blood samples after challenge with saline (control) and after challenge with lubricin. The concentrations of the various cytokines represent a mean of duplicate determination and are expressed in pg/mL (ng/L). The percent change for each individual cytokine is based on the comparison of the lubricin supplemented sample with that of the saline control and is shown in the bar graph in FIG. 9B.

FIGS. 10A-B show how administration of lubricin inhibits LPS mediated inflammatory cytokine generation. FIG. 10A is a table showing the measured level of each cytokine present in whole blood samples after challenge with LPS and LPS with lubricin. The concentrations of the various cytokines represent a mean of duplicate determination and are expressed in pg/mL (ng/L). The percent change for each of the individual cytokines is based on the comparison of the LPS alone and LPS supplemented with lubricin and is shown in the bar graph in FIG. 10B.

FIGS. 11A-B show how administration of lubricin inhibits TNF-α mediated inflammatory cytokine generation. FIG. 11A is a table showing the measured level of each cytokine present in whole blood samples after challenge with TNF-α and with lubricin and TNF-α. The concentrations of the various cytokines represent a mean of duplicate determination and are expressed in pg/mL (ng/L). The percent change for each of the individual cytokines is based on the comparison of the TNF-α alone and TNF-α supplemented with lubricin and is shown in the bar graph in FIG. 11B.

FIGS. 12A-B show how administration of lubricin inhibits tissue factor (TF) mediated inflammatory cytokine generation. FIG. 12A is a table showing the measured level of each cytokine present in whole blood samples after challenge with TF and with lubricin and TF. The concentrations of the various cytokines represent a mean of duplicate determination and are expressed in pg/mL (ng/L). The percent change for each of the individual cytokines is based on the comparison of the TF alone and TF supplemented with lubricin and is shown in the bar graph in FIG. 12B.

FIG. 14A shows FGF-2 concentrations while FIG. 14B shows IL-1Ra concentrations.

FIG. 15 demonstrates the impact of intra-articular administration of recombinant human proteoglycan 4 (rhPRG4) on monosodium urate (MSU) crystal induced change in paw withdrawal pressure (PWT) in Male Lewis rats. Paw withdrawal pressures were measured using an electronic Von Frey instrument, and data is present as percent change from baseline values.

DETAILED DESCRIPTION

Figure 1A:
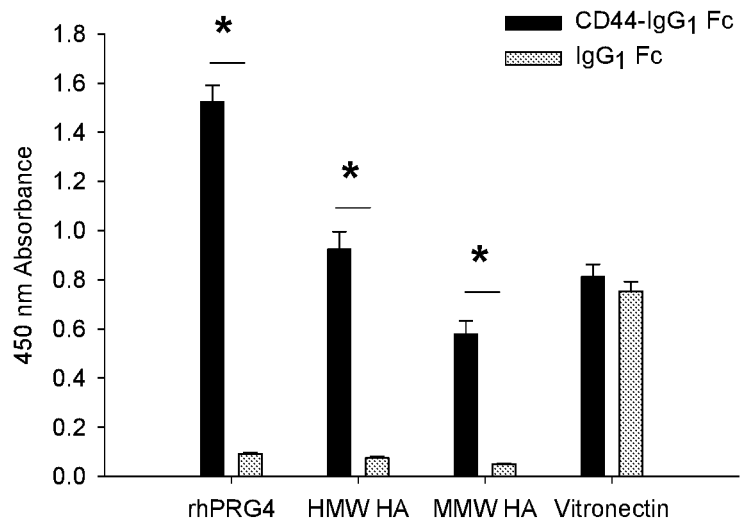
FIGS. 1A-C are bar graphs presenting data demonstrating the binding of recombinant human proteoglycan 4 (rh-PRG4), high-molecular weight hyaluronic acid (HMW HA), and medium molecular weight hyaluronic acid (MMW HA) to recombinant human CD44 receptor as detected by TMB-ELISA at 450 nm. Data represents the average of 4 independent experiments with triplicate wells per group.

The invention disclosed herein is based on the discovery of the previously unknown and unappreciated anti-inflammatory properties of PRG4, also known as lubricin. The invention exploits the anti-inflammatory properties of PRG4 to provide a number of new therapeutic and prophylactic uses for PRG4. For example, the invention provides methods of inhibiting or reducing inflammatory responses and methods for treating inflammatory conditions.

While an inflammatory response is necessary for fighting infection and disease, many inflammatory conditions are the result of excessive, rogue or unwarranted inflammatory responses. Such is the case, for example, with autoimmune conditions, allergic reactions, chronic inflammatory conditions, and sepsis. While in some situations, inflammation may create chronic pain or discomfort and lead to low quality of life, in other situations, inflammation may be life threating as is the case with sepsis. Accordingly, the discovery that PRG4 can be used as an anti-inflammatory agent, for example, to mitigate inflammation when it is excessive, rogue or unwarranted provides promise for treating chronic or acute inflammatory conditions and regulating, reducing or inhibiting the levels of associated inflammation.

PRG4 Protein

PRG4, also referred to as lubricin, is a lubricating polypeptide, which in humans is expressed from the megakaryocyte stimulating factor (MSF) gene, also known as PRG4 (see NCBI Accession Number AK131434-U70136). Lubricin is a ubiquitous, endogenous glycoprotein that coats the articulating surfaces of the body. Lubricin is highly surface active molecule (e.g., holds onto water), that acts primarily as a potent cytoprotective, anti-adhesive and boundary lubricant. The molecule has a long, central mucin-like domain located between terminal protein domains that allow the molecule to adhere and protect tissue surfaces. Its natural form, in all mammals investigated, contains multiple repeats of an amino acid sequence which is at least 50% identical to KEPAPTT (SEQ ID NO:3). Natural lubricin typically comprises multiple redundant forms of this repeat, which typically includes proline and threonine residues, with at least one threonine being glycosylated in most repeats. The threonine anchored O-linked sugar side chains are critical for lubricin's boundary lubricating function. The side chain moiety typically is a β(1-3)Gal-GalNAc moiety, with the β(1-3)Gal-GalNAc typically capped with sialic acid or N-acetylneuraminic acid. The polypeptide also contains N-linked oligosaccharides. The gene encoding naturally-occurring full length lubricin contains 12 exons, and the naturally-occurring MSF gene product contains 1,404 amino acids (including the secretion sequence) with multiple polypeptide sequence homologies to vitronectin including hemopexin-like and somatomedin-like regions. Centrally-located exon 6 contains 940 residues. Exon 6 encodes the repeat rich, O-glycosylated mucin-like domain.

The amino acid sequence of the protein backbone of lubricin may differ depending on alternative splicing of exons of the human MSF gene. This robustness against heterogeneity was exemplified when researchers created a recombinant form of lubricin missing 474 amino acids from the central mucin domain, yet still achieved reasonable, although muted, lubrication (Flannery et al., Arthritis Rheum 2009; 60(3):840-7). PRG4 has been shown to exist not only as a monomer but also as a dimer and multimer disulfide-bonded through the conserved cysteine-rich domains at both N- and C-termini. Lubris, LLC has developed a full-length recombinant form of human lubricin. The molecule is expressed using the Selexis Chinese hamster ovary cell line (CHO-M), with a final apparent molecular weight of 450-600 kDa, with polydisperse multimers frequently measuring at 1,000 kDa or more, all as estimated by comparison to molecular weight standards on SDS tris-acetate 3-8% polyacrylamide gels. Of the total glycosylations, about half comprise two sugar units (GalNAc-Gal), and half three sugar units (GalNAc-Gal-Sialic acid). This method of recombinant human PRG4 production is disclosed in International Patent Application No. PCT/US014/061827.

Any one or more of various native and recombinant PRG4 proteins and isoforms may be utilized in the various embodiments described herein. For instance, U.S. Pat. Nos. 6,433,142; 6,743,774; 6,960,562; 7,030,223, and 7,361,738 disclose how to make various forms of human PRG4 expression product, each of which is incorporated herein by reference. Preferred for use in the practice of the invention is full length, glycosylated, recombinant PRG4, or lubricin, expressed from CHO cells. This protein comprises 1,404 amino acids (see FIG. 6; SEQ ID NO:1) including a central exon comprising repeats of the sequence KEPAPTT (SEQ ID NO: 3) variously glycosylated with O-linked β (1-3) Gal-GalNAc oligosaccharides, and including N and C-terminal sequences with homology to vitronectin. The molecule is polydisperse with the glycosylation pattern of individual molecules varying, and can comprise monomeric, dimeric, and multimeric species.

As used herein, the term "PRG4" is used interchangeably with the term "lubricin." Broadly, these terms refer to any functional isolated or purified native or recombinant PRG4 proteins, homologs, functional fragments, isoforms, and/or mutants thereof. All useful molecules comprise the sequence encoded by exon 6, or homologs or truncated versions thereof, for example, versions with fewer repeats within this central mucin-like KEPAPTT-repeat domain, preferably together with O-linked glycosylation. All useful molecules also comprise at least the biological active portions of the sequences encoded by exons 1-5 and 7-12, i.e., sequences responsible for imparting to the molecule its affinity for ECM and endothelial surfaces. In certain embodiments, a preferred PRG4 protein has an average molar mass of between 50 kDa and 500 kDa, preferably between 224 to 467 kDa, comprising one or more biological active portions of the PRG4 protein, or functional fragments, such as a lubricating fragment, or a homolog thereof. In a more preferred embodiment, a PRG4 protein comprises monomers of average molar mass of between 220 kDa to about 280 kDa.

Methods for isolation, purification, and recombinant expression of a proteins such as PRG4 protein are well known in the art. In certain embodiments, the method starts with cloning and isolating mRNA and cDNA encoding PRG4 proteins or isoforms using standard molecular biology techniques, such as PCR or RT-PCR. The isolated cDNA encoding the PRG4 protein or isoform is then cloned into an expression vector, and expressed in a host cell for producing recombinant PRG4 protein, and isolated from the cell culture supernatant. A method for production of recombinant human PRG4 is provided in International Patent Application No. PCT/US014/061827.

The function of PRG4 heretofore has been almost entirely associated with reduction of friction and prevention of wear between articulating joints and lubrication of interfacing tissues such as between the surface of the eye and eyelid. The functional importance of PRG4 in joint maintenance has been shown by mutations that cause the camptodactyly-arthropathy-coxa vara-pericarditis (CACP) disease syndrome in humans. CACP is manifest by camptodactyly, noninflammatory arthropathy, and hypertrophic synovitis, with coxa vara deformity, pericarditis, and pleural effusion. Also, in PRG4-null mice, cartilage deterioration and subsequent joint failure were observed. Therefore, PRG4 expression is a necessary component of healthy synovial joints. However, use of a systemic boundary lubricant such as PRG4 protein as an anti-inflammatory agent as described in the present invention to Applicants' knowledge has not been previously suggested.

PRG4 as an Anti-Inflammatory Agent

The discovery of PRG4's anti-inflammatory properties is based on the observation of various putative mechanisms by which PRG4 achieves its anti-inflammatory effect. One mechanism by which PRG4 produces an anti-inflammatory effect involves CD44. Applicants discovered that PRG4 binds CD44 receptors, enabling it to act as a CD44 receptor antagonist. As a result, PRG4 is able to down-regulate pro-inflammatory responses mediated by CD44 receptor signaling.

CD44 is a glycoprotein and a major cell surface receptor with various isoforms generated by alternative splicing and glycosylation that plays a major role in inflammation. (Cutly et al., *J Cell Biol* 1992; 116(4):1055-62) and is involved in a variety of cell-cell interactions, tumor metastasis, and lymphocyte activation. CD44 is expressed in a large number of mammalian cell types and its levels of expression vary between cell types and their activation state. Cancerous or neoplastic cells may also express CD44 and the presence of CD44 on such cells is indicative of its involvement in the regulation and metastasis of cancer. In humans, CD44 is encoded by the CD44 gene on chromosome 1. Signaling through CD44 induces T cell proliferation and IL-2 production, dose-response-dependent enhancement of NK cytotoxic activity, and macrophage production of cytokines and chemokines, as well as other functions.

A well-established ligand for CD44 is high molecular weight hyaluronan (HMW HA), where HMW HA binds to an extracellular motif in CD44 with homology to other HA-binding proteins resulting in subsequent intracellular uptake of HMW HA. (Knudson et al., *Matrix Biol* 2002; 21(1):15-23; Harada et al., *J Biol Chem* 2007; 282(8):5597-607; Tibesku et al., *Ann Rheum Dis* 2006; 65(1):105-8). In experimental models of osteoarthritis, chondrocyte CD44 expression is increased with disease progression and the expression of CD44 in articular cartilage may correlate with disease severity in humans. (Fuchs et al., *J Orthop Res* 2004; 22(4):774-80; Zhang et al., *Mod Rheumatol* 2013; 23(6): 1186-91). HA/CD44 interactions are prevalent in a variety of disease states. Carcinomas arising from colon epithelia tend to develop in an HA-rich microenvironment, wherein CD44 receptors on epithelial tumor cells activate a tyrosine kinase mediated cell survival pathway, leading to unchecked cell division and proliferation (Misra S et al. *Connect Tissue Res.* 2008; 49(3):219-24). CD44 on endothelial cells acts to present HA to CD44 on antigen-activated T lymphocytes, thereby mediating a rolling interacting that directs leukocyte recruitment of inflammatory sites (Johnson P et al. *Inflamm Allergy Drug Targets.* 2009 July; 8(3):208-20), e.g., in a renal ischemia reperfusion model, rapid CD44 upregulation on renal capillary endothelial cells mediated neutrophil recruitment and degraded renal function and morphology, whereas CD44 deficiency reduced the influx of neutrophils independent of the level of expressed chemotactic factors (Rouschop K M A et al. *J Am Soc Nephrol* 2005; 16:2034-43).

The role of CD44 can vary by cell type, inflammatory state and be site-specific. For instance, CD44 deficiency was found to enhance inflammation in *E. coli*-induced but not *S. pneumonia*-induced pneumonia, suggesting that CD44-HA dependent interactions may limit rather than increase the inflammatory response to *E. coli* (Wang Q et al. *Am J Pathol.* 2002 December; 161(6):2219-28).

Other CD44 ligands include extracellular matrix components e.g. collagens, fibronectin and laminin (Naor et al., *Adv Cancer Res* 1997; 71:241-319; Knudson et al., *Cell Mol. Life Sci.* 2002; 59:36-44), matrix metalloproteinase-9, the HA-serum-derived hyaluronan associated protein complex (HA-SHAP), hemopexin, EMMPRIN, somatomedin-B, osteopontin, OKT3, or complement related proteins (such as C3a, CD3, CD46).

As shown by the data presented in Example 1 below, the lubricin-CD44 interaction shows that this glycoprotein has functions beyond its boundary lubricating and mechanical properties. In fact, Examples 1A-D show that lubricin acts as a ligand, binding CD44. Accordingly, because lubricin binds CD44, lubricin may be used as a CD44 antagonist to prevent binding to CD44 of ligands, such as hyaluronic acid, that result in pro-inflammatory signaling by CD44. Further, because of these demonstrated anti-inflammatory properties, lubricin is indicated as an agent for treating inflammatory conditions, reducing or inhibiting inflammation and reducing or inhibiting an inflammatory response.

Another mechanism discovered by Applicants through which PRG4 provides an anti-inflammatory effect is through down-regulating translocation of NF-κB. NF-κB is a protein complex that controls transcription of DNA, is critical to cell survival, and plays a key role in regulating the immune response to infection, and in turn regulating cytokine production. NF-κB is generally located in the cytoplasm of almost all animal cell types, and when induced by a stimulus, such as stress, cytokines, free radicals, ultraviolet irradiation, oxidized LDL, and bacterial or viral antigens, migrates to the nucleus. Incorrect regulation of NF-κB has been linked to cancer, inflammatory and autoimmune diseases, septic shock, viral infection, and improper immune development. The NF-kB signaling pathway has long been considered a prototypical pro-inflammatory pathway. Activation of NF-kB signaling is triggered in a series of steps through one of three recognizable pathways: the canonical, the non-canonical, and the atypical IκK independent pathways. In its unactivated state, NF-κB is bound to IκB. The activating signal (e.g., binding of TNF-α, IL-1α, LPS, CD40, Lymphotoxin, UV, HER2/Neu, $H_2O_2$, or other ligand) causes phosphorylation of IκB and triggers its degradation. The free unbound NF-κB can then translocate to the nucleus and activate transcription, e.g., of pro-inflammatory cytokines, chemokines, and adhesion molecules.

As shown in Example 1F below, administration of lubricin can reduce NF-κB translocation in a rheumatoid arthritis fibroblast-like synoviocyte model. It appears that PRG4's effect on NF-κB translocation is mediated by PRG4's effect on at least CD44, as shown by the data in Example 1F. Based on these data, PRG4 is indicated as an anti-inflammatory agent and is also indicated as an agent for treating inflammatory conditions, reducing or inhibiting inflammation, and reducing or inhibiting an inflammatory response. PRG4 is also indicated as treatment for any condition that could be improved by reducing translocation of NF-κB. This includes inflammatory conditions as NF-κB is a transcription factor involved in regulating expression of many pro-inflammatory cytokines produced by both the innate and adaptive immune system.

Applicants have also observed that lubricin achieves its anti-inflammatory effect by inhibiting or down-regulating production of a number of pro-inflammatory cytokines by mechanisms unknown. As shown by the data presented in Examples 2 and 3 below, lubricin down-regulates the production of pro-inflammatory cytokines and therefore, has an anti-inflammatory effect. This effect was demonstrated with lipopolysaccharide (LPS)-mediated inflammatory cytokine generation, TNF-α mediated-inflammatory cytokine generation, and tissue factor (TF)-mediated inflammatory cytokine generation. Accordingly, lubricin's effect on pro-inflammatory cytokine production have been verified in a number of different pathways.

Lubricin also can achieves its anti-inflammatory effect via its function as an anti-adhesive/lubricant. Applicants have observed that the mitochondria in cells subjected to mechanical stress can be deformed, perturbing their function, and leading to production of reactive oxidative species, cell death, and production of localized cell debris, and consequent local inflammation. The lubricating action of lubricin present at or about such mechanically stressed cells, to the extent it mitigates the mechanical stress on the cells and their mitochondria, also inhibits the development of localized inflammation.

By virtue of its anti-inflammatory properties, lubricin accordingly will be useful as a pan-immune modulator and as an anti-inflammatory agent to reduce or inhibit the inflammatory response through, for example, reducing or inhibiting pro-inflammatory cytokine generation. Consequently, lubricin is indicated as an agent for treating inflammatory conditions, reducing or inhibiting inflammation, and reducing or inhibiting an inflammatory response.

Accordingly, through these modes of action, PRG4 has the ability to down-regulate various signaling pathways involved in the inflammatory response and is therefore useful as an anti-inflammatory agent. As described herein, administration of PRG4 is indicated for treating a wide variety of inflammatory conditions and diseases and the inflammation associated with those conditions.

Uses of PRG4 as an Anti-Inflammatory Agent

Because of the anti-inflammatory properties of PRG4 disclosed herein, PRG4 is indicated for new uses previously unappreciated. In particular, PRG4 is indicated for use as an anti-inflammatory agent and is indicated for treating inflammatory conditions and reducing or inhibiting inflammation.

In one aspect, the invention provides a method for reducing or inhibiting an inflammatory response in a patient by administering PRG4 to the patient. In some embodiments, the patient may already be suffering from an inflammatory condition. In others he or she may be at risk of developing an inflammatory episode, e.g., when suffering from a recurring or chronic inflammatory condition.

In some embodiments, "treating" the patient may involve preventing the worsening of the condition, while in others it may involve alleviating or reducing or inhibiting inflammation associated with the condition. In still other embodiments, "treating" may refer to reducing the level of one or more pro-inflammatory cytokines in the patient.

In yet another aspect, the invention provides a method for reducing or inhibiting an inflammatory response in a patient by administering PRG4 to the patient where the PRG4 is administered to the patient at a site that is non-osseous, non-cartilaginous, non-ophthalmic, non-osteal, non-osseous, and non-articular or at such sites other than the urinary bladder, cornea, or the surface tissues of the oral cavity. Accordingly, administration of PRG4 locally and directly to bony or cartilaginous tissues, to the anterior surface of the eye, to articulating joints, to the urinary bladder, or to the mouth is outside of the scope of the subject matter claimed herein.

In yet another aspect, the invention provides a method for reducing or inhibiting an inflammatory response in a patient where the method involves administering PRG4 to the patient, which binds a CD44 receptor on a cell in the patient, reduces or inhibits the production of a pro-inflammatory cytokine in the patient, or reduces or inhibits translocation of NF-κB in a cell in the patient. As a result, the patient experiences a reduction or inhibition in the inflammatory response.

While the patient is preferably a human, the patient may be any mammal, for example a horse, a cow, a pig, a rat, a mouse, a dog, or a cat.

While lubricin is produced naturally within the body, the effects of the invention are observed when exogenous lubricin is administered to the patient. Accordingly, in one embodiment, the PRG4 administered to the patient is exogenous human lubricin, while in another embodiment, the PRG4 administered to the patient is recombinant human lubricin (rhPRG4). In another embodiment, rhPRG4 has the sequence of SEQ ID NO:1.

In one embodiment, the PRG4 is administered in an amount that is insufficient to provide boundary lubrication. Accordingly, a therapeutically effective amount of lubricin for administration according to the invention is in the range of 0.1 µg/kg to 4,000 µg/kg, or 0.1 µg/kg to 1,000 µg/kg, or 0.1 µg/kg to 100 µg/kg, or 0.1 to 50 µg/kg. In another embodiment, lubricin is administered, e.g., by application to a tissue surface, in an amount of 0.1 µg/mL to 30 mg/mL, or 1 µg/mL to 10 mg/mL, or 10 µg/mL to 1 mg/mL. In some embodiments, lubricin is administered in small volumes of 1 to 100 µL per dose. In some embodiments, lubricin is administered in large volumes of 100 µL to 4 L, for instance, as an enema. In further embodiments, lubricin is administered at concentrations no greater than 60 µg/mL.

The amount of lubricin administered will depend on variables such as the level or locus of the inflammation, the extent of the condition to be treated, the overall health of the patient, the pharmaceutical formulation, and the route of administration. The initial dosage can be increased beyond the upper level in order to rapidly achieve the desired blood-level or tissue level. Alternatively, the initial dosage can be smaller than the optimum, and the dosage may be progressively increased during the course of treatment. The optimal dose can be determined by routine experimentation.

For administration, lubricin is preferably combined with a pharmaceutically acceptable carrier. As used herein, "pharmaceutically acceptable carrier" means buffers, carriers, and excipients suitable for use in contact with the tissues of human beings and animals without excessive toxicity, irritation, allergic response, or other problem or complication, commensurate with a reasonable benefit/risk ratio. The carrier(s) should be "acceptable" in the sense of being compatible with the other ingredients of the formulations and not deleterious to the recipient. Pharmaceutically acceptable carriers include buffers, solvents, dispersion media, coatings, isotonic and absorption delaying agents, and the like, that are compatible with pharmaceutical administration. Carriers may also include biomaterials such as a matrices, hydrogels, polymers, tissue scaffolds, and resorbable carrier materials including collagen sponges. The use of such media and agents for pharmaceutically active substances is known in the art. Useful formulations can be prepared by methods well known in the pharmaceutical art. For example, see Remington's Pharmaceutical Sciences, 18$^{th}$ ed. (Mack Publishing Company, 1990). Formulation components suitable for parenteral administration include a sterile diluent such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as EDTA; buffers such as acetates, citrates or phosphates; and agents for the adjustment of tonicity such as sodium chloride or dextrose. Lubricin for administration can be presented in a dosage unit form and can be prepared by any suitable method and should be formulated to be compatible with its intended route of administration.

The invention contemplates that PRG4 may be administered to the patient systemically or locally. Local administration may be warranted in cases where the inflammatory response is localized to a specific tissue or organ and accessing the tissue or organ is possible by, for example, injection or local administration. However, systemic administration is also contemplated by some embodiments of the invention. Systemic administration may be warranted when the inflammatory response is localized but local administration is not feasible or otherwise indicated. Systemic administration also may be warranted when the inflammatory response is not localized in one area of the patient but is found throughout the patient or in more than one location in the patient. Further, because pro-inflammatory cells travel through the circulatory system of the patient, systemic administration may be the optimal mode of administration to ensure PRG4 has the greatest opportunity to interact with and counteract the activities of pro-inflammatory cells, e.g., in treatment of sepsis.

Accordingly in one embodiment of the invention, lubricin is administered systemically to achieve a reduction or inhibition of the inflammatory response or to treat an inflammatory condition. For example, lubricin may be systemically administered in an enteral manner, such as oral, rectal, sublingual, sublabial, or buccal delivery. In another embodiment, lubricin may be systemically administered in a parenteral manner, such as nasal, by inhalation, intravenous, intramuscular, subcutaneous, intradermal, intraperitoneal or transmucosal delivery.

In another embodiment, lubricin is administered locally to achieve a reduction or inhibition of the inflammatory response or to treat an inflammatory condition. For example, lubricin may be locally administered topically or by local injection to a body tissue or organ and may provide a coating of lubricin to, within, or around the specific body tissue or organ. According to one embodiment of the invention, when PRG4 is administered locally, it is administered at a location and at, around, to, or in the vicinity of a tissue that is non-cartilaginous, non-osseous, non-osteal, and non-articular, and is not the cornea, oral cavity, or urinary bladder. For example, in one embodiment, PRG4 is not locally administered to the cornea or surrounding tissues or to cartilaginous, bony, or articular joints or tissues. In another embodiment, PRG4 is not locally administered to the bladder or the mouth. In another embodiment, however, PRG4 is administered locally, for example, topically, or by injection, to posterior regions of the eye, to the skin, kidney, lungs, liver, a wound or surgical incision, thyroid, pancreas, spleen, thymus, ovary, testicle, uterus, adrenal gland, pituitary gland, hypothalamus, urethra, prostate, heart, artery or vessel, brain, or stomach. Administration is also conducted in orifices including the rectum, nose, ear, pharynx, larynx, trachea. Other areas for administration include the tongue, posterior eye, or the site of a tumor. Administration is also performed in visci including the small intestine, large intestine, colon or esophagus. The site of administration may be a location of inflammation in some embodiments, while in other embodiments, the site of administration may be chosen for ease of administration.

In a further embodiment, lubricin is administered locally to the thyroid to treat inflammation associated with gout by injection into or at the thyroid. In another embodiment, lubricin is administered locally to a site of trauma or tissue injury such as a wound or surgical incision by injection or topical application to the site. In another embodiment, lubricin is administered locally to the skin by topical administration.

For use in the practice of the invention PRG4 may be formulated in a carrier, e.g., suspended in phosphate buffered saline, at concentrations ranging from 1 µg/mL to 1,000 µg/mL, and more preferably, 100-500 µg/mL. Suitable carriers include physiological saline, bacteriostatic water, Cremophor EL™ (BASF, Parsippany, N.J.) or phosphate buffered saline (PBS), optionally in admixture with surfactants such as polysorbates. The carrier should be stable under the conditions of manufacture and storage, and should be preserved against microorganisms. The carrier can be a solvent or dispersion medium containing, for example, water, ethanol, polyol (for example, glycerol, propylene glycol, and liquid polyethylene glycol), and suitable mixtures thereof.

The timing of administration will depend on a variety of factors and the condition to be treated. For example, in one embodiment, administration of lubricin to treat inflammation that is incident to a chronic condition may result in administration daily, weekly, bi-weekly, twice daily or monthly. In another embodiment, treating inflammation that is incident to an acute condition, may require administration of lubricin continuously, for example, via intravenous drip, for a fixed period of time.

In one embodiment, the inflammatory response is an acute inflammatory response. Accordingly, in one embodiment, the inflammatory condition that is treated according to the invention, or the inflammatory condition suffered from by the patient is related to or caused by an infection, for example, a viral, bacterial, fungal, parasitic infection or by exposure to microbial toxins incident to the infection; necrosis, for example, caused by ischemia, trauma, physical or chemical injury, thermal injury or irradiation; foreign bodies such as splinters, dirt, foreign tissue, or sutures or other medical implant; or an immune reaction such due to hypersensitivity such as allergies leading to, for example, anaphylactic inflammation. In another embodiment, the inflammatory condition that is treated according to the invention, or the inflammatory condition suffered from by the patient is related to or caused by a chronic inflammatory response such as a persistent injury or infection such as tuberculosis or an ulcer; prolonged exposure to a toxin; allergy, or an autoimmune condition. Some chronic inflammatory conditions include diabetes, cancer, cardiovascular diseases, Alzheimer's disease, pulmonary diseases (e.g., tuberculosis), arthritis (e.g., gout, osteoarthritis), autoimmune diseases (e.g., multiple sclerosis, rheumatoid arthritis, lupus, celiac disease etc.), and neurological diseases.

Inflammatory conditions that may be treated by the methods of the invention include but are not limited to acne; acute organ failure; acute respiratory distress syndrome (ARDS); Addison's disease; allergic rhinitis; allograft rejection; alopecia areata; Alzheimer's disease; anaphylaxis; Appendicitis; arthritis; asthma; atherosclerosis; atopic dermatitis; autoimmune alopecia; autoimmune disease; autoimmune hyperthyroidism; autoimmune hypopituatarism; autoimmune polyglandular disease; Behcet's disease; brain injury; bronchitis; cancer; cardiopulmonary bypass syndrome; cardiorenal syndrome; Celiac disease; chronic actinic dermatitis; chronic obstructive pulmonary disease (COPD); chronic renal failure; colitis, contact dermatitis; Crohn's disease; dermatomyositis; dermatomyositis; diabetes; diabetic retinopathy; eczema; emphysema; foreign body rejection; glaucoma; glomerulonephritis; gout; graft vs. host disease; Graves' Disease; Guillain-Barre syndrome; Hashimoto's thyroiditis; hay fever; hepatorenal syndrome; hypersensitivity or allergy; inclusion body myositis; infection due to viral, fungal, parasitic or microbial infiltration; inflammatory bowel disease; inflammatory kidney disease; injury due to thermal or chemical exposure or irradiation; irritable bowel syndrome; ischemia; lung inflammation; macular degeneration; morphea; multiple sclerosis; mycosis fungoides; myocardial infarction; necrosis; non-infectious lung injury; osteoarthritis; pancreatitis; pernicious anemia; pneumonia; polymyositis; prostatitis; pseudogout; psoriasis; psoriatic arthritis; Pustulosis palmoplanteris; Pyoderma gangrenum; respiratory allergy; retinal inflammation; retinitis; rheumatoid arthritis; scleroderma; sepsis; serum sickness; Sezary's syndrome; Sjogren's syndrome; skin allergy; stroke; systemic inflammatory response syndrome (SIRS); systemic lupus erythematosus; systemic sclerosis; T-cell mediated hypersensitivity diseases; transplant rejection; trauma including from a gun wound, knife wound, automobile accident, fall, or combat; tuberculosis; ulcerative colitis; uticaria; uveitis; pericarditis, or vitiligo.

In some embodiments, inflammatory conditions of the joints or bones and inflammatory conditions of the eye may be treated by systemic administration of PRG4 and reducing or inhibiting inflammatory responses in tissues of the eye, joints, cartilage and bone. Such inflammatory conditions include but are not limited to macular degeneration, uveitis, retinitis and arthritis including osteoarthritis, psoriatic arthritis, juvenile idiopathic arthritis and rheumatoid arthritis.

In some embodiments where PRG4 binds a CD44 receptor on a cell, the cell may be a white blood cell (i.e., leukocyte) such as a lymphocyte (e.g., T-cell, B-cell, NK-cell), neutrophil, eosinophil, basophil, and monocyte, macrophage, or dendritic cell; adrenal cell; brain cell; cancer cell; cardiac cell; chondrocyte; colon cell; conjunctival cell; corneal cell; dendritic cell; endothelial cell; epithelial cell; fibroblast; gall bladder cell; gastric cell; hepatic cell; immune cell such as a mast cell, dendritic cell, lymphocyte, leukocyte or macrophage; intestinal cell; leukocytes; limbal cell; lung cell; lymphocyte; macrophage; mast cell; muscle cell; nerve cell; ocular or ophthalmic cell; osteoblast; osteoclast; pancreatic cell; rectal cell; renal cell; retinal cell; spleen cell; stem cell; synoviocyte; thymus cell; thyroid cell; trabecular meshwork cell; urethral cell; or vascular cell. However, this list is not limiting.

In some embodiments where PRG4 administration reduces or inhibits translocation of NF-κB in a cell, the cell may be a white blood cell (i.e., leukocyte) such as a lymphocyte (e.g., T-cell, B-cell, NK-cell), neutrophil, eosinophil, basophil, and monocyte, macrophage, or dendritic cell; adrenal cell; brain cell; cancer cell; cardiac cell; chondrocyte; colon cell; conjunctival cell; corneal cell; dendritic cell; endothelial cell; epithelial cell; fibroblast; gall bladder cell; gastric cell; hepatic cell; immune cell such as a mast cell, dendritic cell, lymphocyte, leukocyte or macrophage; intestinal cell; leukocytes; limbal cell; lung cell; lymphocyte; macrophage; mast cell; muscle cell; nerve cell; ocular or ophthalmic cell; osteoblast; osteoclast; pancreatic cell; rectal cell; renal cell; retinal cell; spleen cell; stem cell; synoviocyte; thymus cell; thyroid cell; trabecular meshwork cell; urethral cell; or vascular cell. However, this list is not limiting.

In some embodiments where PRG4 binds a CD44 receptor on a cell or where PRG4 administration reduces or inhibits translocation of NF-κB in a cell, when the cell is a synoviocyte, a chondrocyte, an osteocyte, an osteoblast, a retinal cell, a limbal cell, a trabecular meshwork cell, a corneal cell, a conjunctival cell, an ocular cell, or an ophthalmic cell, PRG4 is administered to the patient systemically.

In a further embodiment, the pro-inflammatory cytokine, the production of which is inhibited or reduced by the administration of lubricin is IL-1α, IL-1β, IL-2, IL-3, IL-4, IL-5, IL-6, IL-7, IL-8, IL-9, IL-10, IL-11, IL-12, IL-12p70, IL-13, IL-14, IL-15, IL-16, IL-17, IL-17α, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, IL-36, TNF-α, TNF-β (lymphotoxin-α), lymphotoxin-β, CXC31L (Fractalkine), CXCL-8, CCL2, CCL3, CCL4, CCL5, CCL11, CXCL10, IFN-α, IFN-β, IFN-ε, IFN-κ, IFN-ω, IFN-γ, VEGF, MCP-1, MCP-3, EGF, GMCSF, CD40L, CD27L, CD30L, FASL, 4-1BBL, OX40L, TRAIL, FGF-2, GRO, MDC, Rantes, G-CSF, M-CSF, FGF-2, EPO, MCSF, MIP3α, MG-CSF, or GCSF. In a further embodiment, administration of lubricin reduces or inhibits the level of one or more, two or more, or three or more, or four or more of the aforementioned pro-inflammatory cytokines.

In one embodiment, the reduction or inhibition of the production of a pro-inflammatory cytokine may be confirmed by the lower level of the cytokine in a body fluid sample taken from the patient after administration of lubricin compared to the level before. The body fluid sample may be blood or plasma, for example. Given that lubricin's effect on a given cytokine level may not be measurable immediately upon administration of lubricin, reduction or inhibition may be observed over the course of hours, days or weeks after the initial administration or lubricin.

In another aspect, the invention provides a method of inhibiting binding of a ligand to CD44 present on a surface. According to this method, the surface is exposed to lubricin and lubricin binds to CD44 and inhibits binding of the ligand.

In one embodiment, the surface may be the surface of a cell expressing CD44, such as a mammalian cell. In another embodiment, the surface is in a surface plasmon resonance detector. In yet another embodiment, the surface of the cell is in a human.

According to one embodiment, a cell expressing CD44 includes white blood cells (i.e., leukocytes) such as lymphocytes (e.g., T-cells, B-cells, NK-cells), neutrophils, eosinophils, basophils, and monocytes, macrophages, and dendritic cells; epithelial cells, endothelial cells, fibroblasts, synoviocytes, chondrocytes, osteoclasts, osteoblasts, cardiac cells, mast cells, muscle cells, lung cells, renal cells, hepatic cells, brain cells, spleen cells, urethral cells, vascular cells, nerve cells, pancreatic cells, gastric cells, intestinal cells, colon cells, rectal cells, ocular or ophthalmic cells, gall bladder cells, and stem cells.

In another embodiment, a cell expressing CD44 is a neoplastic or cancer cell. In one embodiment, a cancer cell includes breast cancer cells, colon cancer cells, endometrial cancer cells, ovarian cancer cells, skin cancer cells, bladder cancer cells, liver cancer cells, renal cancer cells, cervical cancer cells, lung cancer cells, tongue cancer cells, pancreatic cancer cells, non-small cell lung carcinoma cells, head and neck cancer cells, prostate cancer cells, uterine cancer cells, hepatocellular carcinoma cells, gastric cancer cells, nasopharyngeal carcinoma cells, gall bladder cancer cells, anal cancer cells, osteosarcoma cells, liposarcoma cells, leiomyosarcoma cells, rhabdomyosarcoma cells, neurofibrosarcoma cells, gastrointestinal stromal tumor cells, blood vessel tumor cells, fibrosarcoma cells, lymphoma cells, and brain cancer cells.

In one embodiment of the method, the ligand inhibited by the PRG4 binding to CD44 present on a surface may be hyaluronan (HA), a hyaluronan serum-derived hyaluronan associated protein complex (HA-SHAP), matrix-metalloproteinase-9, a cytokine, a chemokine, a interferon, an interleukin, a lymphokine, a tumor necrosis factor, a growth factor, or a hormone.

In one embodiment of this method, lubricin is provided in an amount that is insufficient to provide boundary lubrication. Applicants have determined that the effects of lubricin on CD44 binding can be achieved at concentrations much lower than what is necessary to achieve boundary lubrication. Accordingly, in one embodiment, lubricin is administered in an amount ranging from 0.1 µg/kg to 4,000 µg/kg. Lubricin, in one embodiment, is administered systemically, i.e., intravenous, subcutaneous, or intramuscular injection although it may be administered locally.

In one embodiment, the cell expressing CD44 is a mammalian cell and in another embodiment, the cell is a human cell. This invention may be applied in a number of contexts to treat disease and pathologic conditions where CD44 binding and/or activation by a ligand is involved.

Evidence suggests that CD44 signaling is involved in the progression of cancer and may also interfere with the effectiveness of certain chemotherapeutic medications. For example, it has been shown that resistance of multiple myeloma to treatment by dexamethasone, a chemotherapeutic, can be caused by CD44 engagement with HA. (Ohwada et al., *Eur J Heamatol* 2008; 80:245). Accordingly, in one embodiment, lubricin can be used to bind to CD44 on a cancer cell surface to inhibit CD44 signaling involved in cancer cell growth, survivability, progression or metastatic activity. In another embodiment, lubricin is administered to a patient having cancer or a patient at risk of developing cancer to treat the cancer or slow the growth or progression of a tumor. According to another embodiment, lubricin may be administered concurrently with a chemotherapeutic or radiologic treatment for cancer. Accordingly, in one embodiment, lubricin is administered to a patient having cancer wherein the lubricin is administered to treat the cancer, or wherein the lubricin is administered in connection with another cancer drug or treatment in order to treat the cancer. In one embodiment, the cancer is in a human subject.

In another embodiment, the cancer is adrenal cancer, anal cancer, bile duct cancer, bladder cancer, bone cancer, brain/CNS cancer, basal cell skin cancer, breast cancer, Castleman disease, cervical cancer, colorectal cancer, endometrial cancer, esophagus cancer, dermatofibrosarcoma protuberans, Ewing family of tumors, eye cancer, gall bladder cancer, gastrointestinal carcinoid tumors, gastrointestinal stromal tumor (GIST), gastric cancer, gestational trophoblastic disease, glioma, glioblastoma, head and neck cancer, hodgkin disease, kaposi sarcoma, kidney cancer, laryngeal and hypopharyngeal cancer, leukemia, lung cancer, liver cancer, lymphoma, malignant mesothelioma, Merkel cell carcinoma, melanoma, multiple myeloma, myeloma, myelodysplastic syndrome, nasal cavity and paranasal sinus cancer, nasopharyngeal cancer, neuroendocrine cancer, neuroblastoma, Non-Hodgkin lymphoma, oral cavity and oropharyngeal cancer, osteosarcoma, ovarian cancer, pancreatic cancer, penile cancer, pituitary Tumors, prostate cancer, renal cancer, retinoblastoma, rhabdomyosarcoma, salivary gland cancer, sarcoma, squamous cell skin cancer, small intestine cancer, stomach cancer, testicular cancer, thymus cancer, thyroid cancer, uterine cancer, uterine sarcoma, vaginal cancer, vulvar cancer, Waldenstrom macroglobulinemia, or Wilms tumor.

CD44 is also involved in the progression of diabetes and evidence suggests that blocking CD44 can provide an antidiabetic effect. HA is found in the islet cells of the pancreas and binding of HA to CD44 on islet cells leads to inflammation and destruction of islet cells leading to insulin dependent diabetes. Accordingly, in one embodiment, the invention provides a method of preventing or treating diabetes by administering lubricin to a patient having or at risk of developing diabetes. In another embodiment, lubricin is contacted with pancreatic cells in a concentration sufficient to bind CD44, thereby inhibiting or reducing the interaction between CD44 and HA in the pancreas.

In another embodiment the PRG4 may be used to treat inflammatory bowel disease such as Crohn's disease or colitis. In such instances, a concentrated solution of PRG4 will be introduced into the gastrointestinal tract by simple ingestion, enema, a feeding tube, G-tube, J-tube or a colostomy. In the case of ingestion the PRG4 may be encapsulated within an a tablet, enclosure or capsule, preferably biodegradable, wherein the tablet, enclosure or capsule is made of a substance that degrades or otherwise dissociates when exposed to conditions present in the gastro-intestinal tract of a patient. Such oral formulations may be present in a polymer as a slow release delivery system. Oral formulations are well known in drug delivery technology and one of skill could select such a tablet, enclosure or capsule as appropriate for ingestable delivery of PRG-4.

In another embodiment the PRG4 may be used to treat brain injury caused by stroke, embolism, or trauma. For treatment of brain injury, a concentrated solution of PRG4 will be injected IV following stroke, embolism or trauma within a limited time period following brain injury. Alternatively, the PRG4 may be placed during brain surgery at a location in the brain during said surgery. This administration of such a composition to the brain is designed to stabilize blood vessels, limit vascular permeability and also confer an anti-inflammatory effect.

In another embodiment the PRG4 may be used to reduce the symptoms associated with allergies and/or respiratory infections. Such symptoms include congestion, post-nasal drip, coughing, sneezing, runny nose, itchy throat, itchy skin, and itchy watery eyes, to name a few. In an embodiment of the invention, a method is provided for treating a patient exhibiting such symptoms or at risk of developing such symptoms including the step of administering to a surface of the patient's body suffering or at risk of developing allergy symptoms, e.g., skin, or respiratory tract, e.g., upper respiratory tract, an amount of a PRG4-containing composition sufficient to ameliorate the symptoms. The method of this embodiment may comprise depositing intranasally onto the mucosal surface of the nose and sinuses of a patient an amount of a nasal composition comprising PRG4 in an amount sufficient to ameliorate at least one allergy and/or upper respiratory infection symptom. In one embodiment, the PRG4-containing nasal composition is administered as a nasal spray.

Allergy is a species of inflammation, an adaptive immune reaction that includes such maladies as allergic asthma, atopic dermatitis, allergic rhinitis and several ocular allergic diseases. It is characterized by a Th2 mediated humoral response to antigenic challenge. In a typical Type I hypersensitivity allergic reaction, initial exposure to an allergen causes B cells to produce IgE antibodies that bind to the surface of mast cells/basophils, sensitizing those cells to the allergen. Subsequent exposure to the same antigen results in an immediate degranulation of the mast cell and subsequent release of histamine, prostaglandins, leukotrienes (LTC4, LTD4, LTE4), chemokines (CXCL8, CXCL10, CCL2, CCL4, CCL5), proteases (tryptase, chymase) and cytokines such as IL-4, IL-5, and IL-13 (Janeway et al., Immunobiology: The Immune System in Health and Disease. 5th edition. New York: Garland Science 2001; Larché et al., Nat Rev Immunol. 2006; 6(10):761-71). These effector molecules cause dilation of small blood vessels, increased vascular permeability, bulk mucus production, and local contraction of smooth muscles resulting in the familiar symptoms associated with allergic reactions. After several hours, the late phase of the allergic reaction sees the recruitment of eosinophils, basophils and Th2 lymphocytes to the site of the reaction. Eosinophils release a series of granule proteins such as eosinophil cationic protein, major basic protein, eosinophil peroxidase and eosinophil-derived neurotoxin, as well as a series of reactive oxygen species (peroxides) that act to clean out the area through oxidative stress and ribonuclease activity. While toxic to invading organisms, eosinophil responses also disrupt host cells in the vicinity of the allergic reaction.

Once the positive feedback loop of tissue damage and inflammatory cell recruitment has been established, a chronic inflammatory state may persist, even without sustained exposure to the original allergen (Murdoch J R, Lloyd C M. Chronic Inflammation and Asthma. Mutat Res. 2010; August 7; 690(1-2):24-39. doi: 10.1016/j.mrfmmm.2009.09. 005. Epub 2009 Sep. 19). In particular, chronic inflammation is accompanied by remodeling of the tissues that result in compromised epithelial barrier function, matrix metalloproteinase expression and mucus gland hyperplasia, as well as TGF-β mediated fibrosis (Murdoch et al.). For instance, in chronic asthma, repeated cycles of eosinophil mediated damage and subsequent matrix synthesis by fibroblasts leads to thickened, constricted, less elastic airways, with airway remodeling being linked directly to the chronicity of the disorder (Murdoch et al.). It is noteworthy that the dominant asthma therapies aimed at reducing inflammation (corticosteroids), exhibit limited efficacy in ameliorating remodeling (Murdoch et al.; Ward C, Walters H., Curr Opin Allergy Clin Immunol. 2006; February; 5(1):43-8). Such abnormal tissue remodeling and TGF-β mediated fibrosis may also be found to be associated with repeated surgeries at a site within a patient.

Accordingly, in an embodiment of the invention, the application of PRG4-containing compositions to tissues undergoing a chronic allergic response will benefit from improved allergen clearance as well as reduced inflammation by the inhalation of aerosolized PRG4. The boundary lubricating ability of such compositions will also prevent mucus particulate adhesion to the epithelium, as well as improved hydration, as the highly charged PRG4 molecule is hygroscopic and will retain water along the interface of the epithelia. Due to the improved tissue surface lubrication following the application of PRG4-containing compositions, mechanical clearance of allergens will require less force as the friction between particulates (comprising bulk mucin, debris and allergens) and the epithelium is reduced. With lower friction, mechanical clearance through, e.g. air flow and mucociliary clearance (respiratory system), will require less force and result in less tissue damage and inflammation. Administration of PRG4-containing compositions to patients suffering from chronic allergy will also result in mitigation of fibrosis through prevention of fibroblast adhesion and migration which will reduce the overall fibrotic response.

Without wishing to be bound by theory, this aspect of the current invention is based in part on the recognition that the sequelae associated with an immune dysregulation or chronic exposure to allergens may result in impaired mechanical clearance of antigens, PAMPs and DAMPs, as well as compromised tissue function associated with repeated remodeling. Lubricin can facilitate mechanical clearance of allergens or cellular debris. Not only do these processes potentiate inflammation, but also result in long-term damage to the tissues, whether respiratory, ocular, or skin, and it is believed the positive feedback loop conditions are similar.

Further evidence suggests that the CD44-HA interaction may lead to swollen spleen, a condition often associated with diabetes. Accordingly, one aspect of the invention provides a method of contacting the spleen with lubricin to prevent inflammation and swelling of the spleen. In another embodiment, lubricin is contacted with spleen cells in a concentration sufficient to bind CD44, thereby reducing swelling and inflammation in the spleen.

CD44 is also present in synovial tissues and is up-regulated in patients with rheumatoid arthritis. It has been shown that CD44 expressing synoviocytes bind to HA-SHAP in synovial fluid obtained from human rheumatoid arthritis patients. The amount of complex formed correlates positively with the degree of inflammation. This is demonstrated by data shown in Example 4. Accordingly, systemically administered lubricin is indicated as a treatment for decreasing inflammation in patients suffering from rheumatoid arthritis. In one embodiment, lubricin is administered systemically to a patient having rheumatoid arthritis to block the effect of CD44 upregulation and to reduce inflammation. In a one embodiment, lubricin is periodically administered via an intravenous route. In another embodiment, lubricin is delivered via an external, portable pump through an indwelling subcutaneous catheter.

CD44-HA interactions may also play a key role in the deleterious leukocyte trafficking at the blood-retinal barrier and anterior segment immunopathologies (Xu H, et al. *Journal of Leukocyte Biology* 2002; 72(6):1133-41), as well as in glaucoma where a significant correlation was found between levels of soluble CD44 severity of visual field loss (Mokbel T H et al., *Clin Experiment Ophthalmol.* 2010 August; 38(6):560-5). In one aspect, rhPRG4 is administered to the eye to antagonize CD44 and interrupt HA interactions. In one embodiment, injected rhPRG4 reduces inflammation and allows improved blood flow and survivability of retinal cells. In another embodiment, rhPRG4 injected into the eye prevents CD44 mediated clogging of the trabecular meshwork in primary open angle glaucoma, resulting in a lowered intra-ocular pressure. In another embodiment rhPRG4 inactivates soluble CD44 within the humor, preventing cytotoxicity of the soluble CD44. In another embodiment, rhPRG4 antagonizes transmembrane CD44, interrupts metalloproteinase cleavage of the extracellular domain, and prevents an increase in soluble CD44. In another embodiment, lubricin injected into the eye reduces visual sequelae such as floaters, blurred vision and photopsia associated with posterior uveitis. In another embodiment, lubricin injected into the eye interrupts CD44 and RHAMM mediated angiogenesis and endothelial cell migration by preventing association of low molecular weight HA degradation products from interacting. Other embodiments include the injection or topical application of lubricin into the eye to prevent CD44 mediated progression of macular degeneration, retinitis, retinal vasculitis, chorioretinitis, neovascularization and diabetic retinopathy. For example, given the localized ophthalmic environment, the lubricin is administered in an amount of 0.1 µg/mL to 30 mg/mL in small volumes (1-100 µL) per dose.

In yet another embodiment of the invention rhPRG4 may be utilized to treat non-CD44 mediated eye disorders, using the methods and compositions as described above. In such instances, the injection or topical application of lubricin into the eye may be used to prevent non-CD44 mediated progression of macular degeneration, retinitis, retinal vasculitis, chorioretinitis, neovascularization and diabetic retinopathy.

In another aspect, the invention provides a method of reducing or inhibiting the level of pro-inflammatory cytokines in the body, the method comprising systemically, inhalationally or topically administering PRG4 in an amount sufficient to inhibit or reduce pro-inflammatory cytokine levels. In one embodiment, the method reduces or inhibits the level of one pro-inflammatory cytokine, while in another, the method reduces or inhibits the level of more than one pro-inflammatory cytokine. Exemplary inflammatory conditions, injuries, and autoimmune conditions causing an inflammatory response that leads to increased levels of pro-inflammatory cytokines in the blood and from which a patient being treated according to the invention may suffer have been are disclosed throughout this application.

According to one embodiment, cytokines whose production may be inhibited or reduced by administration of lubricin include IL-1α, IL-1β, IL-2, IL-3, IL-4, IL-5, IL-6, IL-7, IL-8, IL-9, IL-10, IL-11, IL-12, IL-12p70, IL-13, IL-14, IL-15, IL-16, IL-17, IL-17α, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, IL-36, TNF-α, TNF-β (lymphotoxin-α), lymphotoxin-β, CXC31L (Fractalkine), CXCL-8, CCL2, CCL3, CCL4, CCL5, CCL11, CXCL10, IFN-α, IFN-β, IFN-ε, IFN-κ, IFN-ω, IFN-γ, VEGF, MCP-1, MCP-3, EGF, GMCSF, CD40L, CD27L, CD30L, FASL, 4-1BBL, OX40L, TRAIL, FGF-2, GRO, MDC, Rantes, G-CSF, M-CSF, FGF-2, EPO, MCSF, MIP3α, MG-CSF, or GCSF.

In one embodiment, the blood is human blood. In a further embodiment, the blood is that of a human patient experiencing an inflammatory response or condition. In one embodiment, the inflammatory response or condition is the result of an injury to a tissue, while in another, the inflammatory response is the result of an autoimmune condition, while in another embodiment, the inflammatory response is the result of a bacterial or viral infection or the presence of a toxin. In yet another embodiment, the patient is suffering from or at risk of sepsis.

In a further embodiment, the human cell is an immune cell such as a mast cell, dendritic cell, lymphocyte, leukocyte or macrophage; an epithelial cell; endothelial cell; fibroblast; synoviocyte; chondrocyte; osteoclast; osteoblast; cardiac cell; mast cell; lung cell; renal cell; hepatic cell; brain cell; spleen cell; bladder or urethral cell; vascular cell; nerve cell; pancreatic cell; gastric cell; intestinal cell; colon cell; rectal cell; retinal cell; limbal cell; trabecular meshwork cell; corneal cell; conjunctival cell; ocular or ophthalmic cell; gall bladder cell; or cancer cell.

In one embodiment, lubricin is administered in amount insufficient to provide boundary lubrication, i.e., it is administered in the range of 0.1 µg/kg to 4,000 µg/kg. In another embodiment, lubricin is administered in an amount of 0.1 µg/mL to 30 mg/mL and is administered in small volumes of 1 to 100 µL per dose. In another embodiment, lubricin is administered in volumes of 100 µL to 4 L per dose. In one embodiment, lubricin is provided to a human patient by systemic administration.

In a particular embodiment, the cell is in a patient suffering or at risk of developing sepsis, for example, caused by exposure to viral or bacterial toxins such as LPS, flagellin, or the like. Accordingly, in one aspect, lubricin is indicated as a treatment for sepsis.

In a further aspect, the invention provides a method for inhibiting NF-κB translocation in a cell by contacting the cell with PRG4, wherein PRG4 inhibits activation of the NF-κB signaling pathway. In one embodiment, PRG4 inhibits NF-κB translocation indirectly by binding to CD44 or reducing or inhibiting CD44 signaling or interacting with other cell-surface bound receptors. The PRG4 may be administered according to the embodiments of the invention described herein above, including by systemic administration. The cell may be a human cell and in particular may be any of the exemplary human cells described herein with respect to the invention.

In a further embodiment, the result of PRG4 mediated reduction or inhibition of NF-κB translocation results in reduction of proinflammatory cytokine levels in the blood and thereby may be used to treat an inflammatory condition. Exemplary inflammatory conditions have been described throughout this application.

Example 1: Experimental Evidence that PRG4 Antagonizes CD44 and Inhibits CD44 Mediated Inflammatory Pathways To evaluate the interaction between human proteoglycan 4 and the CD44 receptor and the consequence of this interaction on pro-inflammatory cytokine induced synoviocyte proliferation, the following experiments were performed.

rhPRG4 binding to CD44 and competition with high molecular weight hyaluronic acid (HMW HA) was evaluated using a direct enzyme linked immunosorbent assay (ELISA) and surface plasmon resonance. Sialidase-A and O-glycosidase digestion of rhPRG4 was performed and CD44 binding was evaluated using ELISA. Rheumatoid arthritis fibroblast-like synoviocytes (RA-FLS) were stimulated with interleukin-1 beta (IL-1β) or tumor necrosis factor alpha (TNF-α) for 48 hours in the presence or absence of rhPRG4 or HMW HA at 20, 40 and 80 µg/mL and cell proliferation was measured. CD44 contribution was assessed by co-incubation with an anti-CD44 antibody (IM7). The anti-proliferative effect of rhPRG4 was investigated following treatment of Prg4−/− synoviocytes with IL-1β or TNF-α in the presence or absence of IM7.

Variables were initially tested for normality and equal variances. Variables that satisfied both assumptions were tested for statistical significance using Student's t-test or analysis of variance (ANOVA) with Tukey's post-hoc test for two group and more than two group comparisons, respectively. Variables that did not satisfy the normality assumption were tested using Mann-Whitney U test or ANOVA on the ranks. The level of statistical significance was set at α=0.05. Data is graphically represented as the average±standard deviation.

1A. Binding of rhPRG4, High-Molecular Weight HA, Medium-Molecular Weight HA and Vitronectin to CD44 Using a Direct ELISA High-binding microtiter plates (Corning, Sigma Aldrich, USA) were coated with rhPRG4 ($M_r \cong 240$ KDa), high molecular weight HA (HMW HA; $M_r \cong 1,500$ KDa) (R & D System, USA), medium molecular weight HA (MMW HA; $M_r \cong 300$ KDa) (R & D System) and vitronectin ($M_r \cong 75$ KDa) (Sigma Aldrich) at 400 μg/mL in PBS buffer (100 μL per well) overnight at 4° C. rhPRG4 is a full-length product produced by CHO-M cells (Lubris, Framingham, Mass., USA). Following washing with PBS+0.1% Tween 20, wells were blocked with 2% bovine serum albumin (BSA; 300 μL per well) for at least 2 hours at room temperature. CD44-IgG$_1$Fc (R & D systems) or IgG$_1$Fc (R & D systems), each at 1 μg/mL (100 μl per well), were added to the plate and incubated for 60 min at room temperature. Following washing with PBS+0.1% tween 20, anti-IgG$_1$Fc-HRP (Sigma Aldrich) was added at 1:10,000 dilution (100 μL per well) and incubated for 60 min at room temp. Following washing with PBS+0.1% tween 20, the assay was developed using 1-step Turbo TMB ELISA reagent (ThermoScientific, USA) and absorbance was measured at 450 nm. The data represents an average of 4 independent assays, each with triplicate wells per group.

Binding of rhPRG4, HMW HA, MMW HA and vitronectin to CD44-IgG$_1$Fc fusion protein and IgG$_1$Fc is presented in FIG. 1A. The 450 nm absorbance in the CD44-IgG$_1$Fc group was significantly higher (p<0.001) than the absorbance in the IgG$_1$Fc group for rhPRG4, HMW HA and MMW HA-coated wells. In contrast, there was no significant difference between CD44-IgG$_1$Fc and IgG$_1$Fc in the vitronectin-coated wells.

These data show that rhPRG4 binds CD44 and interferes with HMW HA CD44 binding. rhPRG4, HMW HA and MMW HA specifically bind to chimeric CD44 with extremely low non-specific binding. In contrast, vitronectin that shares significant sequence homology with lubricin does not show any specificity towards CD44 binding. Because rhPRG4 binds CD44, it may function as an antagonist of CD44, thereby interfering with CD44 pro-inflammatory signaling.

Figure 1B:
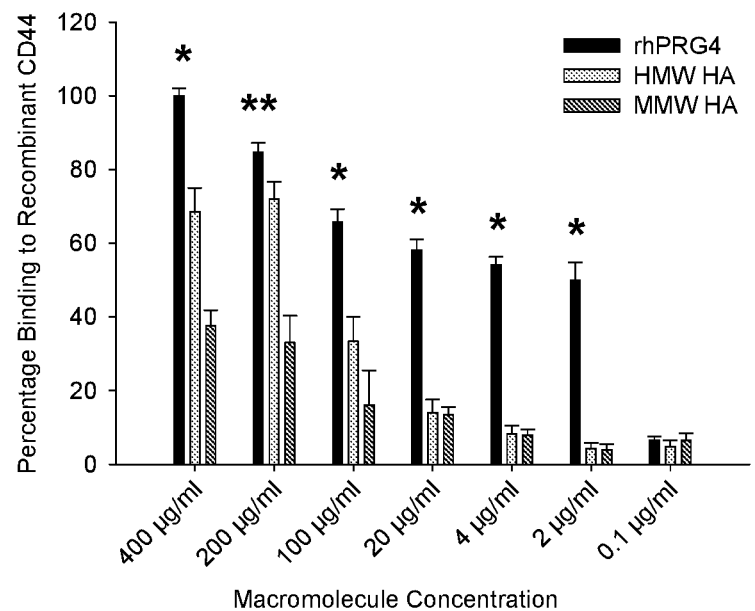

1B. Concentration-Dependent Binding of rhPRG4, HMW HA, MMW HA to CD44 and Competition Between rhPRG4 and HA on Binding to CD44 Using a Direct ELISA The concentration-dependent binding of rhPRG4, HMW HA and MMW HA to CD44 was performed by coating microtiter plates with 400, 200, 100, 20, 4, 2 and 0.1 μg/mL of the macromolecules. The assay was performed as described above. The absorbance values in the IgG$_1$Fc wells were subtracted from the absorbance values in the CD44 IgG$_1$Fc wells and the corrected CD44 IgG$_1$Fc absorbance values were normalized to those of the 400 μg/mL rhPRG4 group and data was expressed as percentage binding to CD44. The concentration-dependent binding of rhPRG4, HMW HA and MMW HA to recombinant CD44 is depicted in FIG. 1B. The percentage recombinant CD44 binding was significantly higher (p<0.001) in the rhPRG4-coated wells compared to the HMW HA or MMW HA-coated wells for the 400, 100, 20, 4 and 2 μg/mL concentrations. Additionally, the percentage recombinant CD44 binding was significantly higher (p<0.001) in the rhPRG4-coated wells compared to the MMW HA coated wells for the 200 μg/mL concentration. There were no significant differences in percentage CD44 binding between the rhPRG4, HMW HA and MMW HA-coated wells at the 0.1 μg/mL concentration. The data represents an average of 4 independent assays, each with triplicate wells per group.

To evaluate the competition between rhPRG4 and either HMW HA or MMW HA on binding to CD44, microtiter plates were coated with either CD44 IgG$_1$Fc or IgG$_1$Fc at 1 μg/mL (100 μL per well) overnight at 4° C. Subsequently, wells were washed with PBS+0.1% tween 20 and wells were blocked using 2% BSA (300 μL per well) for at least 2 hours at room temperature. Either rhPRG4 at 5 μg/mL or a combination of rhPRG4 (5 μg/mL) and HMW HA or MMW HA at 0.01, 0.05, 0.25, 1, 5 or 50 μg/mL were added to the wells (100 μL per well) and incubated at room temperature for 60 min. Following washing with PBS+0.1% tween 20, lubricin-specific monoclonal antibody (Mab 9G3) was added at 1:1,000 (100 μL per well) and incubated for 60 min at room temp. Following washing with PBS+0.1% tween 20, goat anti-mouse IgG-HRP (Thermo Scientific) at 1:1,000 dilution was added (100 μL per well) and incubated for 60 min at room temp. The assay was developed as described above. The absorbance values in the IgG$_1$Fc wells were subtracted from the absorbance values in the CD44-IgG$_1$Fc wells and the corrected absorbance values in the rhPRG4+HA groups were normalized to the absorbance values of the rhPRG4 group and data was expressed as percentage binding to CD44. The data represents an average of 4 independent assays, each with triplicate wells per group.

Figure 1C:
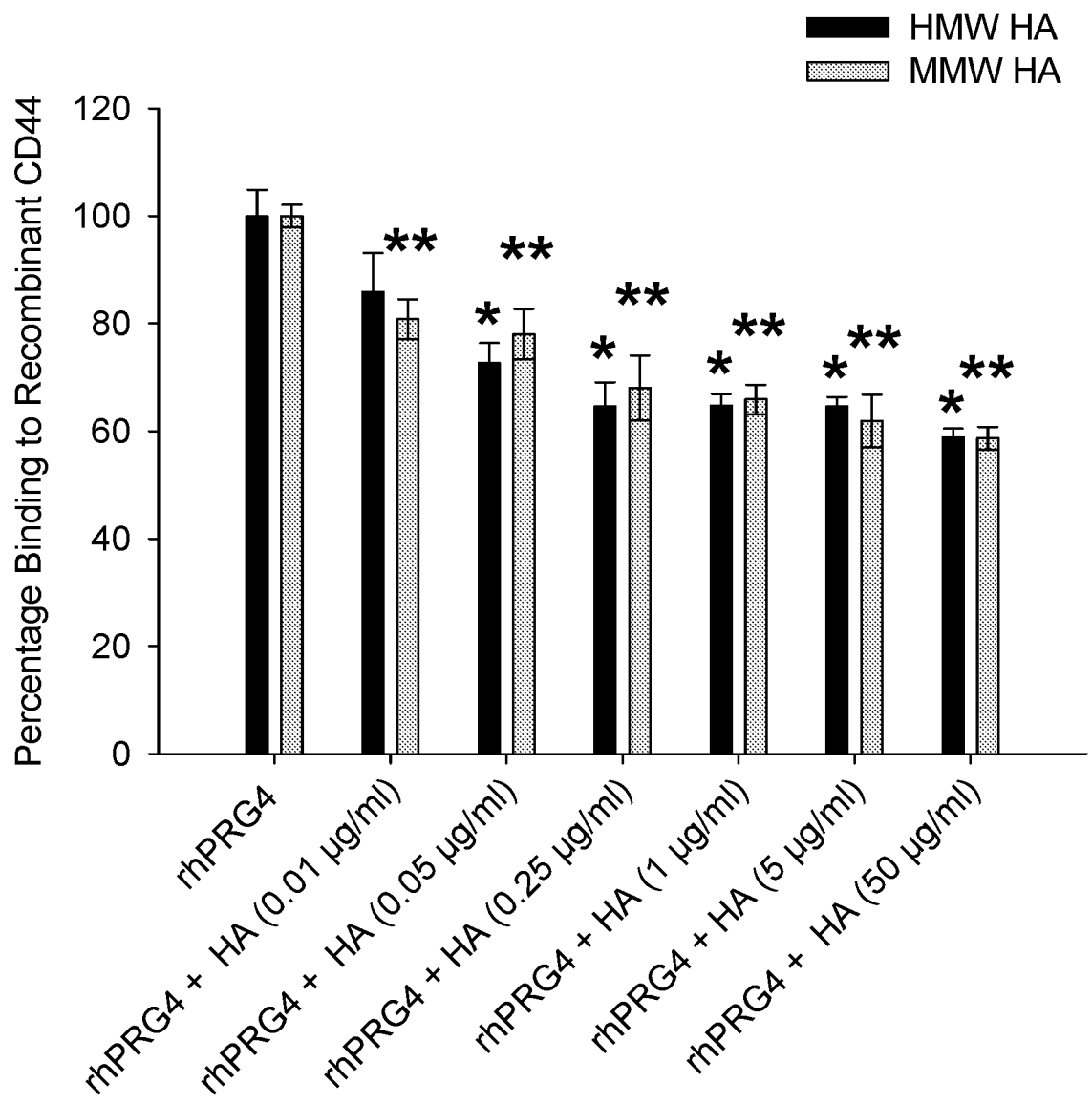

The competition between rhPRG4 and HMW HA or MMW HA in binding to recombinant CD44 is presented in FIG. 1C. HMW HA or MMW HA at 0.05, 0.25, 1, 5 and 25 μg/mL significantly reduced rhPRG4's binding to CD44 (p<0.05).

These data demonstrate that rhPRG4 binds to CD44 in a concentration-dependent manner with comparable affinity to HMW HA. Furthermore, rhPRG4 competes with HMW HA in binding to CD44. The presence of an excess of HMW or MMW HA reduced rhPRG4 binding to CD44 only by approximately 50%. These data suggest that rhPRG4 is an antagonist of CD44; accordingly, it has the potential to interfere with CD44 pro-inflammatory signaling.

1C. Concentration-Dependent Binding of rhPRG4 to CD44 and Competition Between rhPRG4 and HMW HA Using Surface Plasmon Resonance Binding of rhPRG4 to CD44-IgG1Fc was investigated using surface plasmon resonance (Biacore T100, GE Healthcare Lifesciences, N.J., USA). See FIG. 1C. Series S chips were functionalized using the human antibody capture kit (GE Life Sciences) and either CD44-IgG$_1$Fc or IgG$_1$FC was allowed to bind to the surface of the functionalized chips in flow cell 1 (Fc$_1$) and flow cell 2 (Fc$_2$), respectively. rhPRG4 was injected at 30 µL/min for 8 min at concentrations of 300, 250, 200, 150, 100 and 50 µg/mL followed by a 10 min dissociation using 0.1M HEPES, 1.5M NaCl, 30 mM EDTA, and 0.5% P20 (GE Life Sciences). The surface of the chip was regenerated at the end of each cycle with 1 min pulse of 3M MgCl$_2$. Each analyte concentration was injected in duplicate. The resulting curves were double referenced (i.e. Fc$_2$-Fc$_1$, followed by subtraction of the 0 µg/mL curve). The binding kinetics and binding affinity were determined by BiaEvaluation software, using 1:1 binding/conformational change model or by steady-state equilibrium, respectively. To study the competition between rhPRG4 and HMW HA in binding to CD44, rhPRG4 was injected at concentrations ranging between 0 and 300 µg/mL as described above. Following the end of dissociation phase, HMW HA was injected at 50 µg/mL (30 µL per min) for 1 min. The double-referenced binding signals of rhPRG4 (at various concentrations) to CD44 were then plotted against the binding signals generated by HMW HA binding to CD44 following rhPRG4 injections.

Figures 2A, 2B:
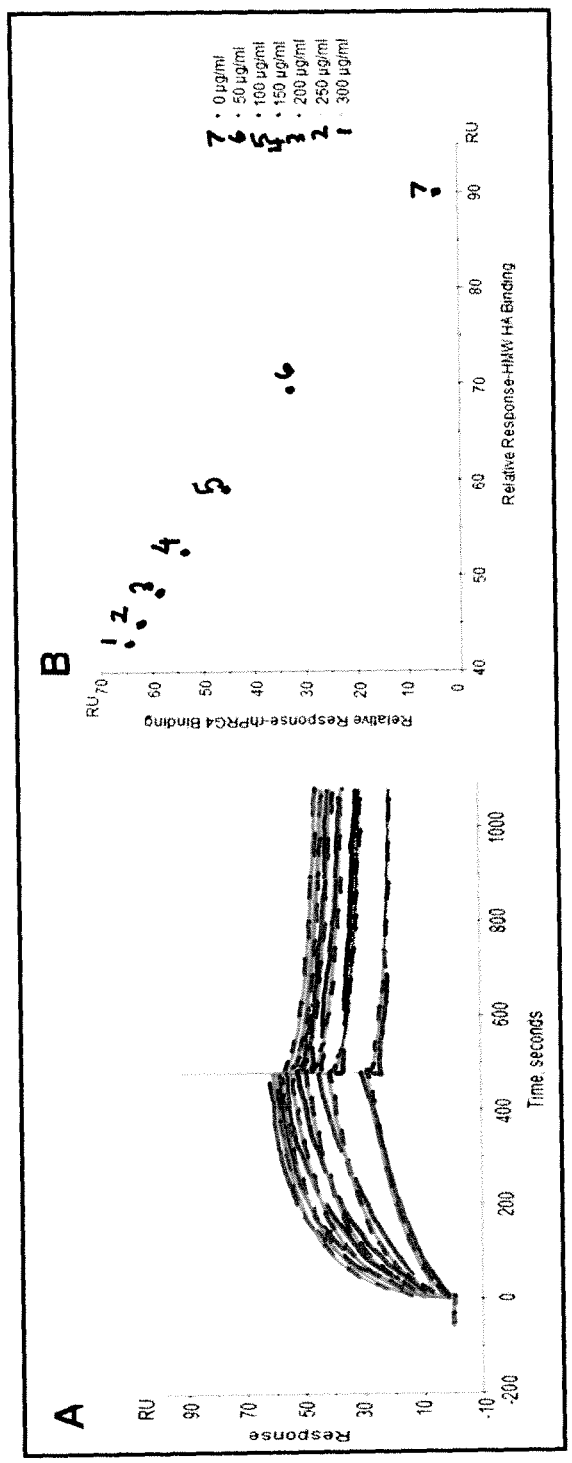
FIGS. 2A-B depict binding of recombinant human proteoglycan 4 (rhPRG4) to recombinant CD44 and competition between rhPRG4 and high molecular weight hyaluronic acid (HMW HA) on CD44 binding using surface plasmon resonance.

The binding of rhPRG4 to recombinant CD44 was confirmed using surface plasmon resonance. rhPRG4 displayed a concentration-dependent association with, and dissociation from immobilized CD44-IgG$_1$Fc (FIG. 2A), with an apparent K$_d$≅38 nM based on a rhPRG4 molecular weight of 240 KDa. rhPRG4 interfered with binding of HMW HA to recombinant CD44 as shown by an inverse relationship between the HMW HA binding signal intensity (x-axis) and the rhPRG4 binding signal intensity (y-axis) (FIG. 2B).

These data demonstrate that rhPRG4 binds to CD44 in a concentration-dependent manner with comparable affinity to HMW HA. Further, as demonstrated in Example 1B and 1C, the presence of rhPRG4 bound to CD44 prevented HMW HA from binding to CD44 in a concentration-dependent manner and may indicate that rhPRG4 and HMW HA share a common binding site on the receptor. In the joint environment where HA SF concentration is roughly 10 times higher than that of lubricin, and based on the competitive binding data shown herein, it is expected that lubricin will be able to bind to CD44 on surface of synoviocytes and chondrocytes and exert a CD44-mediated biological function in the presence of HA, thereby providing a joint homeostatic role by interfering with mediators that otherwise promote inflammation.

1D. Impact of Removal of Mucin-Domain Glycosylations on Binding of rhPRG4 to CD44

Lubricin's boundary lubricating ability is mediated by the O-linked (β1-3) Gal-GalNAc oligosaccharides (Jay et al., *Glucoconj J* 2001; 18(10):807-15). A combination of neuraminidase and beta 1,3, 6 galactosidase digestions reduced lubricin's boundary lubricating ability by 50% (Jay et al., *Glucoconj J* 2001; 18(10):807-15). Lubricin isolated from RA SF samples contains increased core 1 glycosylation structures and displays the sulfated epitope that is proposed to be part of the L-selectin ligand (Estrella et al., *Biochem J* 2010; 429(2):359-67). Additionally, lubricin from RA SF binds L-selectin in a glycosylation-dependent manner and coats polymorphonuclear granulocytes recruited to inflamed synovia and SF of patients with RA (Jin et al. *J Biol Chem* 2012; 287(43):35922-33).

rhPRG4 was digested using sialidase A (Prozyme, USA), O-glycosidase (New England Biolabs, USA) or a combination of sialidase A and O-glycosidase for 16 hours at 37° C. In the sialidase A digestion, 12 µL of the enzyme (1 U/200 µL) was added to rhPRG4 in a total reaction volume of 180 µL and a rhPRG4 final concentration of 300 µg/mL. In the O-glycosidase digestion, 4.8 µL of the enzyme (40 million units/mL) was added to rhPRG4 in a total reaction volume of 180 µL and a rhPRG4 final concentration of 300 µg/mL under non-denaturing conditions. In the sialidase-A and O-glycosidase digestion, the enzymes were used in volumes identical to the ones stated above and incubated with rhPRG4 in a total reaction volume and final rhPRG4 concentration as stated above. The effect of sialidase-A and O-glycosidase digestions on rhPRG4 apparent molecular weight was determined by SDS-PAGE using 4-12% Bis-Tris gel (NuPage, life technologies, USA). A total of 20 µL of rhPRG4 or enzyme-digested rhPRG4 was run under reducing conditions (200 mV for 60 min) followed by staining using Gelcode Blue Stain (Thermo Scientific, USA). Binding of enzymatically digested rhPRG4 to CD44 was compared to undigested rhPRG4 using the direct ELISA approach described above and using an rhPRG4 coating concentration of 30 µg/mL. Data represents the average of 4 independent experiments, each with triplicate wells per group.

Figure 3A:
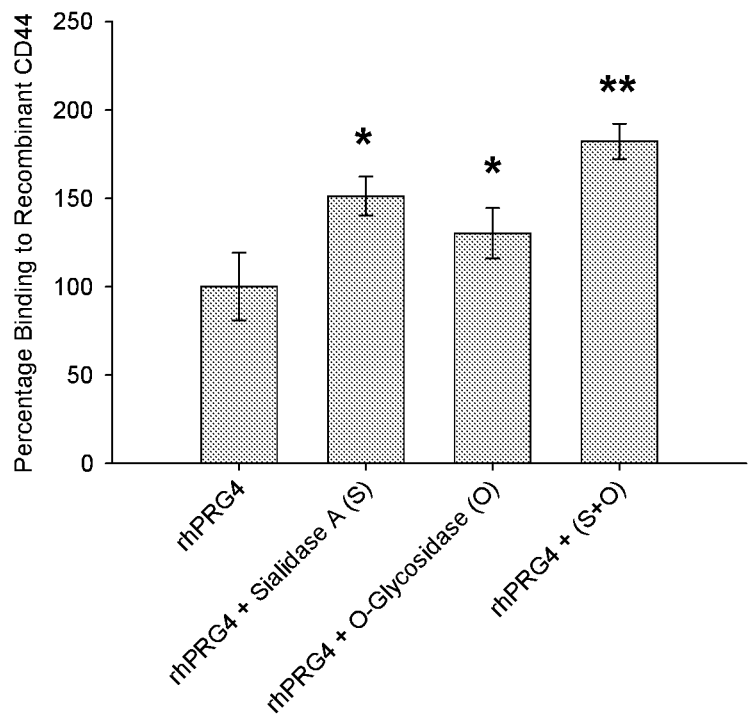
FIGS. 3A-B show the impact of sialidase-A and O-glycosidase digestion of recombinant human proteoglycan 4 (rhPRG4) on binding of rhPRG4 to CD44. Data represents the average of 4 independent experiments with triplicate wells per group.
Figure 3B:
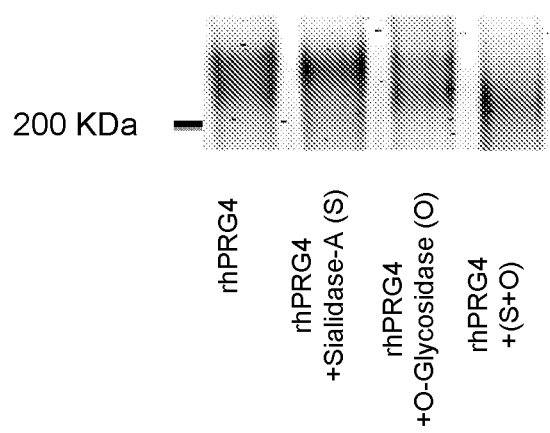

Sialidase-A digestion resulted in a significant increase (p<0.001) in the percentage binding of rhPRG4 to CD44 compared to untreated control as shown in FIG. 3A. Similarly, O-glycosidase digestion resulted in a significant increase (p=0.008) in the percentage binding of rhPRG4 to CD44 compared to untreated control. There was no significant difference in percentage CD44 binding between the sialidase-A digested and the O-glycosidase codigested rhPRG4 (p=0.105). The percentage binding to CD44 in the sialidase-A and O-glycosidase-digested rhPRG4 was significantly higher than sialidase-A digested rhPRG4 (p=0.007), O-glycosidase digested rhPRG4 (p<0.001) and untreated control (p<0.001). Digestion of rhPRG4 with sialidase-A and O-glycosidase resulted in reducing the apparent molecular weight of rhPRG4 to approximately 200 KDa (FIG. 3B).

Removal of sialic acid and O-glycosylations significantly increased CD44 binding by rhPRG4 (p<0.001). Sialidase-A and O-glycosidase treatments individually resulted in enhancing rhPRG4's binding to CD44 receptor. Cumulative sialidase-A and O-glycosidase digestions resulted in even more significant binding to CD44 by rhPRG4 compared to individual enzyme digestions. Sialidase-A cleaves branched and unbranched terminal sialic acid residues from glycoproteins, while O-glycosidase catalyzes the removal of cores 1 and 2 from glycoproteins. The enhancement in CD44 binding indicates that neither the core 1 glycosylation nor the sialic acid terminal residues are required in rhPRG4 binding to CD44. Accordingly, the level of sialylation and core 1 glycosylations on rhPRG4 protein core are not essential to the PRG4's ability to bind CD44. In contrast, removal of these residues may lead to a conformational change in the rhPRG4 semi-rigid rod shaped structure that results in enhanced interaction with CD44.

1E. Pro-Inflammatory Cytokine-Induced Rheumatoid Arthritis Fibroblast-Like Synoviocyte Proliferation and Impact of rhPRG4 or HMW HA Treatment The synovia of patients with RA contain considerable amounts of various CD44 isoforms and are generally present to a higher degree compared to OA or normal synovia (Naor et al., *Arthritis Res Ther* 2003; 5(3):105-15. Grisar et al., *Clin Exp Rheumatol* 2012; 30(1): 64-72). Rheumatoid arthritis fibroblast-like synoviocytes (RA-FLS) play an important role in the invasiveness of the synovia of patients with RA. The expression of a unique CD44 variant (CD44v7/8) contributes to the proliferation of RA-FLS in vitro (Wibulswas et al., *Am J Pathol* 2000; 157(6):2037-2044) and pharmacological agents that bind cell surface CD44 with subsequent receptor shedding have shown efficacy in experimental arthritis models (Runnels et al. *Adv Ther* 2010; 27(3):168-80).

Rheumatoid arthritis fibroblast-like synoviocytes (RA-FLS; Cell Applications, USA) between $3^{rd}$ and $6^{th}$ passages were used to conduct these experiments. In sterile 96 well plates, RA-FLS (5,000 cells per well in 80 µL) were cultured in DMEM supplemented with 1% FBS and 1 mM pyruvate and stimulated with recombinant human interleukin-1 beta (IL-1β; R & D systems) at 20 ng/mL or tumor necrosis factor alpha (TNF-α; R & D systems) at 5 ng/mL for 48 hours at 37° C. in the absence or presence of rhPRG4 or HMW HA at a final concentration of 20, 40 or 80 µg/mL. The total volume in each well was 200 µL. Cell proliferation, an indication of inflammation, was determined using the Cell-Titer 96 AQueous one solution cell proliferation assay (MTS; Promega, USA) and the 490 nm absorbance was determined. Data is presented as the number of fold change in 490 nm absorbance compared to untreated control RA-FLS. The data represents the average of 3 independent experiments with at least triplicate wells per treatment. To evaluate the contribution of CD44 to the effect of rhPRG4 or HMW HA, RA-FLS were stimulated with IL-1β or TNF-α as described above. Treatment with rhPRG4 or HMW HA was conducted to a final concentration of 80 µg/mL in the absence or presence of IM7 (Abcam, USA), a CD44 neutralizing antibody that recognizes a conserved epitope across all CD44 isoforms (Samson et al., *Exp Eye Res*, 2014; 127C:14-19), at a final dilution of 1:200. The total volume in each well was 200 µl. Cell proliferation across the experimental groups was determined as described above and data is presented as the number of fold change in 490 nm absorbance compared to untreated control RA-FLS. The data represents the average of 3 independent experiments with at least triplicate wells per treatment.

Figure 4A:
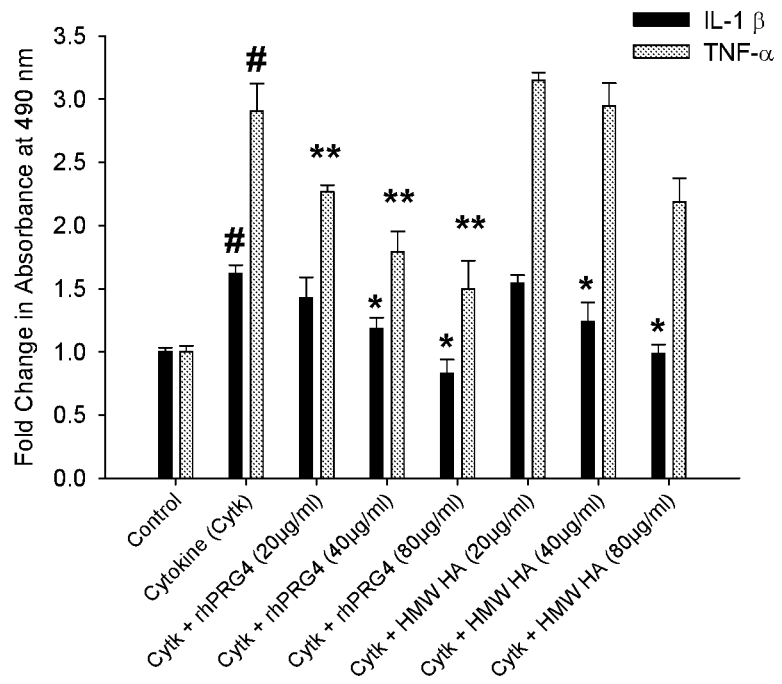
FIGS. 4A-B show the impact of recombinant human proteoglycan 4 (rhPRG4) and high molecular weight hyaluronic acid (HMW HA) treatment on cytokine induced proliferation of rheumatoid arthritis fibroblast-like synoviocytes (RA-FLS). Data represents the average of 3 independent experiments with triplicate wells per treatment.
Figure 4B:
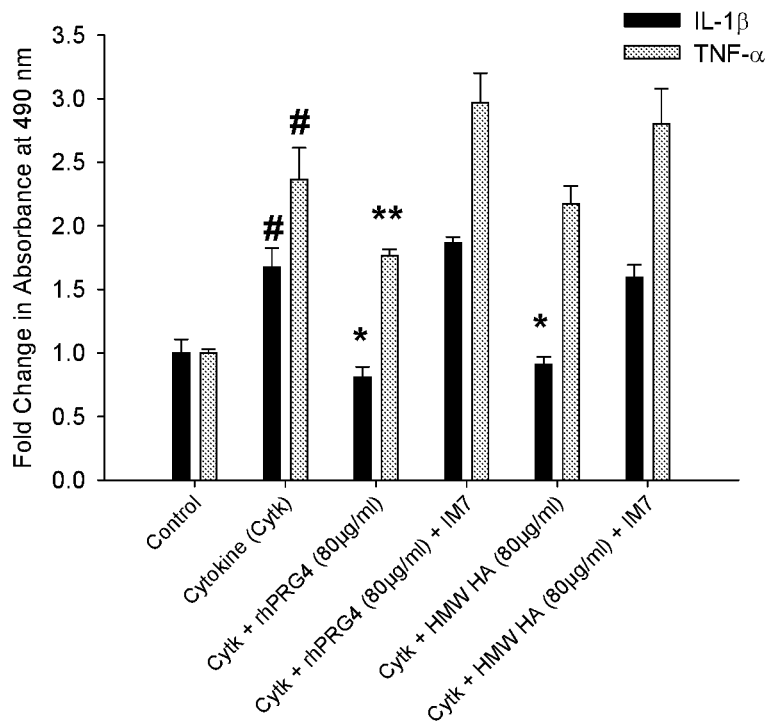

IL-1β and TNF-α induced RA-FLS proliferation over a 48 hour period is shown in FIG. 4A. Treatment with 40 and 80 µg/mL rhPRG4 or HMW HA significantly suppressed RA-FLS proliferation with IL-1β stimulation (p<0.05). Treatment with 20, 40 and 80 µg/mL rhPRG4 significantly suppressed RA-FLS proliferation with TNF-α stimulation (p<0.05). Treatment with HMW HA did not result in suppressing RA-FLS proliferation with TNF-α. Co-treatment with the IM7 anti-CD44 antibody reversed the effect of rhPRG4 and HMW HA on IL-1β stimulated RA-FLS as shown by the lack of significant difference in the change of absorbance between the IL-1β stimulated RA-FLS treated with rhPRG4+IM7 or HMW HA+IM7 and IL-1β stimulated RA-FLS as shown in FIG. 4B. Similarly, co-treatment with IM7 antibody reversed the effect of rhPRG4 on TNF-α induced RA-FLS proliferation.

rhPRG4 and HMW HA at 40 and 80 µg/mL significantly suppressed IL-1β induced RA-FLS proliferation (p<0.05). rhPRG4 at 20, 40 and 80 µg/mL significantly suppressed TNF-α induced RA-FLS proliferation (p<0.05). CD44 neutralization reversed the effect of rhPRG4 on IL-1β and TNF-α stimulated RA-FLS and the effect of HMW HA on IL-1β stimulated RA-FLS.

IL-1β and TNF-α induced RA-FLS proliferation with higher cell proliferation observed with TNF-α stimulation, which is in agreement with other published reports (e.g., Lacey et al. *Arthritis Rheum* 2003; 48(1):103-109). rhPRG4 inhibited the IL-1β and TNF-α induced RA-FLS proliferation in a mechanism that involves CD44 binding. The downstream effect of rhPRG4 and CD44 interaction is the inhibition of nuclear translocation of NF-κB. In this cell proliferation assay, HMW HA inhibited IL-1β induced proliferation of RA-FLS but did not inhibit TNF-α induced proliferation. As with rhPRG4 treatment, the effect of HMW HA was reversed with a CD44 antibody, indicating the role of CD44 in mediating this effect.

These data show that rhPRG4 exerts an anti-proliferative, anti-inflammatory effect on RA-FLS subsequent to IL-1β or TNF-α stimulation. Interestingly, rhPRG4 concentrations that demonstrate this anti-proliferative effect are generally lower than the optimal rhPRG4 concentrations required to provide boundary lubrication. This anti-proliferative effect of rhPRG4 is mediated by CD44 interaction with a downstream inhibition of NF-κB nuclear translocation, suggesting that therapeutically applied lubricin may mitigate the effects of pro-inflammatory cytokines on the proliferation of deleterious cell types via a CD44 dependent mechanism.

1F. Effect of rhPRG4 Treatment on Nuclear Translocation of NFκB Following TNF-α Stimulation of RA-FLS RA-FLS (400,000 cells/well) were cultured and stimulated with TNF-α (5 ng/mL) and treated with rhPRG4 (200 µg/mL) or a commercially available NFκB translocation inhibitor MG 132 (3 µM; Tocris Bioscience) for 24 hours in serum free media. Cells were harvested and nuclear extraction was performed using a commercially available kit (Thermo scientific). Total protein was measured using a micro bicinchonic acid (BCA) kit (Thermo scientific) and 3 µg of nuclear extract of each experimental group were used. The p50 subunit of NFκB was detected in the nuclear extract using a commercially available NFκB DNA binding assay kit (Abcam). Data is presented as the number of fold change in NFκB nuclear levels compared to untreated control. To evaluate whether inhibition of NFκB translocation by rhPRG4 is CD44 dependent, the above experiment was repeated in the presence or absence of IM7 CD44 antibody (1:1,000 dilution). Data represents the average of 3 independent experiments with at least triplicate wells per treatment.

Figure 4C:
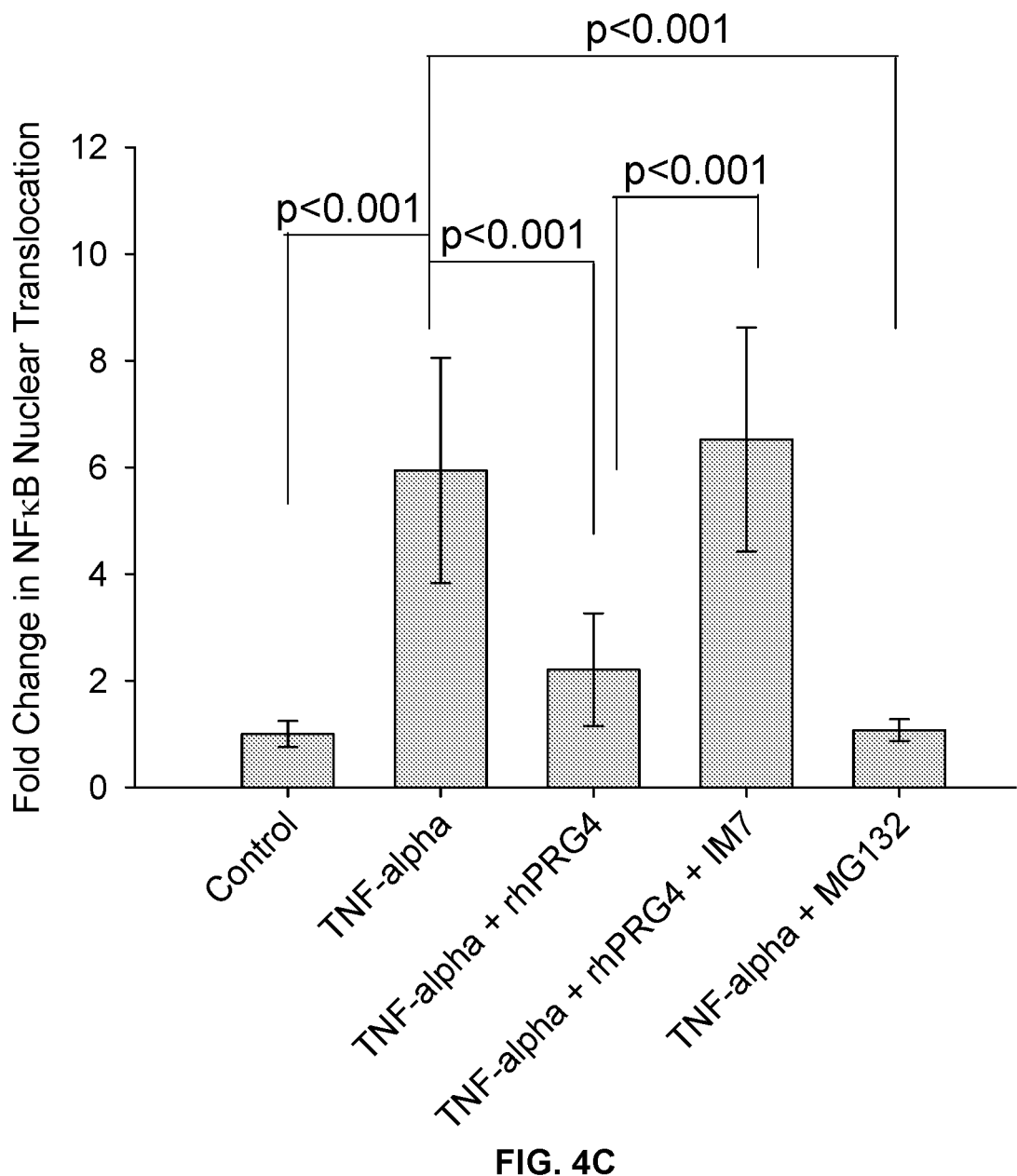
FIG. 4C is a bar graph depicting rhPRG4 inhibition of TNF-α induced NF-κB nuclear translocation in RA-FLS. Nuclear translocation of NF-κB in the TNF-α+rhPRG4 group was significantly lower than TNF-α alone or TNF-α+rhPRG4+IM7 groups ($p<0.001$). Treatment with rhPRG4 or NFκB translocation inhibitor MG132 significantly reduced NFκB nuclear translocation compared to TNF-α-treated RA-FLS ($p<0.001$).

TNF-α treatment resulted in significant NFκB nuclear translocation compared to untreated controls (p<0.001) (FIG. 4C). Treatment with rhPRG4 or NFκB translocation inhibitor MG132 significantly reduced NFκB nuclear translocation compared to TNF-α-treated RA-FLS (p<0.001). NFκB nuclear translocation in the TNF-α+rhPRG4+IM7 group was significantly higher than NFκB translocation in the TNF-α+rhPRG4 group (p<0.001) and was not significantly different from the TNF-α group. Accordingly, the anti-proliferative, anti-inflammatory effect of rhPRG4 is mediated by CD44 interaction, with a downstream inhibition of NFκB nuclear translocation, suggesting that rhPRG4 has the ability to directly reduce the pro-inflammatory effects of NF-κB nuclear translocation via a CD44 dependent mechanism.

1G. Isolation of Prg4−/− and Prg4+/+ Synoviocytes and CD44 Immunocytochemistry Synovial tissue was harvested from Prg4−/− and Prg4+/+ male mice (8-10 weeks old; 5-8 animals per genotype) and digested with pronase enzyme (2 mg/mL; Sigma Aldrich) in sterile HBSS buffer for 30 min at 37° C. with shaking. This was followed by digestion with type I collagenase (1 mg/mL; Sigma Aldrich) for 4 hours at 37° C. with shaking. The enzymatic reaction was stopped using DMEM+10% FBS. Cells were grown in DMEM+10% FBS and Prg4−/− synoviocytes were used between $2^{nd}$ and $4^{th}$ passages while Prg4+/+ synoviocytes were used in their second passage.

Prg4−/− and Prg4+/+ synoviocytes were grown in chamber slides (Thermo Scientific). Cells were fixed in 4% formaldehyde for 15 min and washed twice with PBS buffer. Cells were permeabilized with 0.2% Triton X-100 for 10 min and washed 3 times with PBS buffer. Cells were blocked with 2% BSA for 30 min. Synoviocytes were incubated with IM7 anti-CD44 antibody (1:200) at 4° C. overnight. Following washing three times with PBS, synoviocytes were incubated with Alexa Fluor 488 goat anti-rat IgG (Life Technologies) at 1:400 dilution for 1 hour in the dark. All incubations were performed at room temperature unless otherwise specified. Following washing with PBS for 5 min, Vectashield mounting medium containing DAPI (Vector Labs, Burlingame, Calif., USA) was added. Cells were imaged with the Nikon Eclipse 90i Fluorescence Microscope using NIS Elements imaging software.

Figure 5B:
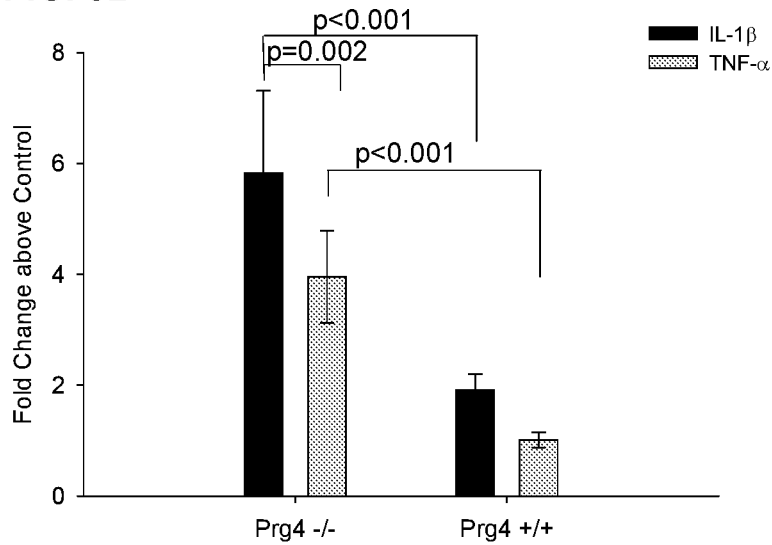

CD44 immunocytochemistry of Prg4−/− and Prg4+/+ synoviocytes is shown in FIG. 5A. Intense green fluorescence, indicative of CD44 localization and unoccupied CD44 epitopes, was observed for Prg4−/− synoviocytes. Alternatively, no or faint green fluorescence was observed for Prg4+/+ synoviocytes, indicating that most CD44 receptors (epitopes) were occupied or antagonized by native Prg4 expression. IL-1β and TNF-α treatment resulted in a significant increase in Prg4−/− synoviocytes proliferation compared to untreated Prg4−/− synoviocytes (p<0.001) (FIG. 5B). In contrast, only IL-1β stimulation resulted in a significant increase in Prg4+/+ synoviocyte proliferation compared to untreated Prg4+/+ synoviocytes (p<0.001). Additionally, the fold increase in IL-1β and TNF-α induced proliferation of Prg4−/− synoviocytes was significantly higher than the fold increase in cytokine induced proliferation of Prg4+/+ synoviocytes (p<0.001).

Figure 5C:
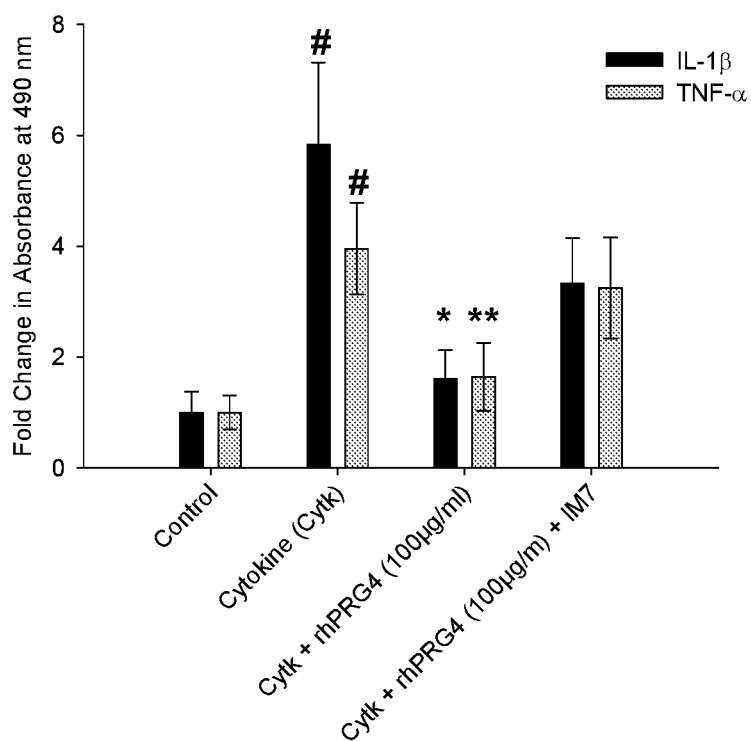

Treatment with rhPRG4 significantly inhibited IL-1β and TNF-α induced proliferation of Prg4−/− synoviocytes (p<0.001) (FIG. 5C). Co-treatment with IM7 reversed the effect of rhPRG4. This is illustrated by the significant increase (p<0.001) in Prg4−/− synoviocyte proliferation in the IL-1β+rhPRG4+IM7 and TNF-α+rhPRG4+IM7 groups compared to IL-1β+rhPRG4 and TNF-α+rhPRG4 groups, respectively. There was no significant difference in Prg4−/− synoviocyte proliferation between TNF-α+rhPRG4+IM7 and TNF-α groups. In contrast, Prg4−/− synoviocyte proliferation was significantly higher in the IL-1β group than the IL-1β+rhPRG4+IM7 group (p<0.001).

Prg4−/− mice exhibit early signs of cartilage degeneration, demonstrated by surface fibrillations and increased joint coefficient of friction compared to Prg4+/− and Prg4+/+ mice (Jay et al., *Arthritis Rheum*, 2007; 56(11): 3662-9). Additionally, Prg4−/− mice exhibit increased activated caspase-3 chondrocyte staining in articular cartilage compared to age-matched Prg4+/+ cartilage (Waller et al., *Proc. Natl. Acad. Sci. USA*, 2013; 110(15): 5852-7) and synovial hyperplasia and overgrowth is evident in Prg4−/− mice, with no obvious synovial hyperplasia in Prg4+/− or Prg4+/+ mice (Rhee et al., *J. Clin. Invest*, 2005; 115(3):622-31). Prg4−/− synoviocytes display enhanced CD44 staining compared to Prg4+/+ synoviocytes. Additionally, pro-inflammatory cytokines induced significant proliferation of Prg4−/− synoviocytes with no appreciable effect on Prg4+/+ synoviocytes. Combined, these observations indicate an ongoing inflammation in Prg4−/− joints with a proliferating synoviocyte phenotype resembling that of RA-FLS. rhPRG4 inhibited cytokine-induced Prg4−/− synoviocyte proliferation and this effect was mediated by rhPRG4-CD44 interaction. Neutralizing CD44 completely reversed the anti-proliferative effect of rhPRG4 following TNF-α stimulation and partially reversed the anti-proliferative effect of rhPRG4 following IL-1β stimulation. This difference related to rhPRG4-CD44 interaction in the setting of TNF-α and IL-1β stimulation of Prg4−/− synoviocytes may potentially be due to rhPRG4's ability to modulate other signaling pathways independent of its ability to interact with CD44. Accordingly, rhPRG4 inhibits IL-1β and TNF-α induced proliferation of Prg4−/− synoviocytes in a mechanism that involves CD44, and therefore is an antagonist of CD44 capable of down-regulating the pro-inflammatory activity of CD44 signaling.

Figure 8B:
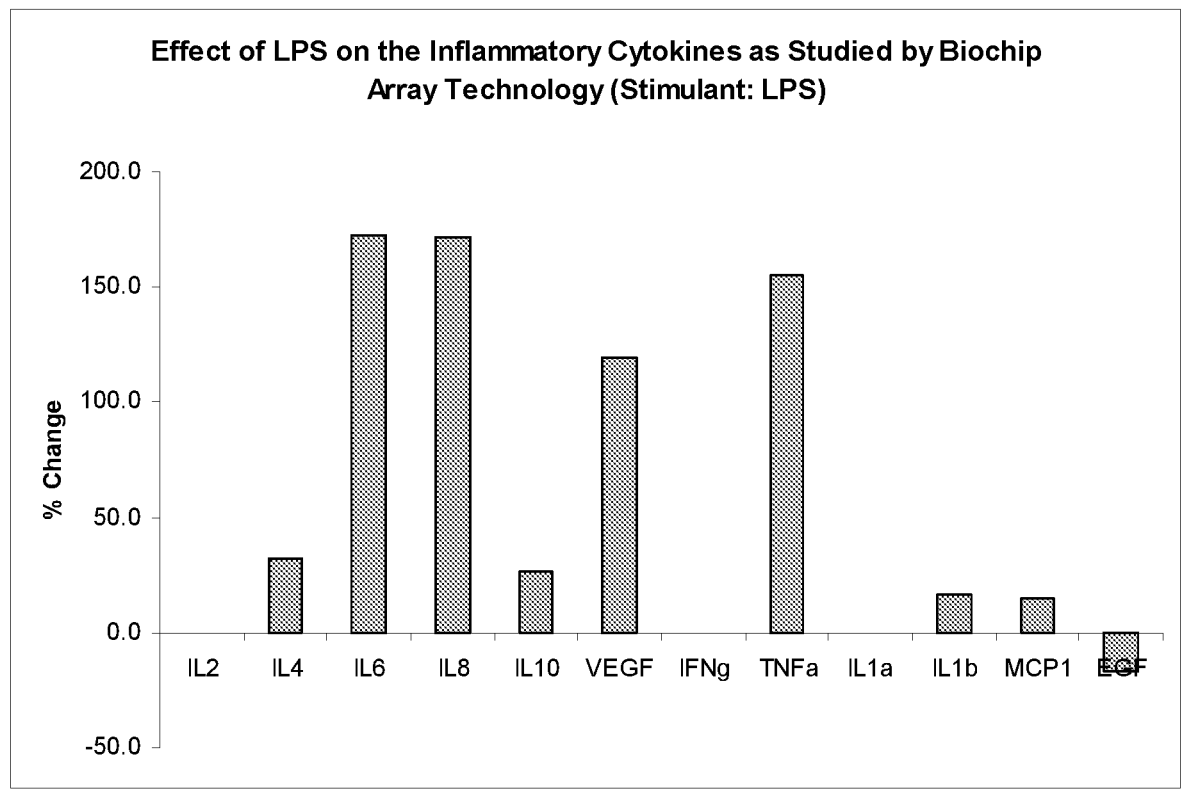

Example 2: Lubricin Modulates Production of Inflammatory Cytokines in Human Whole Blood Systems Lipopolysaccharides (LPS) are found in the outer membrane of Gram-negative bacteria and elicit strong immune inflammatory responses in animals. The effect of LPS challenge on the production of inflammatory cytokines was studied in citrated whole human blood using Biochip Array technology to profile the generation of various cytokines and the modulation of their production. The generation of IL2, IL4, IL6, IL8, IL10, VEGF, IFNg, TNFa, IL1a, IL1b, MCP1 and EGF was studied in citrated whole blood samples supplemented with saline (1-10 ratio) and LPS at 10 μg/mL in samples incubated for 60 minutes at 37° C. These mixtures were centrifuged and the supernatant plasma was analyzed for the 14 inflammatory biomarkers using a high sensitivity cytokine array on a Randox Investigator Biochip reader. These studies were run in duplicate and tabulated in the form of a table and a figure. As shown in FIGS. 8A-B, supplementation of lipopolysaccharide in a 1:10 dilution in whole blood results in an increase in production of the inflammatory cytokines IL-4, IL-6, IL-8, IL-10, VEGF, TNF-α, IL1-β, and MCP-1 under the specified conditions. No changes in IL2, IFNg, and IL1b were noted. FIG. 8B shows the percent changes in the various parameters clearly demonstrating a pronounced increase in IL6, IL8, VEGF and TNFa.

Figure 9B:
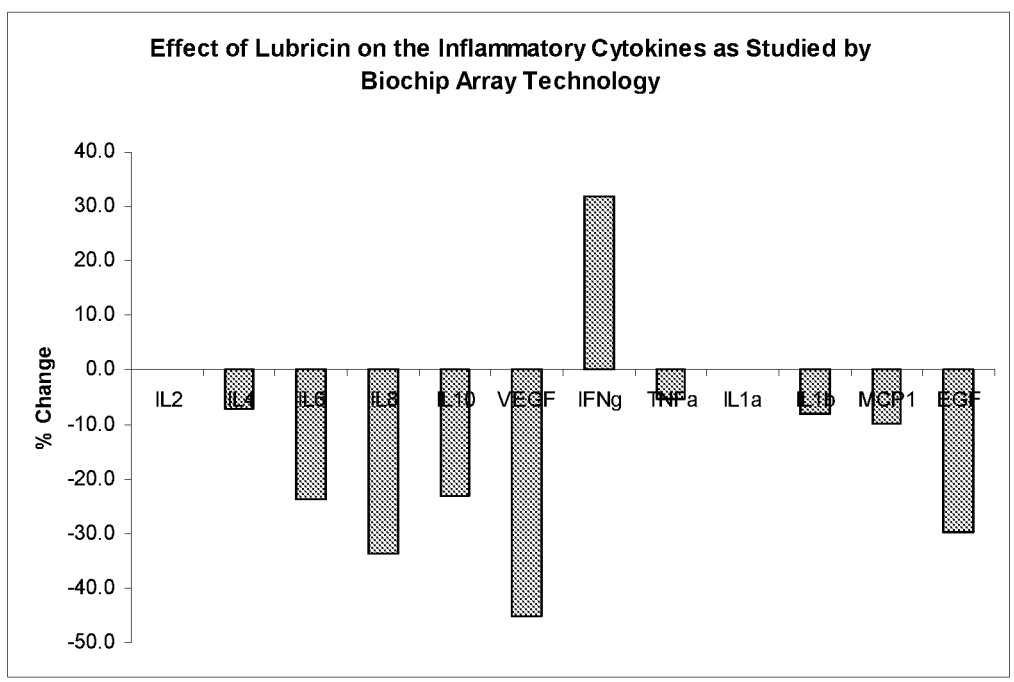

Utilizing the same approach the effect of lubricin on the generation of inflammatory cytokines in whole blood was also studied using similar experimental settings. In these studies the effect of lubricin (0.57 mg/mL) was studied by supplementing it to the whole citrated blood drawn from the normal healthy volunteers. The samples were profiled for inflammatory cytokine levels along with a saline control in samples incubated for 60 minutes. Whole blood was centrifuged to obtain plasma which was profiled for various inflammatory cytokines using high sensitivity cytokine assay. As shown in FIGS. 9A-B, supplementation with lubricin at 0.57 mg/mL in whole blood resulted in a decrease in production of IL-4, IL-6, IL-8, IL-10, VEGF, TNF-α, IL-1β, MCP-1, and EGF. The most prominent decrease was seen in VEGF, IL8, IL6 and IL10.

Figure 10B:
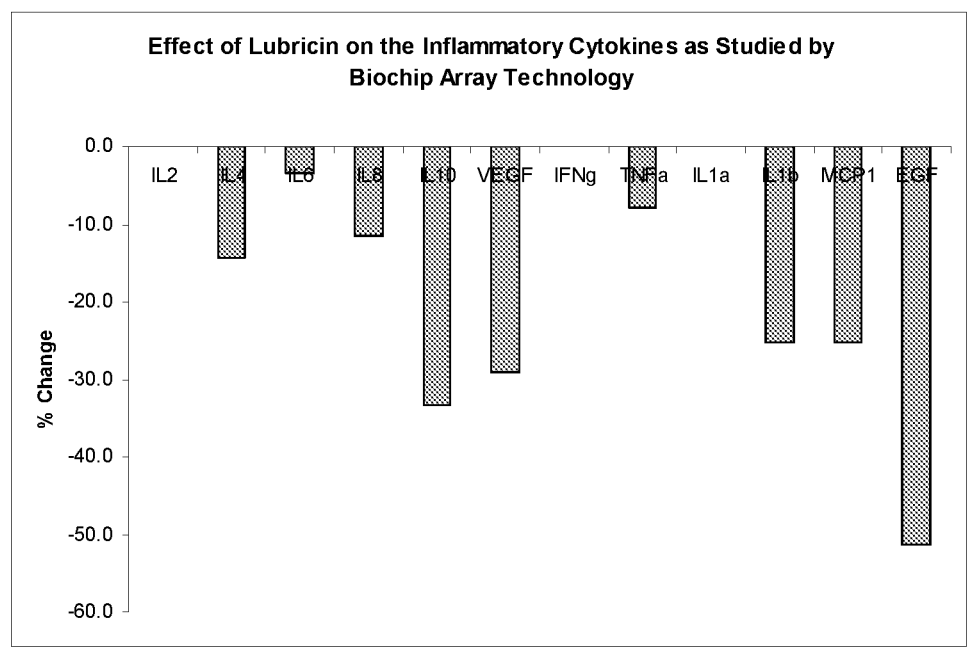

The effect of lubricin on LPS-mediated inflammatory cytokine generation was studied using Biochip Array technology. In these studies LPS alone at 10 ng/mL and LPS pre-supplementation at 10 ng/mL followed by lubricin supplementation at 0.57 mg/mL were compared in the whole citrated blood for the generation of various inflammatory cytokines. All samples were incubated for 60 minutes and centrifuged to obtain plasma. This plasma was subsequently analyzed using the biochip array for inflammatory cytokines. LPS was supplemented to whole blood in a 1:10 dilution. As shown in FIGS. 10A-B, the presence of lubricin resulted in a decrease in IL-4, IL-6, IL-8, IL-10, VEGF, TNF-α, IL-1β, MCP-1 and EGF, even though, as discussed above, presence of LPS alone resulted in an increase in production for each of these cytokines. As shown in FIG. 10B lubricin resulted in a marked decrease in the EGF, IL10, VEGF, MCP1, IL1b and TNF levels. These data suggest that supplementation of lubricin interferes with LPS-mediated inflammatory cytokine generation in a significant way, indicating that lubricin has anti-inflammatory properties.

Figure 11B:
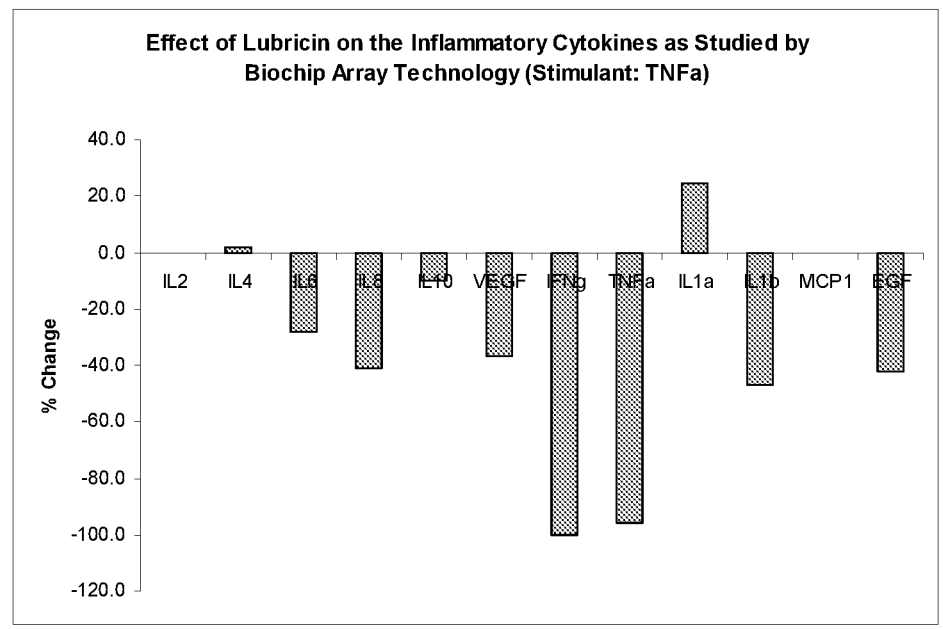

The effect of lubricin on TNF-α mediated inflammatory cytokine generation was studied using Biochip Array technology. Recombinant TNF-α was used as a trigger to generate inflammatory cytokines in whole blood. The effect of lubricin was studied on the TNF-α mediated generation of various cytokines. TNF-α alone at a concentration of 100 mg/mL was supplemented to the whole blood which was incubated for 60 minutes at 37° C. TNF-α was supplemented to whole blood in a 1:10 dilution. The modulatory effects of lubricin on TNF-α-mediated generation of various cytokines were studied by supplementing lubricin at 0.57 mg/mL in the whole blood immediately prior to addition of TNF-α. After 60 minutes plasma was obtained from centrifugation and analyzed for inflammatory cytokine using Randox Biochip arrays. As shown in FIGS. 11A-B, the presence of lubricin resulted in a decrease in IL-6, IL-8, IL-10, VEGF, TNF-α, IL-1β, and EGF, even though challenge with TNF-α alone resulted in the production of each these cytokines. FIG. 11B shows that lubricin decreased the levels of cytokines in a range of 10-100%. The most dramatic decrease in TNF-α stimulated cytokine expression was found to be the reduction of stimulated IFN-γ and TNF-α (as lubricin apparently interrupted a positive feedback loop of TNF-α production) as compared to stimulation in the absence of lubricin. These data suggest that administration of lubricin interferes with TNF-α-mediated inflammatory cytokine generation in a significant way, indicating that lubricin has anti-inflammatory properties.

Figure 12B:
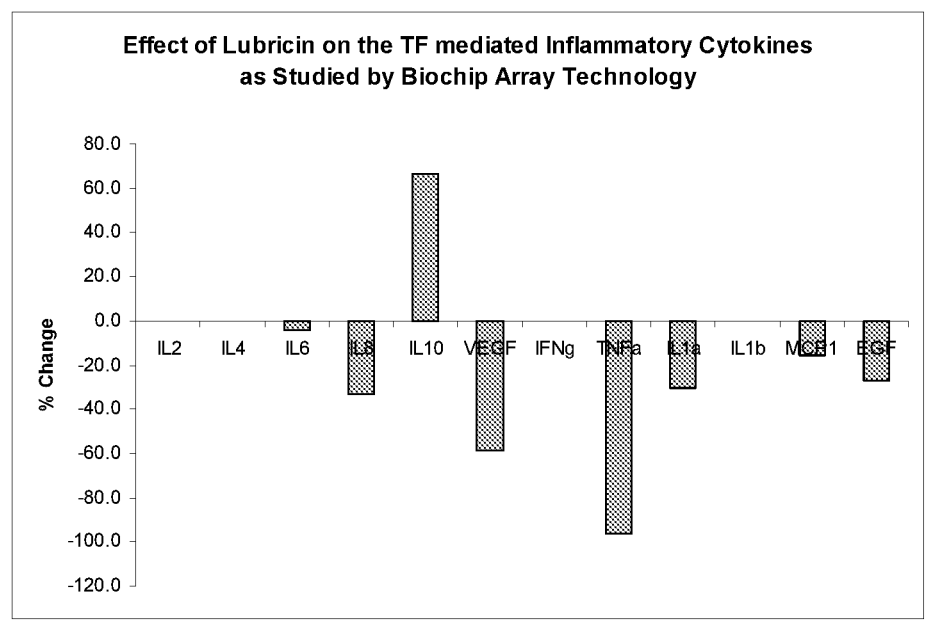

The effect of lubricin on recombinant tissue factor (TF) mediated inflammatory cytokine generation was studied using Biochip Array technology. In these studies recombiplastin brand (IL Laboratories) tissue factor was used to trigger the generation of inflammatory cytokines in human whole blood. The effect of lubricin at 0.57 mg/mL was studied by supplementing this agent prior to the addition of tissue factor to the whole blood. Tissue factor alone served as a positive control. The blood samples were centrifuged and plasma retrieved. This plasma was then profiled for the inflammatory cytokine profile on the Randox Biochip arrays. TF was supplemented to whole blood in a 1:10 dilution. As shown in FIGS. 12A-B, the presence of lubricin resulted in a decrease in IL-6, IL-8, VEGF, TNF-α, IL-1α, IL-1β, MCP-1 and EGF, even though challenge with TF alone resulted in the production of each these cytokines. As shown on FIG. 12B, lubricin produced a pronounced decrease in TNF-α and VEGF levels in tissue factor supplemented samples. These data suggest that administration of lubricin interferes with TF-mediated inflammatory cytokine generation in a significant way, indicating that lubricin has anti-inflammatory properties.

These studies show that lubricin is capable of inhibiting the generation of various inflammatory cytokines in whole blood which was supplemented bacterial lipopolysaccharide (LPS), TNF-α and tissue factor. All these agents are mediators of inflammation. Thus lubricin is capable of down-regulating the generation of inflammatory cytokines across a wide variety of mediators.

Example 3: Lubricin Reduces Levels of Pro-Inflammatory Cytokines In Vivo

Figure 13:
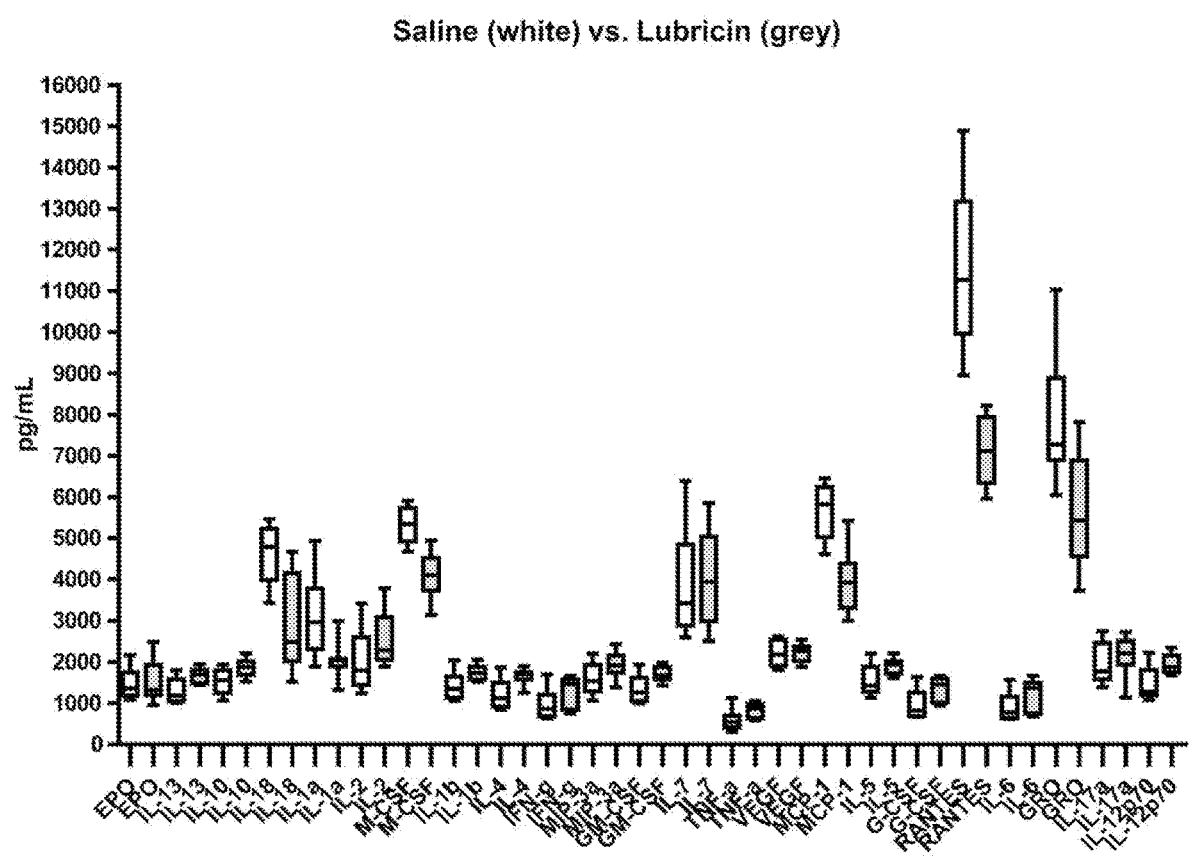
FIG. 13 is a graph showing EPO, IL-13, IL-10, IL-18, IL-1α, IL-2, MCSF, IL-1β, IL-4, IFN-γ, MIP-3α, GMCSF, IL-7, TNF-α, VEGF, MCP-1, IL-5, G-CSF, RANTES, IL-6, GRO, IL-17α, and IL-12p70 levels in serum samples taken from test mice receiving an intra-articular administration of recombinant human lubricin post-surgery (destabilization of the medial meniscus; grey bars) compared with control mice who received surgery but were administered saline rather than lubricin post-surgery (white bars).

In order to determine if lubricin could modulate pro-inflammatory cytokine levels in vivo, a rat model was used. Nine rats were subject to surgery to destabilize the medial meniscus (DMM surgery). Seven days after surgery, each rat received a single intraarticular dose of lubricin of 200 µg/kg. Control rats received an injection of an equal volume of saline. Cytokine levels in serum samples taken from the test mice were compared with control mice who received surgery but no dose of lubricin post-surgery. Samples were drawn 3 weeks after the dose of lubricin was administered and analyzed using the Luminex Multiplex platform. The results are shown in FIG. 13 where the measured levels of EPO, IL-13, IL-10, IL-18, IL-1α, IL-2, MCSF, IL-1β, IL-4, IFN-γ, MIP-3α, GMCSF, IL-7, TNF-α, VEGF, MCP-1, IL-5, G-CSF, RANTES, IL-6, GRO, IL-17α, and IL-12p70 are shown. The levels of IL-18, MCSF, MCP-1, RANTES, and GRO were all reduced in rats receiving lubricin as compared to rats that were injected with saline alone. More specifically, this shows the broad anti-inflammatory effects of lubricin, as this pattern of inflammatory cytokines was distinct from the TNF-α/IL-6/IL-8 dominated profile of the LPS and TF mediators (which were generally not upregulated in this model). Nevertheless, lubricin was able to significantly reduce pro-inflammatory cytokine production in vivo.

Figure 14A:
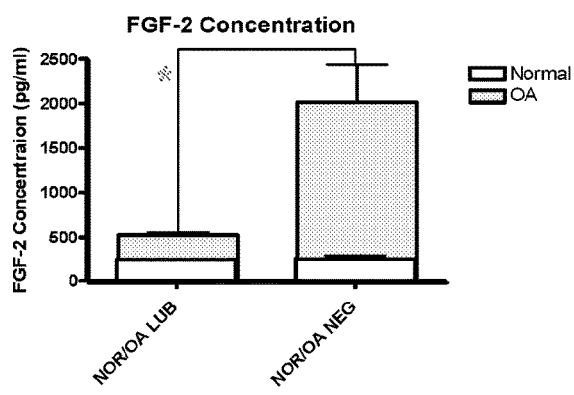
FIG. 14A-B are bar graphs showing the levels of cytokines expressed by osteoarthritic and normal human synoviocytes when exposed to recombinant human lubricin.
Figure 14B:
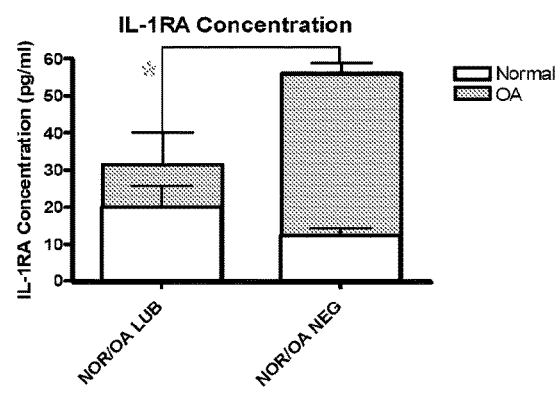

Example 4: The Effect of Lubricin on Cytokine Levels Secreted by Human Osteoarthritic Synoviocytes Synovial fluid cells were obtained from normal and osteoarthritic (OA) patients and purified with CD90+ following an immune cell depletion. The cells were plated at 10,000 per well and suspended in media containing DMEM, heat-inactivated Hyclone FBS (10%), and Anti-Anti (1%). The assays contained the cell suspension (cells+media) at 180 µL and the ligands at 20 µL for a total volume of 200 µL. Recombinant lubricin (rhPRG4) was then introduced to the cells at a concentration of 90 µg/mL and the negative control was PBS. The plate was then incubated at 37° C. at 5% $CO_2$ for 24 hours, after which the supernatants were collected for cytokine analysis via the Luminex multiplex platform. As shown in FIGS. 14A-B, normal cells did not show any changes in cytokine response when comparing the lubricin vs. PBS conditions. The OA cells, however, showed a down-regulation in FGF-2 and IL-1Ra cytokines when exposed to lubricin. Accordingly, in cells already exhibiting an inflammatory response, such as the osteoarthritic cells tested herein, administration of lubricin has the ability to reduce the levels of pro-inflammatory cytokines expressed from these cells.

Example 5: Treatment of Brain Injury

During head trauma there are frequently contusions of brain tissue and disruption of vascular integrity resulting in subarachnoid hemorrhage and/or subdural hematomas. Consequently, neurons are lost leading to compromised brain function. In addition, in CVA's and TIA's, one or more intra-vascular clots form, blocking oxygen and nutrient delivery to brain cells, including neurons, in a volume of the brain downstream of the blockage. This also leads to destruction of neurons, thereby compromising brain function. The brain immune response to injury involves an increased production of pro-inflammatory mediators and the recruitment of leukocytes to the area of injury. This contributes to neuronal damage in brain regions peripheral to the site of injury, termed the "penumbra," and exacerbates brain damage. Neuro-inflammation is one of the key mechanisms of secondary injury, and it is well established that post-traumatic neuro-inflammation significantly contributes to neuronal damage occurring after traumatic brain injury. One way to limit such brain damage is by administration of agents during a short interval (hours) after injury thereby reducing neuroinflammation and resulting neuronal damage. Accordingly, in an embodiment of the present invention, rhPRG4, also known as lubricin, can be administered systemically through the vasculature or during surgery to relieve pressure in the brain, as a means for limiting brain damage, Support for such treatment is supported by the results presented below.

Approximately one hour after traumatic brain injury to rats, using an established brain injury model involving a controlled cortical impact, rhPRG4 was administered intravenously to test rats at an approximate dose of 2.5 mg/Kg. Normal saline (0.9% NaCl) was administered intravenously to control rats. One day later, brains were harvested and the samples of the cerebral cortex surrounding the post-traumatic lesion were analyzed using Western blotting. The analysis demonstrated that rhPRG4 reduced the post-traumatic production of proinflammatory mediators when compared with controls.

Galectin 3, whose brain expression is rapidly increased and maintained at a high level for an extended period of time after traumatic brain injury, was down regulated by 74%. A 60% reduction in the magnitude of post-traumatic influx of monocytes into the injured brain parenchyma was also observed in rhPRG4-treated rats, when compared with normal saline-treated rats, and rhPRG4 also substantially attenuated (by 94%) the post-traumatic synthesis of matrix metalloproteinase 9 and inhibited (by 64%) the conversion of pro-matrix metalloproteinase 2 to its enzymatically active form. In addition, rhPRG4 reduced by 80% the permeability of the blood-brain barrier, which was evaluated by assessing the level of albumin in traumatized brain tissue.

Injection of fluorescently labeled rhPRG4 showed that it enters the brain parenchyma in the injured areas of the brain, while being totally absent from the undamaged areas of the brain. Together with the results of in vitro studies involving the monocytic cell line THP-1, these observations indicate that rhPRG4 limits the magnitude of post-traumatic neuro-inflammation by both directly inhibiting the chemotactic activity of invading inflammatory cells, and by curtailing the production and signaling of pro-inflammatory mediators.

Thus, rhPRG4 selectively targets the injured areas of the brain, reducing the likelihood of off-target pharmacological effects. Recombinant hPRG4 limits, with high efficacy, the magnitude of neuro-inflammation caused by traumatic brain injury, by reducing the post-traumatic production of proinflammatory mediators and the influx of inflammatory cells. Also, rhPRG4 exhibits a unique ability to stabilize the blood-brain barrier. The discovery of this novel rhPRG4 property is of great significance for treatment of brain injury, as blood-brain barrier dysfunction observed in brain injury not only contributes to neuronal death in the acute stage of injury, but also leads to progressive neurodegenerative changes in the injured brain and, consequently, poor neurological outcomes.

Example 6: Treatment of Inflammatory Bowel Disease

Inflammatory bowel disease is characterized by a cytokine mediated recruitment of activated T cells that results in oxidative damage and a wearing of the intestinal epithelium. It is estimated that 25%-40% of people with ulcerative colitis (UC) or Crohn's disease may progress to surgery, such as an ileal pouch anal anastomosis, or proctocolectomy that removes portions of the colon and rectum. Common therapies include broad spectrum anti-inflammatory medications such as corticosteroids, anti-TNF antibodies, or more targeted anti-integrin antibodies that aim to prevent gut-homing T-cell mobility. None of these approaches are suitable for long term therapy because of serious side effects such as infections and cancer that accompany these approaches. By contrast, recombinant hPRG4 can be selectively applied to the gut to both replenish the missing epithelial glycocalyx and reduce cytokine expression locally. A recent characterization of the cytokine profile of predominantly colonic inflammatory bowel disease revealed increased TNF-α, GRO, CCL11 (eotaxin) in UC, IL-6 in Crohn's, and IL-8 in both UC and Crohn's versus controls (Korolkova et al., *Clin Med Insights Gastroenerol* 2015 May 6; 8:29-44). Lubricin has been shown to significantly reduce expression of these cytokines. In one embodiment, rhPRG4 is administered via enema or orally, whether through gavage, whole bowel irrigation, drinking a solution, or through encapsulated pills (e.g., microparticle encapsulation, nanoparticle encapsulation, polymer encapsulation, etc.). By way of example, an enema administration of 100 mL to 4 L rhPRG4 in concentrations ranging from 10 µg/mL to 200 µg/mL, more preferably volumes of 200 mL to 500 mL in concentrations from 50 µg/mL to 150 µg/mL, suspended in an intestinally acceptable buffered salt solution, replenishes the glycocalyx, prevents T cell homing and downregulates cytokine expression in the locality of the administered lubricin. Administration of rhPRG4 results in improved epithelial barrier function, less vascular permeability, less susceptibility to protease activity, and improved nutrient absorption. In certain embodiments, a magnesium citrate or other laxative is administered up to 24 hours prior to lubricin administration, followed by appropriate fasting.

Example 7: Treatment of Gout

Rats undergoing injection of sodium urate crystals were studied as a model of gout. 24 hours following the sodium urate crystal administration, rats developed joint pain. Two rats received saline while another two rats received rhPRG4 injection 24 hours after the urate crystals were introduced. These rats were studied every 12 hours utilizing the Von Frey method. This method determines afferent pain sensitization as a result of joint inflammation by probing the paws of the affected limb with a thin filament wire. The data in FIG. 15 shows that the rats that received rhPRG4 were in less pain than rats which received placebo.

While preferred embodiments of the present invention have been shown and described herein, it will be apparent to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Other features and advantages of the invention will be apparent from the following description of the preferred embodiments thereof and from the claims. These and many other variations and embodiments of the invention will be apparent to one of skill in the art upon a review of the description and examples.

What is claimed is:

1. A method of treating an inflammatory bowel disease in a patient suffering from the inflammatory bowel disease, comprising administering proteoglycan 4 (PRG4) comprising the amino acid sequence of residues 25-1404 of SEQ ID NO:1 to the gastrointestinal tract of the patient in need thereof by oral administration, rectal administration, administration to the colon, administration to the small intestine, administration to the stomach, or through a combination thereof.

2. The method of claim 1, wherein the PRG4 is recombinant exogenous human PRG4.

3. The method of claim 1, wherein PRG4 is administered in an amount insufficient to provide boundary lubrication in the patient.

4. The method of claim 1, wherein PRG4 is administered in an amount ranging from 0.1 µg/kg-4000 µg/kg.

5. The method of claim 1, wherein said PRG4
   a) binds a CD44 receptor on a cell in said patient;
   b) reduces or inhibits the production of a pro-inflammatory cytokine in said patient; and/or
   c) reduces or inhibits the translocation of NF-κB in a cell in said patient, thereby reducing or inhibiting the inflammatory response in said patient.

6. The method of claim 5, wherein the cell is a gastric cell, intestinal cell, or colon cell.

7. The method of claim 5, wherein the pro-inflammatory cytokine is selected from the group consisting of IL-6, IL-8, TNF-α, CCL11, and GRO.

8. The method of claim 1, wherein the inflammatory bowel disease is Crohn's disease or ulcerative colitis.

9. The method of claim 1, wherein the PRG4 is administered orally.

10. The method of claim 9, wherein the PRG4 is administered orally into the gastrointestinal tract of the patient as a tablet, a capsule, as a solution by ingestion, or by feeding tube.

11. The method of claim 10, wherein the tablet or capsule comprises a substance that degrades when exposed to conditions present in the gastrointestinal tract.

12. The method of claim 1, wherein the PRG4 is administered rectally.

13. The method of claim 12, wherein the PRG4 is administered by enema.

14. The method of claim 13, wherein the PRG4 is administered in an amount of 100 mL to 4 L in a concentration ranging from 10 µg/mL to 200 µg/mL.

15. The method of claim 1, wherein the PRG4 is administered to the bowel via a colostomy.

16. The method of claim 1, wherein the PRG4 is administered to the small intestine or large intestine by J-tube.

17. The method of claim 1, wherein administration of a laxative followed by fasting precedes administering the PRG4.

18. The method of claim 1, wherein the PRG4 is administered by injection directly to the stomach, colon, small-intestine, or rectum.

19. The method of claim 1, wherein PRG4 is administered locally to provide a coating of PRG4 from a PRG4 solution.

* * * * *

SEQUENCE LISTING

```
<160> NUMBER OF SEQ ID NOS: 3

<210> SEQ ID NO 1
<211> LENGTH: 1404
<212> TYPE: PRT
<213> ORGANISM: Homo sapiens

<400> SEQUENCE: 1

Met Ala Trp Lys Thr Leu Pro Ile Tyr Leu Leu Leu Leu Ser Val
1               5                   10                  15

Phe Val Ile Gln Gln Val Ser Ser Gln Asp Leu Ser Ser Cys Ala Gly
            20                  25                  30

Arg Cys Gly Glu Gly Tyr Ser Arg Asp Ala Thr Cys Asn Cys Asp Tyr
            35                  40                  45

Asn Cys Gln His Tyr Met Glu Cys Cys Pro Asp Phe Lys Arg Val Cys
        50                  55                  60

Thr Ala Glu Leu Ser Cys Lys Gly Arg Cys Phe Glu Ser Phe Glu Arg
65                  70                  75                  80

Gly Arg Glu Cys Asp Cys Asp Ala Gln Cys Lys Lys Tyr Asp Lys Cys
                85                  90                  95

Cys Pro Asp Tyr Glu Ser Phe Cys Ala Glu Val His Asn Pro Thr Ser
                100                 105                 110

Pro Pro Ser Ser Lys Lys Ala Pro Pro Pro Ser Gly Ala Ser Gln Thr
            115                 120                 125

Ile Lys Ser Thr Thr Lys Arg Ser Pro Lys Pro Pro Asn Lys Lys Lys
        130                 135                 140

Thr Lys Lys Val Ile Glu Ser Glu Glu Ile Thr Glu Glu His Ser Val
145                 150                 155                 160

Ser Glu Asn Gln Glu Ser Ser Ser Ser Ser Ser Ser Ser Ser Ser Ser
                165                 170                 175

Ser Thr Ile Arg Lys Ile Lys Ser Ser Lys Asn Ser Ala Ala Asn Arg
                180                 185                 190

Glu Leu Gln Lys Lys Leu Lys Val Lys Asp Asn Lys Lys Asn Arg Thr
            195                 200                 205

Lys Lys Lys Pro Thr Pro Lys Pro Pro Val Val Asp Glu Ala Gly Ser
        210                 215                 220

Gly Leu Asp Asn Gly Asp Phe Lys Val Thr Thr Pro Asp Thr Ser Thr
225                 230                 235                 240

Thr Gln His Asn Lys Val Ser Thr Ser Pro Lys Ile Thr Thr Ala Lys
                245                 250                 255

Pro Ile Asn Pro Arg Pro Ser Leu Pro Pro Asn Ser Asp Thr Ser Lys
                260                 265                 270

Glu Thr Ser Leu Thr Val Asn Lys Glu Thr Thr Val Glu Thr Lys Glu
            275                 280                 285

Thr Thr Thr Thr Asn Lys Gln Thr Ser Thr Asp Gly Lys Glu Lys Thr
        290                 295                 300

Thr Ser Ala Lys Glu Thr Gln Ser Ile Glu Lys Thr Ser Ala Lys Asp
305                 310                 315                 320

Leu Ala Pro Thr Ser Lys Val Leu Ala Lys Pro Thr Pro Lys Ala Glu
```

```
                        325                 330                 335
Thr Thr Thr Lys Gly Pro Ala Leu Thr Thr Pro Lys Glu Pro Thr Pro
                340                 345                 350
Thr Thr Pro Lys Glu Pro Ala Ser Thr Thr Pro Lys Glu Pro Thr Pro
                355                 360                 365
Thr Thr Ile Lys Ser Ala Pro Thr Thr Pro Lys Glu Pro Ala Pro Thr
            370                 375                 380
Thr Thr Lys Ser Ala Pro Thr Thr Pro Lys Glu Pro Ala Pro Thr Thr
385                 390                 395                 400
Thr Lys Glu Pro Ala Pro Thr Thr Pro Lys Glu Pro Ala Pro Thr Thr
                405                 410                 415
Thr Lys Glu Pro Ala Pro Thr Thr Lys Ser Ala Pro Thr Thr Pro
                420                 425                 430
Lys Glu Pro Ala Pro Thr Thr Pro Lys Lys Pro Ala Pro Thr Thr Pro
                435                 440                 445
Lys Glu Pro Ala Pro Thr Thr Pro Lys Glu Pro Thr Pro Thr Thr Pro
450                 455                 460
Lys Glu Pro Ala Pro Thr Thr Lys Glu Pro Ala Pro Thr Thr Pro Lys
465                 470                 475                 480
Glu Pro Ala Pro Thr Ala Pro Lys Lys Pro Ala Pro Thr Thr Pro Lys
                485                 490                 495
Glu Pro Ala Pro Thr Thr Pro Lys Glu Pro Ala Pro Thr Thr Thr Lys
                500                 505                 510
Glu Pro Ser Pro Thr Thr Pro Lys Glu Pro Ala Pro Thr Thr Thr Lys
                515                 520                 525
Ser Ala Pro Thr Thr Thr Lys Glu Pro Ala Pro Thr Thr Thr Lys Ser
            530                 535                 540
Ala Pro Thr Thr Pro Lys Glu Pro Ser Pro Thr Thr Thr Lys Glu Pro
545                 550                 555                 560
Ala Pro Thr Thr Pro Lys Glu Pro Ala Pro Thr Thr Pro Lys Lys Pro
                565                 570                 575
Ala Pro Thr Thr Pro Lys Glu Pro Ala Pro Thr Thr Pro Lys Glu Pro
                580                 585                 590
Ala Pro Thr Thr Thr Lys Lys Pro Ala Pro Thr Thr Pro Lys Glu Pro
                595                 600                 605
Ala Pro Thr Thr Pro Lys Glu Thr Ala Pro Thr Thr Pro Lys Lys Leu
            610                 615                 620
Thr Pro Thr Thr Pro Glu Lys Leu Ala Pro Thr Thr Pro Glu Lys Pro
625                 630                 635                 640
Ala Pro Thr Thr Pro Glu Glu Leu Ala Pro Thr Thr Pro Glu Glu Pro
                645                 650                 655
Thr Pro Thr Thr Pro Glu Glu Pro Ala Pro Thr Thr Pro Lys Ala Ala
            660                 665                 670
Ala Pro Asn Thr Pro Lys Glu Pro Ala Pro Thr Thr Pro Lys Glu Pro
            675                 680                 685
Ala Pro Thr Thr Pro Lys Glu Pro Ala Pro Thr Thr Pro Lys Glu Thr
            690                 695                 700
Ala Pro Thr Thr Pro Lys Gly Thr Ala Pro Thr Thr Leu Lys Glu Pro
705                 710                 715                 720
Ala Pro Thr Thr Pro Lys Lys Pro Ala Pro Lys Glu Leu Ala Pro Thr
                725                 730                 735
Thr Thr Lys Glu Pro Thr Ser Thr Thr Cys Asp Lys Pro Ala Pro Thr
            740                 745                 750
```

-continued

```
Thr Pro Lys Gly Thr Ala Pro Thr Thr Pro Lys Glu Pro Ala Pro Thr
        755                 760                 765
Thr Pro Lys Glu Pro Ala Pro Thr Thr Pro Lys Gly Thr Ala Pro Thr
        770                 775                 780
Thr Leu Lys Glu Pro Ala Pro Thr Thr Pro Lys Lys Pro Ala Pro Lys
785                 790                 795                 800
Glu Leu Ala Pro Thr Thr Thr Lys Gly Pro Thr Ser Thr Thr Ser Asp
                805                 810                 815
Lys Pro Ala Pro Thr Thr Pro Lys Glu Thr Ala Pro Thr Thr Pro Lys
                820                 825                 830
Glu Pro Ala Pro Thr Thr Pro Lys Lys Pro Ala Pro Thr Thr Pro Glu
                835                 840                 845
Thr Pro Pro Pro Thr Thr Ser Glu Val Ser Thr Pro Thr Thr Thr Lys
        850                 855                 860
Glu Pro Thr Thr Ile His Lys Ser Pro Asp Glu Ser Thr Pro Glu Leu
865                 870                 875                 880
Ser Ala Glu Pro Thr Pro Lys Ala Leu Glu Asn Ser Pro Lys Glu Pro
                885                 890                 895
Gly Val Pro Thr Thr Lys Thr Pro Ala Ala Thr Lys Pro Glu Met Thr
        900                 905                 910
Thr Thr Ala Lys Asp Lys Thr Thr Glu Arg Asp Leu Arg Thr Thr Pro
        915                 920                 925
Glu Thr Thr Thr Ala Ala Pro Lys Met Thr Lys Glu Thr Ala Thr Thr
        930                 935                 940
Thr Glu Lys Thr Thr Glu Ser Lys Ile Thr Ala Thr Thr Gln Val
945                 950                 955                 960
Thr Ser Thr Thr Thr Gln Asp Thr Thr Pro Phe Lys Ile Thr Thr Leu
                965                 970                 975
Lys Thr Thr Thr Leu Ala Pro Lys Val Thr Thr Thr Lys Lys Thr Ile
                980                 985                 990
Thr Thr Thr Glu Ile Met Asn Lys Pro Glu Glu Thr Ala Lys Pro Lys
        995                 1000                1005
Asp Arg Ala Thr Asn Ser Lys Ala Thr Thr Pro Lys Pro Gln Lys
        1010                1015                1020
Pro Thr Lys Ala Pro Lys Lys Pro Thr Ser Thr Lys Lys Pro Lys
        1025                1030                1035
Thr Met Pro Arg Val Arg Lys Pro Lys Thr Thr Pro Thr Pro Arg
        1040                1045                1050
Lys Met Thr Ser Thr Met Pro Glu Leu Asn Pro Thr Ser Arg Ile
        1055                1060                1065
Ala Glu Ala Met Leu Gln Thr Thr Thr Arg Pro Asn Gln Thr Pro
        1070                1075                1080
Asn Ser Lys Leu Val Glu Val Asn Pro Lys Ser Glu Asp Ala Gly
        1085                1090                1095
Gly Ala Glu Gly Glu Thr Pro His Met Leu Leu Arg Pro His Val
        1100                1105                1110
Phe Met Pro Glu Val Thr Pro Asp Met Asp Tyr Leu Pro Arg Val
        1115                1120                1125
Pro Asn Gln Gly Ile Ile Ile Asn Pro Met Leu Ser Asp Glu Thr
        1130                1135                1140
Asn Ile Cys Asn Gly Lys Pro Val Asp Gly Leu Thr Thr Leu Arg
        1145                1150                1155
```

```
Asn Gly Thr Leu Val Ala Phe Arg Gly His Tyr Phe Trp Met Leu
    1160                1165                1170

Ser Pro Phe Ser Pro Pro Ser Pro Ala Arg Arg Ile Thr Glu Val
    1175                1180                1185

Trp Gly Ile Pro Ser Pro Ile Asp Thr Val Phe Thr Arg Cys Asn
    1190                1195                1200

Cys Glu Gly Lys Thr Phe Phe Lys Asp Ser Gln Tyr Trp Arg
    1205                1210                1215

Phe Thr Asn Asp Ile Lys Asp Ala Gly Tyr Pro Lys Pro Ile Phe
    1220                1225                1230

Lys Gly Phe Gly Gly Leu Thr Gly Gln Ile Val Ala Ala Leu Ser
    1235                1240                1245

Thr Ala Lys Tyr Lys Asn Trp Pro Glu Ser Val Tyr Phe Phe Lys
    1250                1255                1260

Arg Gly Gly Ser Ile Gln Gln Tyr Ile Tyr Lys Gln Glu Pro Val
    1265                1270                1275

Gln Lys Cys Pro Gly Arg Arg Pro Ala Leu Asn Tyr Pro Val Tyr
    1280                1285                1290

Gly Glu Thr Thr Gln Val Arg Arg Arg Phe Glu Arg Ala Ile
    1295                1300                1305

Gly Pro Ser Gln Thr His Thr Ile Arg Ile Gln Tyr Ser Pro Ala
    1310                1315                1320

Arg Leu Ala Tyr Gln Asp Lys Gly Val Leu His Asn Glu Val Lys
    1325                1330                1335

Val Ser Ile Leu Trp Arg Gly Leu Pro Asn Val Val Thr Ser Ala
    1340                1345                1350

Ile Ser Leu Pro Asn Ile Arg Lys Pro Asp Gly Tyr Asp Tyr Tyr
    1355                1360                1365

Ala Phe Ser Lys Asp Gln Tyr Tyr Asn Ile Asp Val Pro Ser Arg
    1370                1375                1380

Thr Ala Arg Ala Ile Thr Thr Arg Ser Gly Gln Thr Leu Ser Lys
    1385                1390                1395

Val Trp Tyr Asn Cys Pro
    1400

<210> SEQ ID NO 2
<211> LENGTH: 5041
<212> TYPE: DNA
<213> ORGANISM: Homo sapiens

<400> SEQUENCE: 2
gcggccgcga ctattcggta cctgaaaaca acgatggcat ggaaaacact tcccatttac      60
ctgttgttgc tgctgtctgt tttcgtgatt cagcaagttt catctcaaga tttatcaagc     120
tgtgcaggga gatgtgggga agggtattct agagatgcca cctgcaactg tgattataac     180
tgtcaacact acatggagtg ctgccctgat ttcaagagag tctgcactgc ggagctttcc     240
tgtaaaggcc gctgctttga gtccttcgag agagggaggg agtgtgactg cgacgcccaa     300
tgtaagaagt atgacaagtg ctgtcccgat tatgagagtt tctgtgcaga agtgcataat     360
cccacatcac caccatcttc aaagaaagca cctccacctt caggagcatc tcaaaccatc     420
aaatcaacaa ccaaacgttc acccaaacca ccaaacaaga gaagactaa gaaagttata     480 gaatcagagg aaataacaga agaacattct gtttctgaaa atcagagtc ctcctcctcc     540 tcctcctctt cctcttcttc ttcaacaatt tggaaaatca agtcttccaa aaattcagct     600
```

| | |
|---|---|
| gctaatagag aattacagaa gaaactcaaa gtaaaagata acaagaagaa cagaactaaa | 660 |
| aagaaaccta cccccaaacc accagttgta gatgaagctg gaagtggatt ggacaatggt | 720 |
| gacttcaagg tcacaactcc tgacacgtct accacccaac acaataaagt cagcacatct | 780 |
| cccaagatca aacagcaaa accaataaat cccagaccca gtcttccacc taattctgat | 840 |
| acatctaaag agacgtcttt gacagtgaat aaagagacaa cagttgaaac taaagaaact | 900 |
| actacaacaa ataaacagac ttcaactgat ggaaaagaga agactacttc cgctaaagag | 960 |
| acacaaagta tagagaaaac atctgctaaa gatttagcac ccacatctaa agtgctggct | 1020 |
| aaacctacac ccaaagctga aactacaacc aaaggccctg ctctcaccac tcccaaggag | 1080 |
| cccacgccca ccactcccaa ggagcctgca tctaccacac ccaaagagcc cacacctacc | 1140 |
| accatcaagt ctgcacccac cacccccaag gagcctgcac ccaccaccac caagtctgca | 1200 |
| cccaccactc caaggagcc tgcacccacc accaccaagg agcctgcacc caccactccc | 1260 |
| aaggagcctg cacccaccac caccaaggag cctgcaccca ccaccaa gtctgcaccc | 1320 |
| accactccca aggagcctgc acccaccacc cccaagaagc tgccccaac tacccccaag | 1380 |
| gagcctgcac ccaccactcc caaggagcct acacccacca ctcccaagga gcctgcaccc | 1440 |
| accaccaagg agcctgcacc caccactccc aaagagcctg cacccactgc ccccaagaag | 1500 |
| cctgccccaa ctaccccaa ggagcctgca cccaccactc caaggagcc tgcacccacc | 1560 |
| accaccaagg agccttcacc caccactccc aaggagcctg cacccaccac caccaagtct | 1620 |
| gcacccacca ctaccaagga gcctgcaccc accactacca agtctgcacc caccactccc | 1680 |
| aaggagcctt cacccaccac caccaaggag cctgcaccca ccactcccaa ggagcctgca | 1740 |
| cccaccaccc ccaagaagcc tgccccaact accccaagg agcctgcacc caccactccc | 1800 |
| aaggaacctg cacccaccac caccaagaag cctgcaccca ccgctcccaa agagcctgcc | 1860 |
| ccaactaccc caaggagac tgcacccacc accccaaga agctcacgcc caccaccccc | 1920 |
| gagaagctcg cacccaccac ccctgagaag cccgcaccca ccaccctga ggagctcgca | 1980 |
| cccaccaccc ctgaggagcc cacacccacc accctgagg agcctgctcc caccactccc | 2040 |
| aaggcagcgg ctcccaacac ccctaaggag cctgctccaa ctaccctaa ggagcctgct | 2100 |
| ccaactaccc ctaaggagcc tgctccaact accctaagg agactgctcc aactacccct | 2160 |
| aaagggactg ctccaactac cctcaaggaa cctgcaccca ctactcccaa gaagcctgcc | 2220 |
| cccaaggagc ttgcacccac caccaccaag gagcccacat ccaccacctc tgacaagccc | 2280 |
| gctccaacta cccctaaggg gactgctcca actaccccta aggagcctgc tccaactacc | 2340 |
| cctaaggagc ctgctccaac taccctaag gggactgctc caactaccct caaggaacct | 2400 |
| gcacccacta ctcccaagaa gcctgccccc aaggagcttg cacccaccac caccaagggg | 2460 |
| cccacatcca ccacctctga caagcctgct ccaactacac ctaaggagac tgctccaact | 2520 |
| accccccaagg agcctgcacc cactaccccc aagaagcctg ctccaactac tcctgagaca | 2580 |
| cctcctccaa ccacttcaga ggtctctact ccaactacca ccaaggagcc taccactatc | 2640 |
| cacaaaagcc ctgatgaatc aactcctgag ctttctgcag aacccacacc aaaagctctt | 2700 |
| gaaaacagtc ccaaggaacc tggtgtacct acaactaaga ctcctgcagc gactaaacct | 2760 |
| gaaatgacta caacagctaa agacaagaca acagaaagag acttacgtac tacacctgaa | 2820 |
| actacaactg ctgcacctaa gatgacaaaa gagacagcaa ctacaacaga aaaaactacc | 2880 |
| gaatccaaaa taacagctac aaccacacaa gtaacatcta ccacaactca agataccaca | 2940 |
| ccattcaaaa ttactactct taaaacaact actcttgcac ccaaagtaac tacaacaaaa | 3000 |

```
aagacaatta ctaccactga gattatgaac aaacctgaag aaacagctaa accaaaagac   3060
agagctacta attctaaagc gacaactcct aaacctcaaa agccaaccaa agcacccaaa   3120
aaacccactt ctaccaaaaa gccaaaaaca atgcctagag tgagaaaacc aaagacgaca   3180
ccaactcccc gcaagatgac atcaacaatg ccagaattga accctacctc aagaatagca   3240
gaagccatgc tccaaaccac caccagacct aaccaaactc caaactccaa actagttgaa   3300
gtaaatccaa agagtgaaga tgcaggtggt gctgaaggaa aaacacctca tatgcttctc   3360
aggccccatg tgttcatgcc tgaagttact cccgacatgg attacttacc gagagtaccc   3420
aatcaaggca ttatcatcaa tcccatgctt ccgatgaga ccaatatatg caatggtaag    3480
ccagtagatg gactgactac tttgcgcaat gggacattag ttgcattccg aggtcattat   3540
ttctggatgc taagtccatt cagtccacca tctccagctc gcagaattac tgaagtttgg   3600
ggtattcctt cccccattga tactgttttt actaggtgca actgtgaagg aaaaactttc   3660
ttctttaagg attctcagta ctggcgtttt accaatgata taaagatgc agggtaccc   3720 aaaccaattt tcaaaggatt tggaggacta actggacaaa tagtggcagc ctttcaaca   3780 gctaaatata agaactggcc tgaatctgtg tatttttttca agagaggtgg cagcattcag   3840
cagtatattt ataaacagga acctgtacag aagtgccctg aagaaggcc tgctctaaat   3900 tatccagtgt atggagaaat gacacaggtt aggagacgtc gctttgaacg tgctatagga   3960
ccttctcaaa cacacaccat cagaattcaa tattcacctg ccagactggc ttatcaagac   4020
aaaggtgtcc ttcataatga agttaaagtg agtatactgt ggagaggact tccaaatgtg   4080
gttacctcag ctatatcact gcccaacatc agaaaacctg acggctatga ttactatgcc   4140
ttttctaaag atcaatacta taacattgat gtgcctagta aacagcaag agcaattact   4200 actcgttctg ggcagacctt atccaaagtc tggtacaact gtccttagac tgatgagcaa   4260
aggaggagtc aactaatgaa gaaatgaata ataaattttg acactgaaaa acatttatt    4320 aataaagaat attgacatga gtataccagt ttatatataa aaatgttttt aaacttgaca   4380
atcattacac taaaacagat ttgataatct tattcacagt tgttattgtt tacagaccat   4440
ttaattaata tttcctctgt ttattcctcc tctccctccc attgcatggc tcacacctgt   4500
aaaagaaaaa agaatcaaat tgaatatatc ttttaagaat tcaaactag tgtattcact   4560 taccctagtt cattataaaa aatatctagg cattgtggat ataaaactgt tgggtattct   4620
acaacttcaa tggaaattat tacaagcaga ttaatccctc tttttgtgac acaagtacaa   4680
tctaaaagtt atattggaaa acatggaaat attaaaattt tacacttttta ctagctaaaa   4740 cataatcaca aagctttatc gtgttgtata aaaaaattaa caatataatg gcaataggta   4800
gagatacaac aaatgaatat aacactataa cacttcatat tttccaaatc ttaatttgga   4860
tttaaggaag aaatcaataa atataaata taagcacata tttattatat atctaaggta   4920
tacaaatctg tctacatgaa gtttacagat tggtaaatat cacctgctca acatgtaatt   4980
atttaataaa actttggaac attaaaaaaa taaattggag gcttaaaaaa aaaaaaaaa   5040
a                                                                  5041
```

<210> SEQ ID NO 3
<211> LENGTH: 7
<212> TYPE: PRT
<213> ORGANISM: Homo sapiens

```
<400> SEQUENCE: 3

Lys Glu Pro Ala Pro Thr Thr
1               5
```